(12) United States Patent
Saadat et al.

(10) Patent No.: US 9,456,829 B2
(45) Date of Patent: Oct. 4, 2016

(54) POWERED TISSUE MODIFICATION DEVICES AND METHODS

(71) Applicant: Amendia, Inc., Marietta, GA (US)

(72) Inventors: Vahid Saadat, Atherton, CA (US);
Jeffery L. Bleich, Palo Alto, CA (US);
Kenneth J. Michlitsch, Livermore, CA (US); John E. Ashley, Danville, CA (US)

(73) Assignee: Amendia, Inc., Marietta, GA (US)

( * ) Notice: Subject to any disclaimer, the term of this patent is extended or adjusted under 35 U.S.C. 154(b) by 334 days.

(21) Appl. No.: 13/913,801

(22) Filed: Jun. 10, 2013

(65) Prior Publication Data

US 2013/0310837 A1    Nov. 21, 2013

Related U.S. Application Data

(63) Continuation of application No. 13/078,376, filed on Apr. 1, 2011, now abandoned, which is a continuation-in-part of application No. 11/406,486, filed on Apr. 17, 2006, now Pat. No. 7,938,830, which (Continued)

(51) Int. Cl.
*A61B 17/16* (2006.01)

(52) U.S. Cl.
CPC ....... *A61B 17/1659* (2013.01); *A61B 17/1671* (2013.01)

(58) Field of Classification Search
CPC .................. A61B 17/1659; A61B 17/1671
See application file for complete search history.

(56) References Cited

U.S. PATENT DOCUMENTS

| 184,804 A | 11/1876 | Stohlmann |
| 289,104 A | 11/1883 | How |
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |

(Continued)

FOREIGN PATENT DOCUMENTS

| CN | 1338911 A | 3/2002 |
| CN | 101291633 A | 10/2008 |

(Continued)

OTHER PUBLICATIONS

Bleich et al.; U.S. Appl. No. 14/180,221 entitled "Flexible tissue rasp," filed Feb. 13, 2014.

(Continued)

*Primary Examiner* — David Bates
(74) *Attorney, Agent, or Firm* — David L. King

(57) ABSTRACT

A device for modifying tissue in a spine may include: a shaft having a proximal portion and a distal portion, the distal portion having dimensions which allow it to be passed into an epidural space of the spine and between target and non-target tissues; at least one distal force application member extending from the distal portion of the shaft and configured to facilitate application of at least one of anchoring force and tensioning force to the shaft; at least one movable tissue modifying member coupled with the shaft at or near its distal portion; at least one drive member coupled with the at least one tissue modifying member to activate the at least one tissue modifying member; and at least one power transmission member coupled with the at least one drive member to deliver power to the at least one drive member.

6 Claims, 84 Drawing Sheets

Related U.S. Application Data is a continuation-in-part of application No. 11/375,265, filed on Mar. 13, 2006, now Pat. No. 7,887,538, which is a continuation-in-part of application No. PCT/US2005/037136, filed on Oct. 15, 2005, said application No. 13/078,376 is a continuation-in-part of application No. 11/405,848, filed on Apr. 17, 2006, now Pat. No. 8,430,881, which is a continuation-in-part of application No. 11/375,265, filed on Mar. 13, 2006, now Pat. No. 7,887,538, which is a continuation-in-part of application No. PCT/US2005/037136, filed on Oct. 15, 2005.

(60) Provisional application No. 60/619,306, filed on Oct. 15, 2004, provisional application No. 60/622,865, filed on Oct. 28, 2004, provisional application No. 60/681,719, filed on May 16, 2005, provisional application No. 60/681,864, filed on May 16, 2005, provisional application No. 60/685,190, filed on May 27, 2005.

(56) References Cited

U.S. PATENT DOCUMENTS

| | | | |
|---|---|---|---|
| 1,543,195 | A | 6/1925 | Thygesen |
| 1,690,812 | A | 11/1928 | Bertels |
| 1,938,200 | A | 12/1933 | Wells |
| 2,243,757 | A | 5/1941 | Kohls et al. |
| 2,269,749 | A | 1/1942 | Wilkie |
| 2,372,553 | A | 3/1945 | Coddington |
| 2,437,697 | A | 3/1948 | Kalom |
| 2,516,882 | A | 8/1950 | Kalom |
| 2,704,064 | A | 5/1955 | Fizzell |
| 2,820,281 | A | 1/1958 | Amsen |
| 2,843,128 | A | 7/1958 | Storz |
| 2,982,005 | A | 5/1961 | Booth |
| 3,124,824 | A | 3/1964 | Lutz |
| RE25,582 | E | 5/1964 | Davies |
| 3,150,470 | A | 9/1964 | Barron |
| 3,200,814 | A | 8/1965 | Taylor et al. |
| 3,214,824 | A | 11/1965 | Brown |
| 3,389,447 | A | 6/1968 | Theobald et al. |
| 3,491,776 | A | 1/1970 | Fleming |
| 3,495,590 | A | 2/1970 | Zeiller |
| 3,528,152 | A | 9/1970 | Funakubo et al. |
| 3,624,484 | A | 11/1971 | Colyer |
| 3,640,280 | A | 2/1972 | Slanker et al. |
| 3,651,844 | A | 3/1972 | Barnes |
| 3,664,329 | A | 5/1972 | Naylor |
| 3,682,162 | A | 8/1972 | Colyer |
| 3,699,729 | A | 10/1972 | Garvey et al. |
| 3,734,207 | A * | 5/1973 | Fishbein ............ A61B 17/1622 173/217 |
| 3,752,166 | A | 8/1973 | Lyon et al. |
| 3,774,355 | A | 11/1973 | Dawson et al. |
| 3,830,226 | A | 8/1974 | Staub et al. |
| 3,835,859 | A | 9/1974 | Roberts et al. |
| 3,956,858 | A | 5/1976 | Catlin et al. |
| 3,957,036 | A | 5/1976 | Normann |
| 3,978,862 | A | 9/1976 | Morrison |
| 3,999,294 | A | 12/1976 | Shoben |
| 4,015,931 | A | 4/1977 | Thakur |
| 4,099,519 | A | 7/1978 | Warren |
| 4,108,182 | A | 8/1978 | Hartman et al. |
| 4,160,320 | A | 7/1979 | Wikoff |
| 4,172,440 | A | 10/1979 | Schneider et al. |
| 4,203,444 | A | 5/1980 | Bonnell et al. |
| 4,207,897 | A | 6/1980 | Lloyd et al. |
| 4,259,276 | A | 3/1981 | Rawlings |
| 4,405,061 | A | 9/1983 | Bergandy |
| D273,806 | S | 5/1984 | Bolesky et al. |
| 4,464,836 | A | 8/1984 | Hissa |
| 4,466,429 | A * | 8/1984 | Loscher ............ A61B 17/1659 606/180 |
| 4,502,184 | A | 3/1985 | Karubian |
| 4,515,168 | A | 5/1985 | Chester et al. |
| 4,518,022 | A | 5/1985 | Valdes et al. |
| 4,545,374 | A | 10/1985 | Jacobson |
| 4,573,448 | A | 3/1986 | Kambin |
| 4,580,545 | A | 4/1986 | Dorsten |
| 4,590,949 | A | 5/1986 | Pohndorf |
| 4,616,660 | A | 10/1986 | Johns |
| 4,621,636 | A | 11/1986 | Fogarty |
| 4,625,725 | A | 12/1986 | Davison et al. |
| 4,660,571 | A | 4/1987 | Hess et al. |
| 4,678,459 | A | 7/1987 | Onik et al. |
| 4,690,642 | A | 9/1987 | Kyotani |
| 4,700,702 | A | 10/1987 | Nilsson |
| 4,709,699 | A | 12/1987 | Michael et al. |
| 4,741,343 | A | 5/1988 | Bowman |
| 4,750,249 | A | 6/1988 | Richardson |
| 4,794,931 | A | 1/1989 | Yock |
| 4,808,157 | A | 2/1989 | Coombs |
| 4,817,628 | A | 4/1989 | Zealear et al. |
| 4,856,193 | A | 8/1989 | Grachan |
| 4,867,155 | A | 9/1989 | Isaacson |
| 4,872,452 | A | 10/1989 | Alexson |
| 4,873,978 | A | 10/1989 | Ginsburg |
| 4,883,460 | A | 11/1989 | Zanetti |
| 4,894,063 | A | 1/1990 | Nashe |
| 4,912,799 | A | 4/1990 | Coleman, Jr. |
| RE33,258 | E | 7/1990 | Onik et al. |
| 4,943,295 | A | 7/1990 | Hartlaub et al. |
| 4,946,462 | A | 8/1990 | Watanabe |
| 4,957,117 | A | 9/1990 | Wysham |
| 4,962,766 | A | 10/1990 | Herzon |
| 4,973,329 | A | 11/1990 | Park et al. |
| 4,990,148 | A | 2/1991 | Worrick, III et al. |
| 4,994,036 | A | 2/1991 | Biscoping et al. |
| 4,994,072 | A | 2/1991 | Bhate et al. |
| 4,995,200 | A | 2/1991 | Eberhart |
| 5,019,082 | A | 5/1991 | Frey et al. |
| 5,025,787 | A | 6/1991 | Sutherland et al. |
| 5,026,379 | A | 6/1991 | Yoon |
| 5,026,386 | A | 6/1991 | Michelson |
| 5,078,137 | A | 1/1992 | Edell et al. |
| 5,089,003 | A | 2/1992 | Fallin et al. |
| 5,100,424 | A | 3/1992 | Jang et al. |
| 5,108,403 | A | 4/1992 | Stern |
| 5,123,400 | A | 6/1992 | Edgerton |
| 5,125,928 | A | 6/1992 | Parins et al. |
| 5,147,364 | A | 9/1992 | Comparetto |
| 5,152,749 | A | 10/1992 | Giesy et al. |
| 5,161,534 | A | 11/1992 | Berthiaume |
| 5,163,939 | A | 11/1992 | Winston |
| 5,176,649 | A | 1/1993 | Wakabayashi |
| 5,178,145 | A | 1/1993 | Rea |
| 5,178,161 | A | 1/1993 | Kovacs |
| 5,191,888 | A | 3/1993 | Palmer et al. |
| 5,195,507 | A | 3/1993 | Bilweis |
| 5,201,704 | A | 4/1993 | Ray |
| 5,215,105 | A | 6/1993 | Kizelshteyn et al. |
| 5,219,358 | A | 6/1993 | Bendel et al. |
| 5,234,435 | A | 8/1993 | Seagrave, Jr. |
| 5,242,418 | A | 9/1993 | Weinstein |
| 5,250,035 | A | 10/1993 | Smith et al. |
| 5,255,691 | A | 10/1993 | Otten |
| 5,271,415 | A | 12/1993 | Foerster et al. |
| 5,281,218 | A | 1/1994 | Imran |
| 5,284,153 | A | 2/1994 | Raymond et al. |
| 5,284,154 | A | 2/1994 | Raymond et al. |
| 5,300,077 | A | 4/1994 | Howell |
| 5,325,868 | A | 7/1994 | Kimmelstiel |
| 5,341,807 | A | 8/1994 | Nardella |
| 5,351,679 | A | 10/1994 | Mayzels et al. |
| 5,353,784 | A | 10/1994 | Nady-Mohamed |
| 5,353,789 | A | 10/1994 | Schlobohm |
| 5,353,802 | A | 10/1994 | Ollmar |
| 5,360,441 | A | 11/1994 | Otten |
| 5,365,928 | A | 11/1994 | Rhinehart et al. |
| 5,374,261 | A | 12/1994 | Yoon |
| 5,383,879 | A | 1/1995 | Phillips |
| 5,385,146 | A | 1/1995 | Goldreyer |

(56) References Cited

U.S. PATENT DOCUMENTS

| | | |
|---|---|---|
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A * | 3/1998 | Popken .......... A61B 17/14 30/166.3 |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Asum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,887 B1 | 7/2002 | McGuckin et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |

(56) References Cited

U.S. PATENT DOCUMENTS

| | | |
|---|---|---|
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,169,147 B2 | 1/2007 | Nosel |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 7,959,577 B2 | 6/2011 | Schmitz et al. |
| 7,963,915 B2 | 6/2011 | Bleich |
| 8,002,776 B2 * | 8/2011 | Liu .................. A61B 17/1659 606/85 |
| 8,048,080 B2 | 11/2011 | Bleich et al. |

(56) References Cited

U.S. PATENT DOCUMENTS

| | | |
|---|---|---|
| 8,062,298 B2 | 11/2011 | Schmitz et al. |
| 8,062,300 B2 | 11/2011 | Schmitz et al. |
| 8,092,456 B2 | 1/2012 | Bleich et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 8,257,356 B2 | 9/2012 | Bleich et al. |
| 8,303,516 B2 | 11/2012 | Schmitz et al. |
| 8,366,712 B2 | 2/2013 | Bleich et al. |
| 8,394,102 B2 | 3/2013 | Garabedian et al. |
| 8,398,641 B2 | 3/2013 | Wallace et al. |
| 8,409,206 B2 | 4/2013 | Wallace et al. |
| 8,419,653 B2 | 4/2013 | Bleich et al. |
| 8,430,881 B2 | 4/2013 | Bleich et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0128700 A1 | 9/2002 | Cross |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0023190 A1 | 1/2003 | Cox |
| 2003/0045808 A1 | 3/2003 | Kaula et al. |
| 2003/0045937 A1 | 3/2003 | Ginn |
| 2003/0074037 A1 | 4/2003 | Moore et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199159 A1 | 10/2004 | Lee et al. |
| 2004/0199166 A1 | 10/2004 | Schmieding et al. |
| 2004/0225233 A1 | 11/2004 | Frankowski et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1* | 1/2006 | Patel et al. ................ 606/79 |
| 2006/0015035 A1 | 1/2006 | Rock |
| 2006/0025702 A1 | 2/2006 | Sterratino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095026 A1 | 5/2006 | Ricart et al. |
| 2006/0095028 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1* | 9/2006 | Harp .................. A61B 17/1624 606/85 |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |

(56) References Cited

U.S. PATENT DOCUMENTS

| | | |
|---|---|---|
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0168007 A1 | 7/2007 | Kuzma et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213734 A1 | 9/2007 | Bleich et al. |
| 2007/0213795 A1 | 9/2007 | Bradley et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0015582 A1 | 1/2008 | DiPoto et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0182382 A1 | 7/2009 | Justis et al. |
| 2009/0204192 A1 | 8/2009 | Carlton et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0057087 A1 | 3/2010 | Cha |
| 2010/0094231 A1 | 4/2010 | Bleich et al. |
| 2010/0331883 A1 | 12/2010 | Schmitz et al. |
| 2011/0004207 A1 | 1/2011 | Wallace et al. |
| 2011/0046613 A1 | 2/2011 | Schmitz et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat et al. |
| 2011/0224709 A1 | 9/2011 | Bleich |
| 2011/0224710 A1 | 9/2011 | Bleich |
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0184809 A1 | 7/2012 | Bleich et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053851 A1 | 2/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |
| 2014/0074097 A1 | 3/2014 | Schmitz et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO96/22057 A1 | 7/1996 |
| WO | WO97/14362 A1 | 4/1997 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |

(56) References Cited

FOREIGN PATENT DOCUMENTS

| | | |
|---|---|---|
| WO | WO2006/044727 A2 | 4/2006 |
| WO | WO2006/047598 A1 | 5/2006 |
| WO | WO2006/058079 A2 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |
| WO | WO2007/059343 A2 | 2/2007 |
| WO | WO2007/067632 A2 | 6/2007 |
| WO | WO2008/008898 A2 | 1/2008 |
| WO | WO2009/012265 A2 | 1/2009 |
| WO | WO2009/018220 A1 | 2/2009 |
| WO | WO2009/021116 A2 | 2/2009 |
| WO | WO2009/036156 A1 | 3/2009 |
| WO | WO2009/046046 A1 | 4/2009 |
| WO | WO2009/058566 A1 | 5/2009 |
| WO | WO2009/151926 A2 | 12/2009 |
| WO | WO2010/014538 A1 | 4/2010 |

OTHER PUBLICATIONS

Schmitz et al.; U.S. Appl. No. 14/195,197 entitled "Tissue modification devices," filed Mar. 3, 2014.
Leguidleguid et al.; U.S. Appl. No. 14/209,418 entitled "Tissue Modification Devices," filed Mar. 13, 2014.
Abdel-Wanis et al., "Tumor growth potential after tumoral and instrumental contamination: an in-vivo comparative study of T-saw, Gigli saw, and scalpel," Journal of orthopaedic science, Sep. 2001, vol. 6, 424-429.
Barer Malvin, "Instrument to Enhance Passage of the Gigli Saw," Journal of Pediatric Orthopedics, Raven Press, New York, Nov. 1984, 4:762-763.
Baumgart et al., "Indikation and Technik der Knochendurchtrennung," Der Chirurg, Nov. 1998, vol. 69:1188-1196. (in German with Eng Summary).
Bohinski et al., "Novel use of a threadwire saw for high sacral amputation," Journal of neurosurgery: Spine, Jul. 2005, vol. 3(1): 71R78.
Brunori et al., "Celebrating the centennial (1894-1994): Leonardo Gigli and his wire saw," J. Neurosurg, Jun. 1995, 82(6):1086-1090.
Burrows, Harold, "Surgical instruments and appliances used in operations," Faber and Faber, London, Jan. 1937, total pp. 4.
Codman Laminectomy Shaver (a Johnson & Johnson company www.codman.com) catalogue, pp. 416-431, [online] Retrieved from the Internet: <URL: http:IIwww.codman.com/PDFs/Catalog_04_R.pdf>; date of publication unknown; available to applicants at least as of Nov. 22, 2006.
Dammann, Gordon, Pictorial Encyclopedia of Civil War Medical Instruments and Equipment, Pictorial Histories Publishing Company, Missoula, Montana, Apr. 1, 1983, Total pp. 2.
Edwards et al; "T-Saw Laminoplasty for the Management of Cervical Spondylotic Myelopathy," Spine, Lippincott Williams & Wilkins, Inc., Jul. 15, 2000, vol. 25(14): 1788R1794.
Ellman Int. Disc-FX System Accessories K052241 [online] Retrieved from the Internet: <URL: http://www.ellman.com/medical/ >; 1 page; date of publication unknown; available to applicants at least as of Nov. 22, 2006.
Eralp et al., "A comparison of two osteotomy techniques for tibial lengthening," Archives of orthopaedic and trauma surgery, Jun. 2004, vol. 124: pp. 298-300.
Fessler Richard G, "Minimally Invasive Microendoscopic Decompressive Laminotomy for Lumbar Stenosis," American Association of Neurological Surgeons, 2006, Online CME course, 26 pages total, [Retrieved on Jun. 29, 2006 from the internet http://www.aans.emedtrain.com/lumbar_stenosis/lumbarStenosis.swf.

Fujita et al., "Chordoma in the Cervical Spine Managed with En Bloc Excision," Spine, Lippincott Williams & Wilkins, Inc., Sep. 1, 1999, 24 (17):1848-1851.
Goel, Atul, "Neurosurgical forum, Supraorbital Craniotomy," Journal of Neurosurgery, Oct. 1994, vol. 81, 642-643.
Gore Smoother User Manual, W. L. Gore & Associates, Inc. Flagstaff, AZ, Dec. 1999,Total pp. 3.
Hara et al., "En Bloc Laminoplasty Performed with Threadwire Saw: Technical Note," Neurosurgery, Jan. 2001, vol. 48, No. 1, pp. 235-239.
Hata et al; "A less invasive surgery for rotator cuff tear: Mini-open repair," Journal of Shoulder and Elbow Surgery, Jan. 2001, vol. 10 No. 1, 11-16.
Herkowitz, "The Cervical Spine Surgery Atlas", 2004, Lippincott Williams & Wilkins; 2nd Edition; pp. 203-206, & 208; Dec. 2003.
Honl et al; "The Use of Water-Jetting Technology in Prostheses Revision Surgery . . . ," J. Biomed Mater Res (Applied Biomaterials), John Wiley & Sons, Inc, 2000, 53(6): 781-790 (year of pub. is sufficiently earlier than effective U.S. filing date & any foreign priority date).
Integra Ruggles TM Kerrison Rongeurs [online]; Retrieved from the internet: <URL: http://www.integra-Is.com/products!?product=22> on Oct. 17, 2006; 2 pages.
Jun, Byung-Yoon, "Posterior Lumbar Interbody Fusion With Restoration of Lamina and Facet Fusion," Spine, Lippincott Williams & Wilkins, Inc., Apr. 15, 2000, vol. 25, No. 8, pp. 917-922.
Kawahara et al., "Recapping T-Saw Laminoplasty for Spinal Cord Tumors," Spine, Jul. 1, 1999, vol. 24 No. 13, pp. 1363-1370.
Martin-Benlloch et al., "Expansive Laminoplasty as a Method for Managing Cervical Multilevel Spondylotic Myelopathy," Spine, Lippincott Williams & Wilkins, Inc., Apr. 1, 2003, vol. 28, No. 7, pp. 680-684.
Miyamoto et al., "Kyphectomy Using a Surgical Threadwire (T-saw) for Kyphotic Deformity in a Child With Myelomeningocele," Spine, Lippincott Williams & Wilkins, Inc., May 15, 2003, vol. 28, No. 10, pp. E187-E190.
Mopec Bone-Cutting tool, Product brochure; Dec. 15, 2005; Total pp. 4.
Nakagiri et al., "Thoracoscopic Rib Resection Using a Gigli Saw," The Annals of Thoracic Surgery, Aug. 2005, vol. 80, pp. 755-756.
Ohta et al., "Superimposed Mechanomyographic Response at Different Contraction Intensity in Medial Gastrocnemius and Soleus Muscles," International Journal of Sport and Health Science: vol. 5, 63-70, Nov. 2007.
Osaka et al., "Clinical significance of a wide excision policy for sacrococcygeal chordoma," J Cancer Res Clin Oncol, Dec. 16, 2005, Total pp. 6.
Paktiss et al., "Afghan Percutaneous Osteotomy," Journal of Pediatric Orthopaedics, Raven Press Ltd, New York, Jul.-Aug. 1993, vol. 13, No. 4, 531-533.
Paley et al., "Percutaneous Osteotomies," Orthopedic Clinics of North America, Oct. 1991, vol. 22, No. 4, pp. 613-624.
Pancoast, Joseph, "A Treatise on Operative Surgery," Carey and Hart, Philadelphia, (year of publication is sufficiently earlier than the effective U.S. filing date any foreign priority date) 1844, Total pp. 11.
Park et al; "Cases of the Excision of Carious Joints," John Scrymgeour, Glasgow, (year of publication is sufficiently earlier than the effective U.S. filing any foreign priority date) 1806, Total pp. 6.
Peavy et al., "Comparison of Cortical Bone Ablations by Using Infrared Laser Wavelengths 2.9 to 9.2 µm, Lasers in Surgery and Medicine," (year of publication is sufficiently earlier than the effective U.S. filing and any foreign priority date) 1999, vol. 26, pp. 421-434.
Peltier, Leonard Orthopedics: A History and Iconography, Norman Publishing, San Francisco, Feb. 1, 1993, Total pp. 3.
Reckling Frederick, "Modified Stethoscope Earpiece Makes Excellent Gigli Saw Guide," J Bone and Joint Surgery Am, Dec. 1972, 54-A(8), 1787-1788.
Rutkow, Ira, "Surgery: An Illustrated History," Mosby'Year Book, Inc., St. Louis, Oct. 1, 1993, Total pp. 4.

(56) References Cited

OTHER PUBLICATIONS

Schwieger et al., "Abrasive Water Jet Cutting as a New Procedure for Cutting Cancellous Bone'in Vitro Testing in Comparison with the Oscillating Saw," Wiley Interscience, www.interscience,wiley. com, Sep. 20, 2004, pp. 223-228.

Sen et al., The reliability of percutaneous osteotomy with the Gigli saw technique in the proximal tibia;36(2); pp. 136-140; (year of publication is sufficiently earlier than the effective U.S. filing and any foreign priority date) 2002, (Turkish w/ Eng Trans.).

Shiraishi et al., "Results of Skip Laminectomy-Minimum 2-Year Follow-up Study Compared With Open-Door Laminoplasty," Spine, Lippincott Williams & Wilkins, Inc., Dec. 15, 2003, vol. 28, No. 24, pp. 2667-2672.

Shiraishi T., "A new technique for exposure of the cervical spine laminae. Technical note," Journal of neurosurgery. Spine, Jan. 2002, vol. 96(1), 122-126.

Shiraishi T., Skip laminectomy—a new treatment for cervical spondylotic myelopathy, preserving bilateral muscular attachments to the spinous processes: a preliminary report, Spine, Mar.-Apr. 2002, vol. 2(2), pp. 108-115.

Skippen et al., "The Chain Saw R A Scottish Invention," Scottish Medical Journal, May 2004, vol. 49(2), 72-75.

Stevens et al., "Calvarial Bone Graft Harvest Using the Gigli Saw," Journal of Oral and Maxillofacial Surgery, Jun. 1998, vol. 56(6): 798-799.

Takada et al., "Unusual Metastasis to the Cauda Equina From Renal Cell Carcinoma," Spine, Lippincott Williams & Wilkins, Inc; Mar. 15, 2003, vol. 28 No. 6, pp. E114-E117.

Tomita et al., "Expansive Midline T-Saw Laminoplasty (Modified Spinour Process-Splitting) for the Management of Cervical Myelopathy," Spine, Lippincott Williams & Wilkins, Inc; Jan. 1, 1998, 23(1): 32-37.

Tomita et al., "The Threadwire Saw: a New Device for Cutting Bone," The Journal of Bone and Joint Surgery, Dec. 1996, vol. 78(12): 1915-1917.

Tomita et al., "The Use of the T-Saw for Expansive Midline laminoplasty in the Treatment of Cervical Myelopathy," Orthopedics and Traumatology, vol. 10, No. 3, pp. 169-178, Sep. 2002.

Tomita et al., "Total en bloc spondylectomy and circumspinal decompression for solitary spinal metastasis," Paraplegia, Jan. 1994, 32(1):36-46.

Tomita K. et al., "Total en bloc spondylectomy for solitary spinal metastases," International Orthopaedics (SICOT), Oct. 1994, 18(5): 291-298.

Truax, Charles, "The Mechanics of Surgery," Chicago, IL; (year of publication is sufficiently earlier than the effective U.S. filing and any foreign priority date) 1899, Total pp. 3.

US Surgical Kerrison Spinal Rongeur K943116 [online] Retrieved from the internet: <URL: http://www.ussurg.com/uss/index.html> Nov. 22, 2006; 1 page.

Wilkins, Robert H, "Neurosurgical Classics," Johnson Reprint Corporation, New York, (year of publication is sufficiently earlier than the effective U.S. filing and any foreign priority date) 1965, pp. 377-382.

Zeppelin Laminectomy Rongeur K901372, [online] Retrieved from the internet: <URL:http://www.zeppelin-medical.com/download/ instruments.pdf>, Oct. 24, 2006; 1 page.

Schmitz et al.; U.S. Appl. No. 14/023,893 entitled "Tissue Access Guidewire System and Method," filed Sep. 11, 2013.

Leguidleguid et al.; U.S. Appl. No. 14/061,641 entitled "Tissue Modification Devices," filed Oct. 23, 2013.

Schmitz et al.; U.S. Appl. No. 14/064,085 entitled "Access and Tissue Modification Systems and Methods," filed Oct. 25, 2013.

* cited by examiner

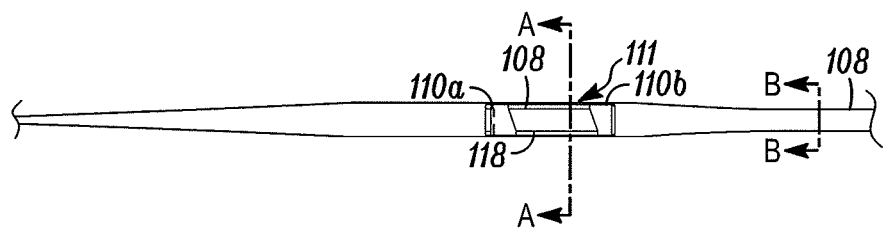
*FIG. 3C*
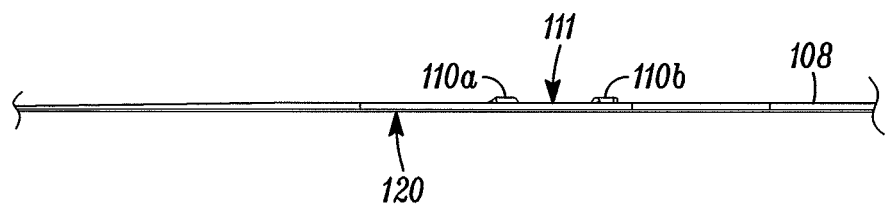
*FIG. 3D*
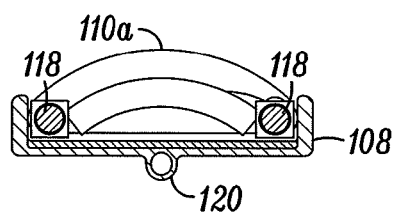 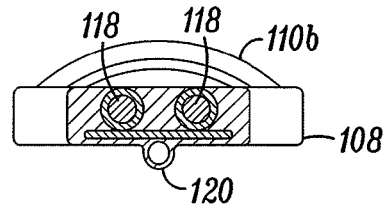
SECTION A-A    SECTION B-B
*FIG. 3E*    *FIG. 3F*

SECTION A-A

SECTION B-B

SECTION B-B

TISSUE REMOVAL
ELEMENT ROTATION

SECTION C-C

SECTION D-D

SECTION E-E

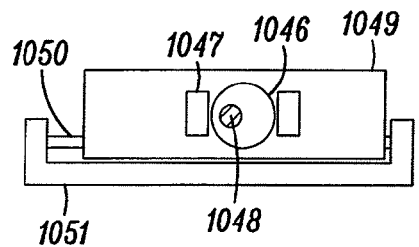
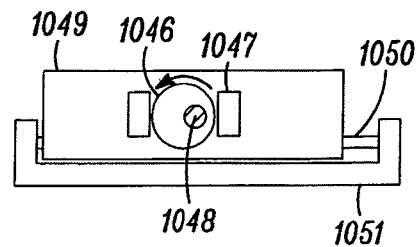
FIG. 56A  FIG. 56B
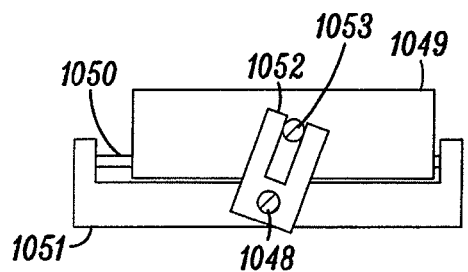
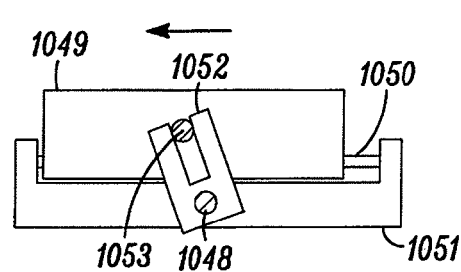
FIG. 57A  FIG. 57B
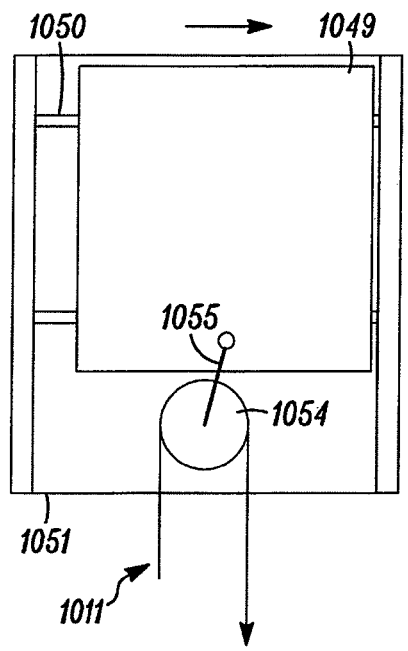
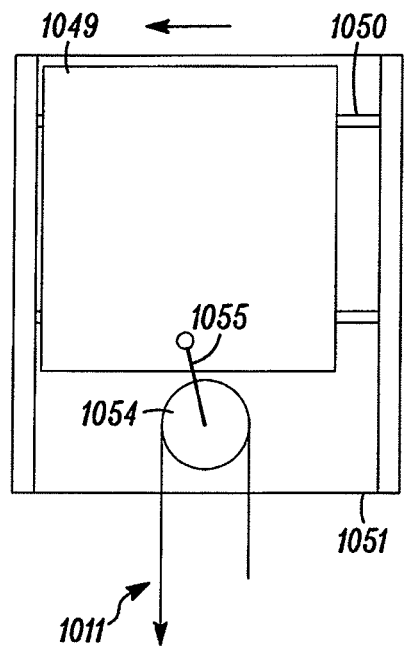
FIG. 58A  FIG. 58B

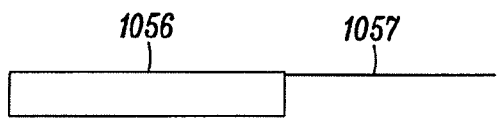 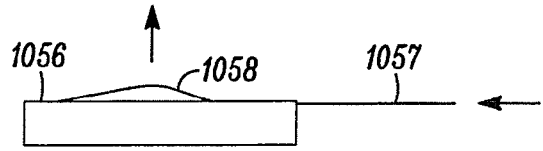
*FIG. 59A*  *FIG. 59B*
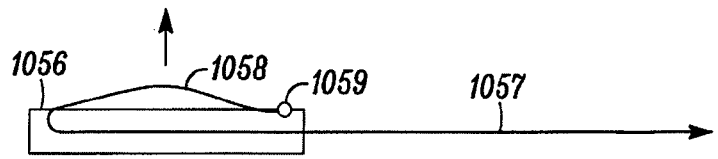
*FIG. 59C*
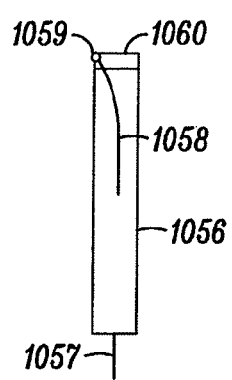 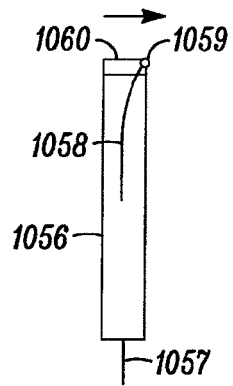
*FIG. 60A*  *FIG. 60B*

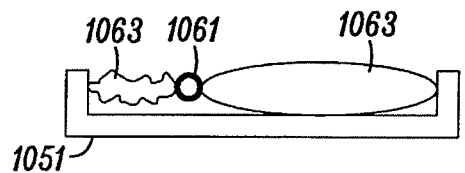
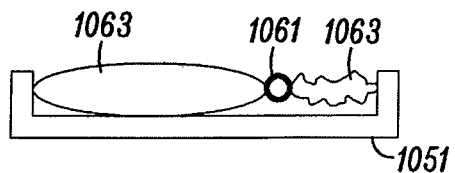
FIG. 64B    FIG. 64C
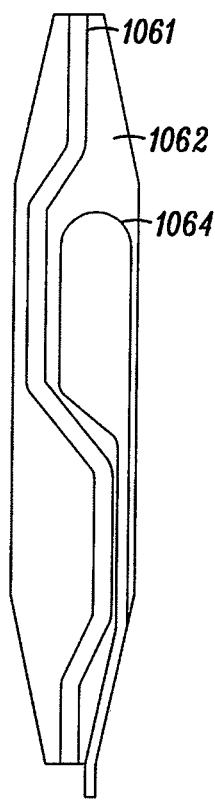
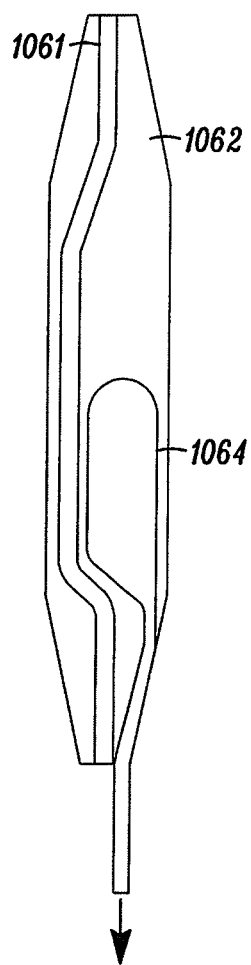
FIG. 65A    FIG. 65B

POWERED TISSUE MODIFICATION DEVICES AND METHODS

CROSS REFERENCE TO RELATED APPLICATIONS

The present application is a continuation of U.S. patent application Ser. No. 13/078,376, entitled "Powered Tissue Modification Devices and Methods," filed Apr. 1, 2011, Publication No. US-2011-0190772-A1, which is a continuation-in-part of U.S. patent application Ser. No. 11/406,486, entitled "Powered Tissue Modification Devices and Methods," filed on Apr. 17, 2006, now U.S. Pat. No. 7,938,830, which is a continuation-in-part of U.S. patent application Ser. No. 11/375,265, entitled "Methods and Apparatus for Tissue Modification," filed on Mar. 13, 2006, now U.S. Pat. No. 7,887,538, which is a continuation-in-part of PCT Patent Application No. PCT/US2005/037136, filed Oct. 15, 2005, Publication No. WO2006/044727, which claims the benefit of: U.S. Provisional Application No. 60/619,306, filed Oct. 15, 2004, U.S. Provisional Application No. 60/622,865, filed Oct. 28, 2004, U.S. Provisional Application No. 60/681,719, filed May 16, 2005, U.S. Provisional Application No. 60/681,864, filed May 16, 2005, and U.S. Provisional Application No. 60/685,190, filed May 27, 2005, each of which is incorporated by reference herein in its entirety.

U.S. patent application Ser. No. 13/078,376 is also a continuation-in-part of U.S. patent application Ser. No. 11/405,848, entitled "Mechanical Tissue Modification Devices and Methods," filed on Apr. 17, 2006, now U.S. Pat. No. 8,430,881, which is a continuation-in-part of U.S. patent application Ser. No. 11/375,265, entitled "Methods and Apparatus for Tissue Modification," filed on Mar. 13, 2006, now U.S. Pat. No. 7,887,538, which is a continuation-in-part of PCT Patent Application No. PCT/US2005/037136, filed Oct. 15, 2005, Publication No. WO2006/044727, which claims the benefit of: U.S. Provisional Application No. 60/619,306, filed Oct. 15, 2004, U.S. Provisional Application No. 60/622,865, filed Oct. 28, 2004, U.S. Provisional Application No. 60/681,719, filed May 16, 2005, U.S. Provisional Application No. 60/681,864, filed May 16, 2005, and U.S. Provisional Application No. 60/685,190, filed May 27, 2005, each of which is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The present invention relates to methods and apparatus for modifying tissue in a patient.

BACKGROUND OF THE INVENTION

Many pathological conditions in the human body may be caused by enlargement, movement, displacement and/or a variety of other changes of bodily tissue, causing the tissue to press against (or "impinge on") one or more otherwise normal tissues or organs. For example, a cancerous tumor may press against an adjacent organ and adversely affect the functioning and/or the health of that organ. In other cases, bony growths (or "bone spurs"), arthritic changes in bone and/or soft tissue, redundant soft tissue, or other hypertrophic bone or soft tissue conditions may impinge on nearby nerve and/or vascular tissues and compromise functioning of one or more nerves, reduce blood flow through a blood vessel, or both. Other examples of tissues which may grow or move to press against adjacent tissues include ligaments, tendons, cysts, cartilage, scar tissue, blood vessels, adipose tissue, tumor, hematoma, and inflammatory tissue.

One specific example of a condition caused by tissue impingement is spinal stenosis. Spinal stenosis occurs when neural tissue and/or vascular tissue in the spine become impinged by one or more structures pressing against them ("neural and/or neurovascular impingement"), causing one or more symptoms. This impingement of tissue may occur in one or more of several different areas in the spine, such as in the central spinal canal (the vertical passage through which the spinal cord and cauda equina extends), the lateral recesses of the spinal canal, or one or more intervertebral foramina (the openings through which nerve roots branching from the spinal cord pass).

For explanatory purposes, FIG. 1 is offered to show an approximate top view of a vertebra (one of the bones of the spinal column) with the cauda equina (the horsetail-shaped bundle of nerves that extends from the base of the spinal cord through the central spinal canal) shown in cross section and two nerve roots exiting the central spinal canal and extending through intervertebral foramina on either side of the vertebra. (FIG. 1 is not drawn to exact scale and is intended for exemplary purposes only. It should be emphasized here that the drawing figures appended to this application are not intended to be precisely anatomically correct and are provided for exemplary purposes to facilitate description.) The spinal cord and cauda equina run vertically along the spine through the central spinal canal, while nerve roots branch off of the spinal cord and cauda equina between adjacent vertebrae and extend through the intervertebral foramina.

One common cause of spinal stenosis is buckling and thickening of the ligamentum flavum (one of the ligaments attached to and connecting the vertebrae), as shown in FIG. 1. Buckling or thickening of the ligamentum flavum may impinge on one or more neurovascular structures, dorsal root ganglia, nerve roots and/or the spinal cord itself. Another common cause of neural and neurovascular compression within the spine is disease of one or more of the intervertebral discs (the malleable discs between adjacent vertebrae), which may lead to collapse, bulging or herniation of the disc. In FIG. 1, an intervertebral disc is shown with three solid-tipped arrows demonstrating how the disc might bulge or herniate into the central spinal canal to impinge upon the spinal cord, cauda equina and/or individual nerve roots. Other causes of neural and neurovascular impingement in the spine include: hypertrophy of one or more facet joints (also known as zygopophaseal joints, facet joints provide articulation between adjacent vertebrae—two vertebral facet superior articular processes are shown in FIG. 1); formation of osteophytes (bony growths or "bone spurs") on vertebrae; spondylolisthesis (sliding of one vertebra relative to an adjacent vertebra); and (facet joint) synovial cysts. Disc, bone, ligament or other tissue may impinge on the spinal cord, the cauda equina, branching spinal nerves and/or blood vessels in the spine to cause loss of function, ischemia (shortage of blood supply) and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stensosis include systemic medications and physical therapy. Epidural steroid injections may also be utilized, but they do not provide ling lasting benefits. When these approaches are inadequate, current treatment for spinal stenosis is generally limited to invasive surgical procedures to remove vertebral ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIG. 1) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints between vertebrae). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments.

While laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for addressing neural and neurovascular impingement in a spine. Ideally, methods and devices for addressing impingement in spine would treat one or more target tissues while preventing unwanted effects on adjacent or nearby non-target tissues. Also ideally, such methods and devices would be minimally invasive and reduce impingement without removing significant amounts of vertebral bone, joint, or other spinal support structures, thereby avoiding the need for spinal fusion and, ideally, reducing the long-term morbidity levels resulting from currently available surgical treatments. It may also be advantageous to have less invasive methods and devices for modifying target tissues in parts of the body other than the spine while preventing modification of non-target tissues. At least some of these objectives will be met by the present invention.

Description of Background Art. Flexible wire saws and chain saws, such as threadwire saws (T-saws) and Gigli saws, have been used since the late 1800s to saw through or file/abrade bone and other tissue in the human body. See, for example, Brunori A et al., "Celebrating the Centenial (1894-1994): Leonardo Gigli and His Wire Saw," J Neurosurg 82:1086-1090, 1995. An example of one such saw is described in U.S. Pat. No. 8250, issued to P. A. Stohlmann on Nov. 28, 1876. A description of using a T-saw to cut vertebral bone is provided in Kawahara N et al., "Recapping T-Saw Laminoplasty for Spinal Cord Tumors," SPINE Volume 24, Number 13, pp. 1363-1370.

A method and apparatus for treating spinal stenosis is described in PCT Patent Application Pub. No. WO 01/08571. A surgical instrument for removing cartilage from a knee cavity is described in U.S. Pat. No. 3,835,859.

SUMMARY OF THE INVENTION

In various embodiments, the present invention provides methods, apparatus and systems for modifying tissue in a patient. Generally, the methods, apparatus and systems may involve using an elongate, at least partially flexible tissue modification device having one or more tissue modifying members to modify one or more target tissues. The tissue modification device may be configured such that when the tissue modification member (or members) is in a position for modifying target tissue, one or more sides, surfaces or portions of the tissue modification device configured to avoid or prevent damage to non-target tissue will face non-target tissue. In various embodiments, during a tissue modification procedure, an anchoring force may be applied at or near either a distal portion or a proximal portion of the tissue modification device, either inside or outside the patient. Pulling or tensioning force may also be applied to the unanchored end of the device to urge the tissue modifying member(s) against target tissue. The tissue modifying members may then be activated to modify tissue while being prevented from extending significantly beyond the target tissue in a proximal or distal direction. In some embodiments, the tissue modifying members may be generally disposed along a length of the tissue modification device that approximates a length of target tissue to be modified.

By "applying an anchoring force," it is meant that a force is applied to maintain a portion of a device, or the device as a whole, substantially stable or motion-free. Applying an anchoring force is, therefore, not limited to preventing all movement of a device, and in fact, a device to which an anchoring force is applied may actually move in one or more directions in some embodiments. In other embodiments, an anchoring force is applied to maintain a portion of a device substantially stable, while another portion of the device is allowed to move more freely. As will be described in further detail below, applying an anchoring force in one embodiment involves a user of a device grasping the device at or near one of its ends. In other embodiments, devices may use one or more anchoring members to apply an anchoring force. In a number of embodiments, an anchoring force may be applied with or against one or more tissues of a patient's body, and the tissue(s) may often move even as they apply (or help apply) the force. Thus, again, applying an anchoring force to a device does not necessarily mean that all motion of the device is eliminated. Of course, in some embodiments, it may be possible and desirable to eliminate all movement or substantially all movement of a device (or portion of a device), and in some embodiments anchoring force may be used to do so.

Methods, apparatus and systems of aspects of the present invention generally provide for tissue modification while preventing unwanted modification of, or damage to, surrounding tissues. Tensioning the tissue modification device by applying anchoring force at or near one end and applying tensioning or pulling force at or near the opposite end may enhance the ability of tissue modification members of the device to work effectively within a limited treatment space. Applying tensioning force to a predominantly flexible device may also allow the device to have a relatively small profile, thus facilitating its use in less invasive procedures and in other procedures in which alternative approaches to target tissue may be advantageous.

In some embodiments, the described methods, apparatus and systems may be used to modify tissue in a spine, such as for treating neural impingement, neurovascular impingement and/or spinal stenosis. In alternative embodiments, target tissues in other parts of the body may be modified.

In one aspect of the present invention, a device for modifying tissue in a spine may include one or more of the following: a shaft having a proximal portion and a distal portion, the distal portion having dimensions which allow it to be passed into an epidural space of the spine and between target and non-target tissues; at least one distal force application member extending from the distal portion of the shaft and configured to facilitate application of at least one of anchoring force and tensioning force to the shaft; at least one movable tissue modifying member coupled with the shaft at or near its distal portion; at least one drive member coupled with the at least one tissue modifying member to activate the at least one tissue modifying member; and at least one power transmission member coupled with the at least one drive member to deliver power to the at least one drive member.

In another aspect of the present invention, a device for modifying tissue in a patient may include: an elongate, at least partially flexible body having a proximal portion and a distal portion, the distal portion having dimensions which allow it to be passed between target and non-target tissues in the patient; at least one distal force application member extending from the distal portion of the elongate body and configured to facilitate application of at least one of anchoring force and tensioning force to the elongate body; at least one proximal force application member coupled with the elongate body at or near the proximal portion and configured to facilitate application of tensioning force to the elongate body; at least one movable tissue modifying member coupled with the elongate body; at least one drive member coupled with the at least one tissue modifying member to activate the at least one tissue modifying member; and at least one power transmission member coupled with the at least one drive member to deliver power to the at least one drive member.

In another aspect of the present invention, a method for modifying tissue in a spine may include one or more of the following steps: passing a distal portion of a tissue modification device into an epidural space of a spine and between one or more target tissues and one or more non-target tissues; positioning at least one tissue modifying member of the tissue modification device adjacent the target tissue such that the tissue modifying member(s) face the target tissue and do not face the non-target tissue; applying at least one of anchoring force and tensioning force at or near the distal portion and at or near a proximal portion of the tissue modification device to urge the at least one tissue modifying member against the target tissue; and transmitting power to at least one drive member coupled with the at least one tissue modifying member to activate the tissue modifying member(s) and thus modify the target tissue.

In one aspect of the present invention, a device for modifying one or more tissues in a patient's spine may include: an elongate, at least partially flexible body having a proximal portion and a distal portion, wherein at least the distal portion has dimensions that allow it to be passed into an epidural space and between target and non-target tissues of the spine; at least one movable blade disposed along one side of the elongate body; at least one actuator coupled with the at least one blade and disposed at or near the proximal or distal portion of the body for moving the blade(s) to modify one or more target tissues, wherein the at least one actuator is configured to move the blade(s) without significantly translating the elongate body proximally or distally; and means at or near the proximal and distal portions of the elongate body for facilitating application of at least one of anchoring force and tensioning force to the body to urge the at least one blade against the target tissue.

In another aspect of the present invention, a device for modifying one or more tissues in a patient may include: an elongate, flexible body having a proximal portion and a distal portion; at least one blade disposed along one side of the elongate body; and means at or near the proximal and distal portions of the elongate body for facilitating application of at least one of anchoring force and tensioning force to the body to urge the at least one blade against the target tissue.

In another aspect of the present invention, a method for modifying tissue in a patient may involve: advancing at least a distal portion of at least one elongate, at least partially flexible tissue modification device into a patient and between one or more target tissues and one or more non-target tissues; positioning at least one blade of the tissue modification device adjacent the target tissue such that the blade(s) face the target tissue and do not face the non-target tissue; applying at least one of anchoring and tensioning force to the tissue modification device at or near its proximal and distal portions to urge the blade(s) against the target tissue; and moving the at least one blade to cut the target tissue.

These and other aspects and embodiments are described more fully below in the Detailed Description, with reference to the attached Drawings.

BRIEF DESCRIPTION OF THE DRAWINGS

FIG. 3C is a top view of the portion shown in FIG. 3B;

FIG. 3D is a side view of the portion shown in FIGS. 3B and 3C;

FIGS. 3E and 3F are cross-sectional views of a portion of the tissue modification device taken through lines A-A and B-B, respectively, shown in FIG. 3C;

FIGS. 56A and 56B are end-on views of a blade mechanism allowing for lateral movement of one or more blades according to one embodiment of the present invention.

FIGS. 57A and 57B are end-on views of a blade mechanism allowing for lateral movement of one or more blades according to an alternative embodiment of the present invention.

FIGS. 58A and 58B are top views of a blade mechanism allowing for lateral movement of one or more blades according to an alternative embodiment of the present invention.

FIGS. 59A-59C are top views of a portion of a tissue modification device including a side wire for facilitating guiding of the portion according to one embodiment of the present invention.

FIGS. 60A and 60B are top views of a portion of a tissue modification device including side wires for facilitating guiding of the portion according to an alternative embodiment of the present invention.

FIGS. 64A-64C are end-on views of a portion of a tissue modification device including expandable bladders for facilitating guiding of the portion according to an alternative embodiment of the present invention.

FIGS. 65A and 65B are top views of a portion of a tissue modification device including a track and deflecting member for facilitating guiding of the portion according to an alternative embodiment of the present invention.

DETAILED DESCRIPTION OF THE INVENTION

Methods, apparatus and systems for modifying tissue in a patient are provided. Although the following description and accompanying drawing figures generally focus on tissue modification in spine, in various alternative embodiments any of a number of tissues in any of a number of anatomical locations in a patient may be modified.

Figure 1:
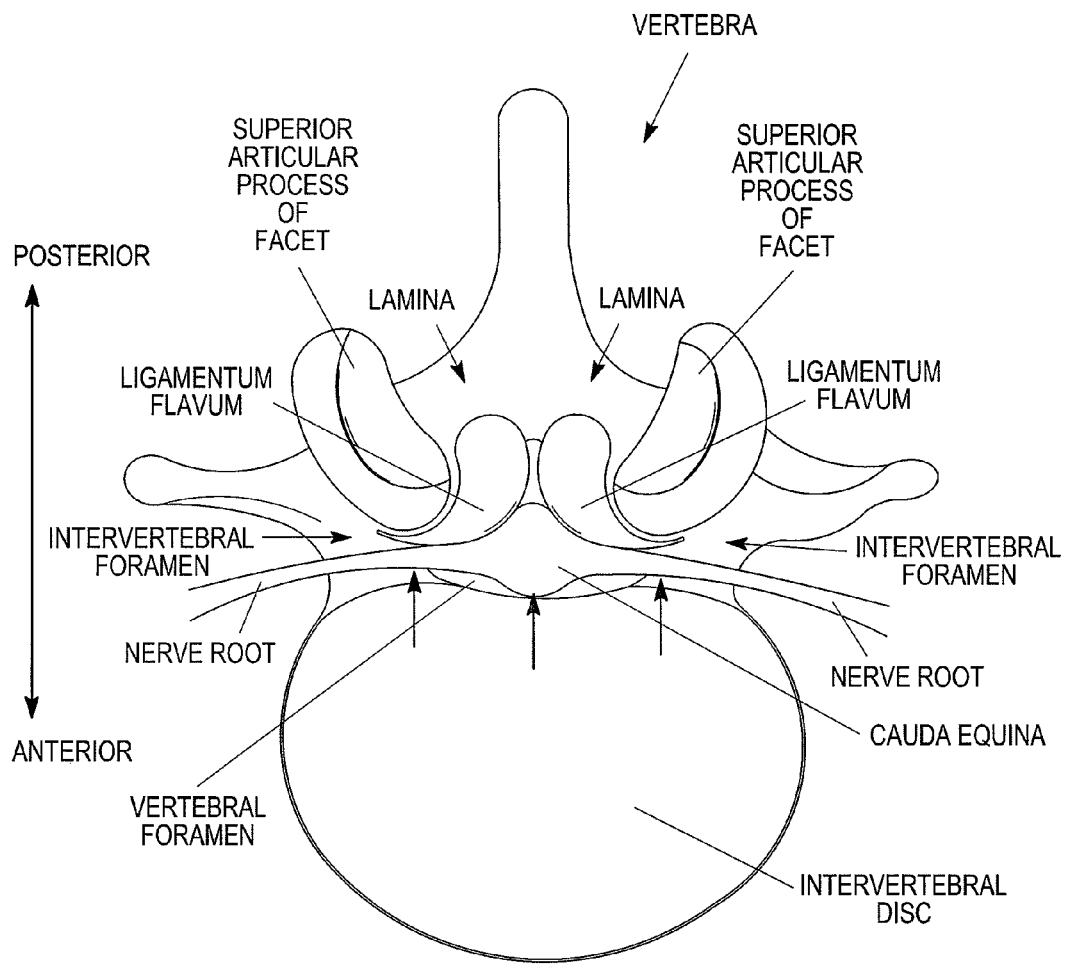
FIG. 1 is cross-sectional view of a spine, showing a top view of a lumbar vertebra, a cross-sectional view of the cauda equina, and two exiting nerve roots.
Figure 2:
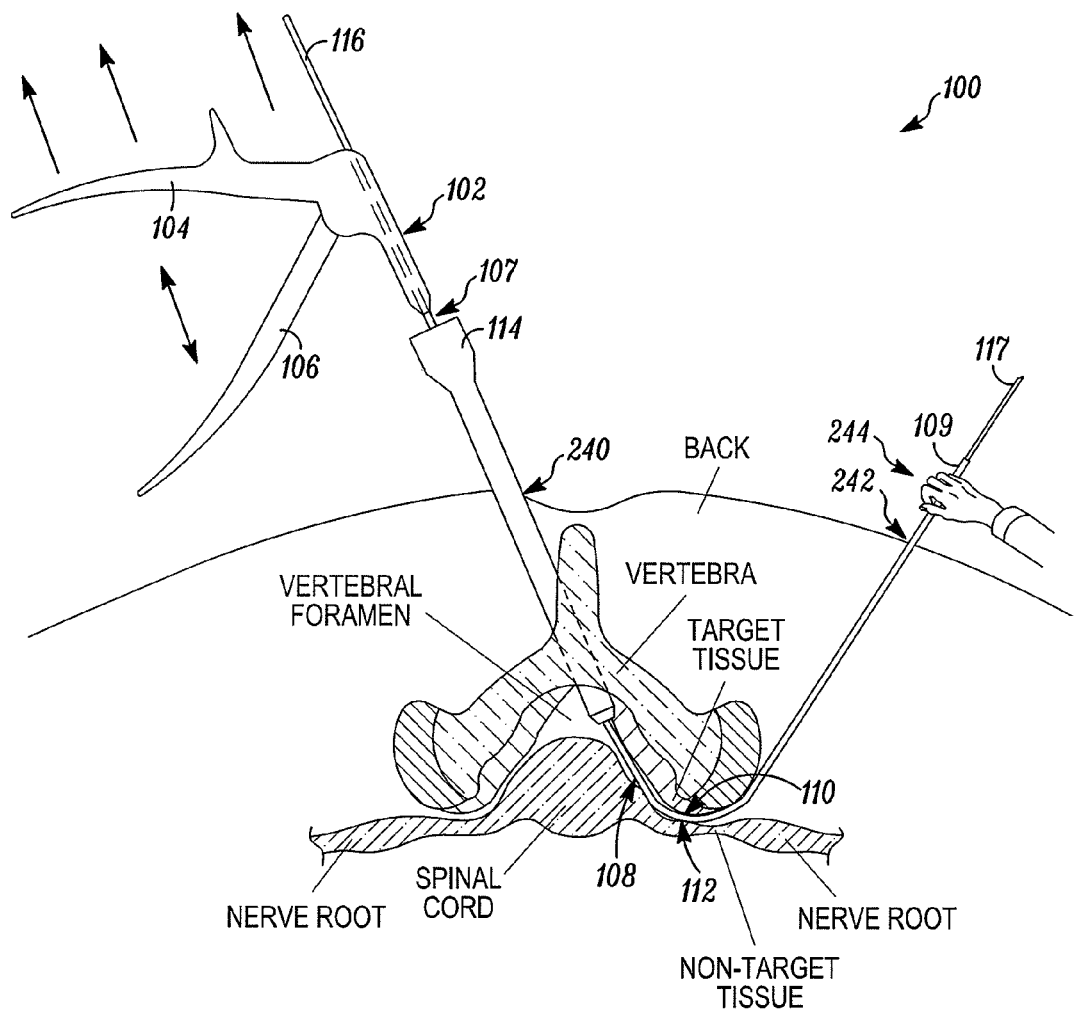
FIG. 2 is a cross-sectional view of a portion of a patient's back and spine, showing part of a vertebra and apparatus in place for modifying tissue according to one embodiment of the present invention.

Referring to FIG. 2, in one embodiment a tissue modification device 102 may include an elongate body 108 having a proximal portion 107 and a distal portion 109, a handle 104 with an actuator 106 coupled with proximal portion 107, one or more tissue modifying members 110, and one or more protective surfaces 112. In various embodiments, some of which are described further below, modification device 102 may be introduced into an area for performing a treatment, such as a spine, using any of a number of different introduction methods, devices and systems. In FIG. 2, for example, modification device 102 extends through an introducer device 114 placed through a first incision 240 on the patient's back and into the central spinal canal. Modification device 102 is advanced along a guide member 116, which extends through introducer member 114, through the intervertebral foramen between two adjacent vertebrae (only part of one vertebra is shown in FIG. 2), and out a second (or "distal") incision 242 on the back. In some embodiments, as shown, guide member has a beveled distal tip 117 for facilitating advancement of guide member 116 through tissue.

Generally, tissue modification device 102 may be advanced to a position in the spine such that tissue modifying member 110 faces target tissue to be modified, such as buckled, thickened or otherwise impinging ligamentum flavum tissue as shown in FIG. 2. Modification device 102 is configured such that when tissue modifying member 110 faces the target tissue, protective surface(s) 112 face non-target tissue. Protective surface 112 may be simply a length of elongate body 108 or may have one or more protective features, such as a widened diameter, protective or lubricious coating, extendable barrier, drug-eluting coating or ports, or the like. In some instances, protective surface(s) 112 may act as "non-tissue-modifying" surfaces, in that they may not substantially modify the non-target tissue. In alternative embodiments, protective surface(s) 112 may affect non-target tissue by protecting it in some active way, such as by administering one or more protective drugs, applying one or more forms of energy, providing a physical barrier, or the like.

In some embodiments, once tissue modification device 102 is positioned such that tissue modifying member 110 faces target tissue and protective surface 112 faces non-target tissue, an anchoring force may be applied at or near distal portion 109 of elongate body 108, either inside or outside the patient's body. A tensioning force may also be applied at or near proximal portion 107 of elongate body 108, such as by pulling on handle 104 (one-directional arrows), and actuator 106 may be used (two-headed arrow) to activate tissue modifying member(s) 110 to modify target tissue. In the example shown, anchoring force is applied near distal portion 109 by a user's hand 244, and handle 104 is pulled proximally (arrows) to apply tensioning force. In an alternative embodiment, hand 244 may grasp guide member 116 at or near its distal portion 117 and thus apply anchoring force to it, thus also applying anchoring force to elongate body 108. In one variation of such an embodiment, elongate body 108 or handle 104 may optionally be adjustably clamped to guide member 116 to further enhance or facilitate application of anchoring force to elongate body 108. Tissue modification via tissue modifying members 110 may include cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting the target tissue. Once tissue has been modified, tissue modification device 102 and any introducer devices 114, guide members 116 or other devices may be removed from the patient.

In various embodiments of the apparatus, tissue modifying member(s) 110 may be disposed along any suitable length of body 108. In one embodiment, for example, such as an embodiment of the device to be used in a spinal treatment, tissue modifying members 110 may be disposed along a length of the device measuring no longer than 10 cm, and preferably no more than 6 cm, and even more preferably no more than 3 cm. In various embodiments, tissue modifying member(s) 110 may include a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode, a rotary powered mechanical shaver, a reciprocating powered mechanical shaver, a powered mechanical burr, a laser, an ultrasound crystal, a cryogenic probe, a pressurized water jet, a drug dispensing element, a needle, a needle electrode, or some combination thereof. In various embodiments, all tissue modifying members 110 may be mobile relative to the elongate body, all may be static, or some may be mobile and some may be static. These and other aspects and embodiments are described further below.

Figure 3A:
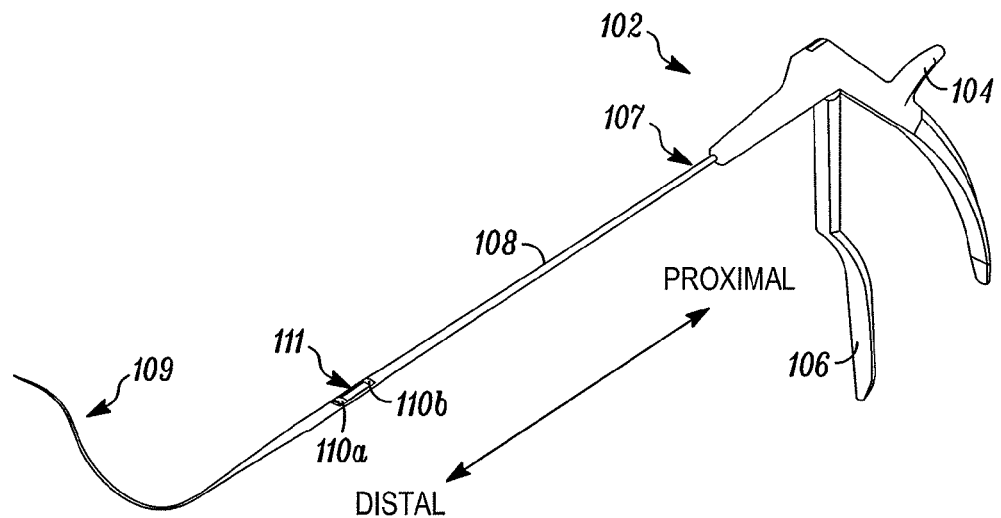
FIG. 3A is a perspective view of a tissue modification device according to one embodiment of the present invention.

Turning now to FIGS. 3A-3I, more detailed figures of one embodiment of tissue modification device 102 are shown. Referring to FIG. 3A, tissue modification device 102 may include elongate body 108 having proximal portion 107 and distal portion 109, a window 111 disposed along elongate body 108, two tissue modifying blades 110 exposed through window 111, and handle 104 with actuator 106 coupled with proximal portion 107. In the embodiment shown, the tissue modifying members comprise blades 110, although in alternative embodiments other tissue modifying members may be added or substituted.

In various embodiments, elongate body 108 may have any number of dimensions, shapes, profiles and amounts of flexibility. For example, distal portion 109 is shown having a curved shape to demonstrate that at least a portion of elongate body 108 may be flexible. In various embodiments, elongate body 108 may have one or more of a round, ovoid, ellipsoid, flat, cambered flat, rectangular, square, triangular, symmetric or asymmetric cross-sectional shape. As shown in FIGS. 3C and 3D, in the pictured embodiment, elongate body 108 has a relatively flat configuration, which may facilitate placement of body 108 between target and non-target tissues. Distal portion 109 of body 108 may be tapered, to facilitate its passage into or through narrow spaces as well as through small incisions on a patient's skin. Body 108 may also include a slightly widened portion around the area of window 111 and blades. In one embodiment, such as an embodiment used for modifying tissue in a spine, body 108 may have a small profile, such as having a height of not more than 10 mm at any point along its length and a width of not more than 20 mm at any point along its length, or more preferably a height not more than 5 mm at any point along its length and a width of not more than 10 mm at any point along its length, or even more preferably a height not more than 2 mm at any point along its length and a width of not more than 4 mm at any point along its length. Body 108 may be long enough to extend through a first incision on a patient, between target and non-target tissue, and out a second incision on a patient. Alternatively, body 108 may be long enough to extend through a first incision, between the target and non-target tissue, and to an anchoring location within the patient. In another alternative embodiment, body 108 may be long enough to extend through a first incision, between the target and non-target tissue, to a location nearby but distal to the target tissue within the patient, with some portion of tissue modification device 102 anchored to guide member 116. In some embodiments, elongate body 108 includes at least one feature for allowing passage of the body over a guidewire or other guide member or to allow passage of one or more guide members over or through body 108. For example, in various embodiments body 108 may include one or more guidewire lumens, rails, tracks, lengthwise impressions or some combination thereof.

In one embodiment, elongate body 108 is predominantly flexible along its length and comprises any suitable flexible material, such as thin, flexible metals, plastics, fabrics or the like. In some embodiments, it may be advantageous to include one or more rigid sections in elongate body 108, such as to impart pushability to a portion of body 108 or to facilitate application of force to tissue modification members 110 without causing unwanted bending or kinking of elongate body 108. In such embodiments, rigidity may be conferred by using additional materials in body 108 or by making the rigid portions thicker or wider or of a different shape.

Handle 104 may have any suitable configuration according to various embodiments. Similarly, actuator 106 may include any of a number of actuation devices in various embodiments. In the embodiment shown in FIG. 3A, actuator 106 comprises a trigger or moving handle portion, which is grasped by a user and pulled or squeezed toward handle 104 to bring blades 110 together to cut tissue. In an alternative embodiment, actuator 106 instead may include a switch or button for activating a radiofrequency surgical ablation tissue modifying member. In yet another embodiment, actuator 106 may include a combination trigger and switch, one or more pull wires, any suitable form of lever and/or some combination thereof.

Figure 3B:
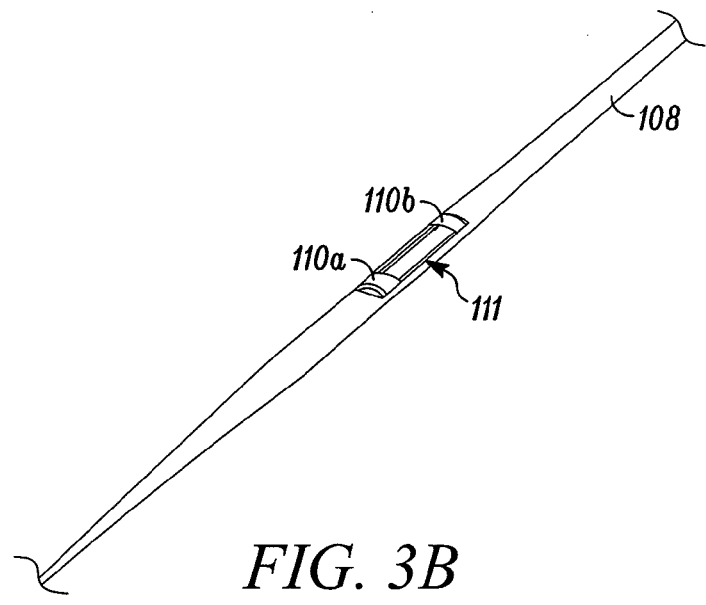
FIG. 3B is a perspective view of a portion of the tissue modification device of FIG. 3A.

FIGS. 3B-3D show in greater detail a portion of tissue modification device 102. In these figures, window 111 and blades 110 are more clearly seen. In one embodiment, at least a portion of elongate body 108 and blades 110 may have a slightly curved configuration. In alternative embodiments, at least a portion of elongate body 108 and blades 110 may be flat. In other alternative embodiments, tissue modification members such as blades 110 may be proud to elongate body 108.

Blades 110 include a distal 110a and a proximal blade 110b that reside at the distal and proximal edges, respectively, of window 111 of elongate body 108. Window 111 of body 108 may accommodate both soft and hard tissue when the device is forcibly applied to the surface of a target tissue site. The top view of the distal portion of elongate body 108, shown in FIG. 3C, depicts the angled edges of distal blade 110a and proximal blade 110b, which facilitate shearing of target tissue. In alternative embodiments, blades 110 may have any of a number of alternative shapes and configurations. The distal portion of body 108 may have a very low profile (height compared to width), as shown in side view FIG. 3D, where only blades 110 protrude from the top surface of the elongate body 108. In one embodiment, also as shown in FIG. 3D, a guidewire tube 120 (or lumen) may extend from (or be coupled with) a lower surface of elongate body 108. The lower surface of elongate body 108 is an example of a protective or non-tissue-modifying surface.

In one embodiment, distal blade 110a is coupled with two pull-wires 118, as seen in FIGS. 3C, 3E and 3F. Pull-wires 118 coupled to and translated by actuator 106 on handle 104 may be used to drive distal blade 110a proximally to contact the cutting edge of proximal blade 110b, thus cutting tissue. Other alternative mechanisms for driving blades 110, such as gears, ribbons or belts, magnets, electrically powered, shape memory alloy, electro magnetic solenoids and/or the like, coupled to suitable actuators, may be used in alternative embodiments. As mentioned, in one embodiment distal blade 110a and/or proximal blade 110b may have an outwardly curvilinear shape along its cutting edge. Alternatively, distal blade 110a may have a different blade shape, including flat, rectilinear, v-shaped, and inwardly curvilinear (concave vs. convex). The cutting edge of either blade 110 may have a sharp edge formed by a simple bevel or chamfer. Alternatively or in addition, a cutting edge may have tooth-like elements that interlock with a cutting edge of an opposing blade, or may have corrugated ridges, serrations, rasp-like features, or the like. In various embodiments, both blades 110 may be of equal sharpness, or alternatively one blade 110 may be sharp and the other substantially flat to provide a surface against which the sharp blade 110 may cut. Alternately or in addition, both cutting edges may be equally hard, or a first cutting edge may be harder than a second, the latter of which deflects under force from the first harder edge to facilitate shearing of the target tissue.

FIGS. 3E and 3F show cross-sectional views through elongate body at lines A-A and B-B, respectively, of FIG. 3C. In some embodiments, all or a portion of elongate body 108, such as the lower surface shown in FIG. 3E, may include a lubricious surface for facilitating manipulation of the tool in the surgical space and at the anatomical site. The lubricious lower surface also provides a barrier between blades 110 and non-target tissue in the surgical space. The lower surface may include a guide member lumen 120 to accommodate a guidewire or other access device or rail. FIG. 3E shows distal blade 110 coupled with pull wires 118. FIG. 3F shows proximal blade 110b, which is not coupled with pull wires 118 but rather fixed to body 108. In various alternative embodiments, proximal blade 110b may be movable distally while distal blade 110a is static, both blades may be moved toward one another, or a different number of blades may be used, such as one blade drawn toward a backstop or more than two blades, one or more of which may be mobile. In various alternative embodiments, guide member lumen 120 may be accommodated on a side surface or more centrally within elongate body 108. In further alternative embodiments, the one or more guide member lumens 120 may comprise one or more various cross sectional shapes, for example substantially round, substantially oval, or substantially rectabular, to accommodate alternative guide members, for example flat or rectangular guidewires, needles or rails. In still other alternative embodiments guide member lumen 120 may be adjustably coupled with the elongate body 108 to enable manipulation of the location of the elongate body 108 and therefore the tissue modifying members 110 relative to the guiding member.

Figure 3G:
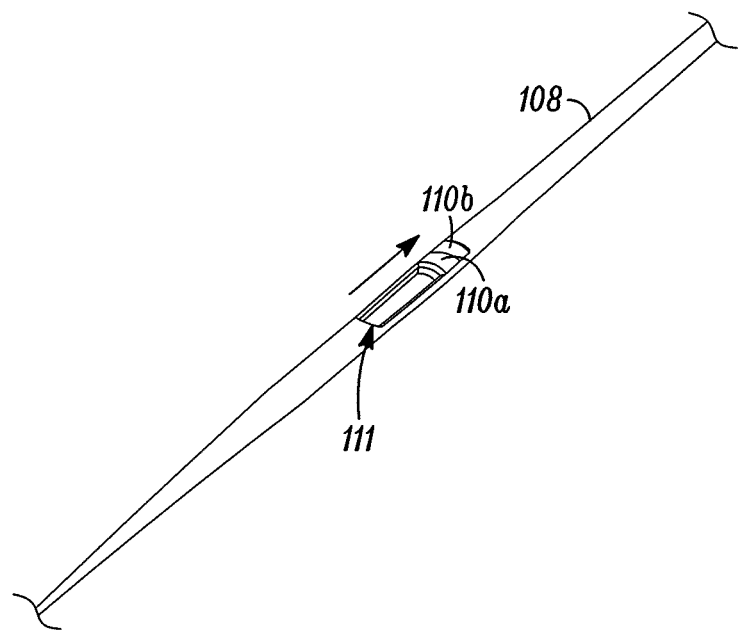
FIG. 3G is a perspective view of a portion of the tissue modification device of FIGS. 3B-3F, shown with a blade of the device in a closed position according to one embodiment of the present invention.
Figure 3H:
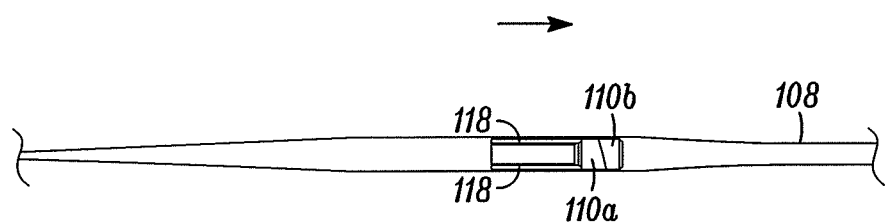
FIG. 3H is a top view of the portion shown in FIG. 3G.
Figure 3I:
FIG. 3I is a side view of the portion shown in FIGS. 3G and 3H.

Referring now to FIGS. 3G-3I, blades 110 are shown in their closed position. In one embodiment, when distal blade 110a is drawn proximally to cut tissue, at least some of the cut tissue is captured in a hollow interior portion of elongate body 108. Various embodiments may further include a cover, a cut tissue housing portion and/or the like for collecting cut tissue and/or other tissue debris. Such collected tissue and debris may then be removed from the patient during or after a tissue modification procedure. During a given tissue modification procedure, distal blade 110a may be drawn proximally to cut tissue, allowed to retract distally, and drawn proximally again to further cut tissue as many times as desired to achieve a desired amount of tissue cutting.

Blades 110 may be made from any suitable metal, polymer, ceramic, or combination thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). In some embodiments, materials for the blades or for portions or coatings of the blades may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In various embodiments, blades 110 may be manufactured using metal injection molding (MIM), CNC machining, injection molding, grinding and/or the like. Pull wires 118 be made from metal or polymer and may have circular, oval, rectangular, square or braided cross-sections. In some embodiments, a diameter of a pull wire 118 may range from about 0.001"-0.050," and more preferably from about 0.010"-0.020".

Depending on the tissue to be treated or modified, activating blades 110 (or other tissue modifying members in alternative embodiments) may cause them to modify target tissue along an area having any of a number of suitable lengths. In use, it may also be advantageous to limit the extent of action of blades 110 or other tissue modifying members to a desired length of tissue, thus not allowing blades 110 to affect tissue beyond that length. In so limiting the effect of blades, unwanted modification of, or damage to, surrounding tissues and structures may be limited or even eliminated. In one embodiment, for example, where the tissue modification device is used to modify tissue in a spine, blades 110 may operate along a length of target tissue of no more than 10 cm, and preferably no more than 6 cm, and even more preferably no more than 3 cm. Of course, in other parts of the body and to address other tissues, different tissue modification devices may be used and tissue modifying members may have many different lengths of activity. In one embodiment, to facilitate proper location of tissue modifying members, such as blades 110, relative to target tissue, the tissue modifying members and/or the elongate body and/or one or more additional features intended for just such a purpose may be composed of a material readily identifiable via x-ray, fluoroscopic, magnetic resonance or ultrasound imaging techniques.

In various embodiments, a number of different techniques may be used to prevent blades 110 (or other tissue modifying members) from extending significantly beyond the target tissue. In one embodiment, for example, preventing blades 110 from extending significantly beyond the target tissue involves holding tissue modification device 102 as a whole predominantly stable to prevent device 102 from translating in a direction toward its proximal portion or toward its distal portion while activating blades 110. Holding device 102 stable is achieved by anchoring one end of the device and applying tensioning force at or near the other end, as described further below.

In the embodiment shown in FIGS. 3A-3I, pull wires 118 are retracted proximally by squeezing actuator 106 proximally. In an alternative embodiment, squeezing actuator 106 may cause both blades 110 to translate inward so that they meet approximately in the middle of window 111. In a further embodiment, distal blade 110a may be returned to its starting position by a pulling force generated from the distal end of device 102, for example by using a distal actuator that is attached to distal wires, or by pulling on the distal guide member which is attached to distal blade 110a. In yet another alternative embodiment, proximal blade 110b may be moved to cut by a pulling force generated from the distal end of device 102, for example by using a distal actuator that is attached to distal wires, or by pulling on the distal guide member which is attached to proximal blade 110b. In yet another embodiment, squeezing actuator 106 may cause proximal blade 110b to move distally while distal blade 110a stays fixed. In other alternative embodiments, one or more blades 110 may move side-to-side, one or more blades 110 may pop, slide or bow up out of window 111 when activated, or one or more blades 110 may expand through window. In another embodiment, one or more blades 110 and/or other tissue modifying members of device 102 may be powered devices configured to cut, shave, grind, abrade and/or resect target tissue. In other embodiments, one or more blades may be coupled with an energy transmission device, such as a radiofrequency (RF) or thermal resistive device, to provide energy to blade(s) 110 for cutting, ablating, shrinking, dissecting, coagulating or heating and thus enhancing tissue modification. In another embodiment, a rasp or file may be used in conjunction with or coupled with one or more blades. In any of these embodiments, use of actuator 106 and one or more moving blades 110 provides for tissue modification with relatively little overall translation or other movement of tissue modification device 102. Thus, target tissue may be modified without extending blades 110 or other tissue modification members significantly beyond an area of target tissue to be treated.

Figure 4A:
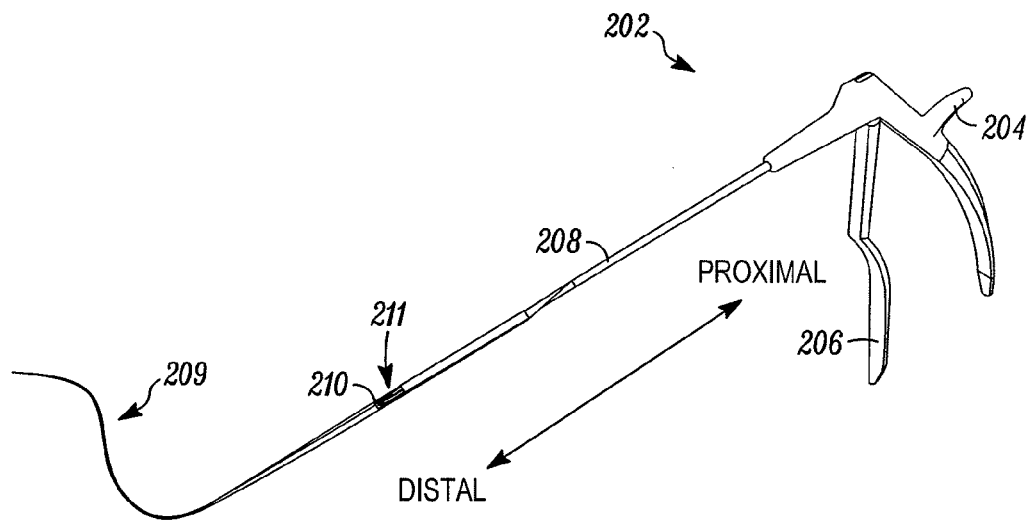
FIG. 4A is a perspective view of a tissue modification device according to one embodiment of the present invention.
Figure 4B:
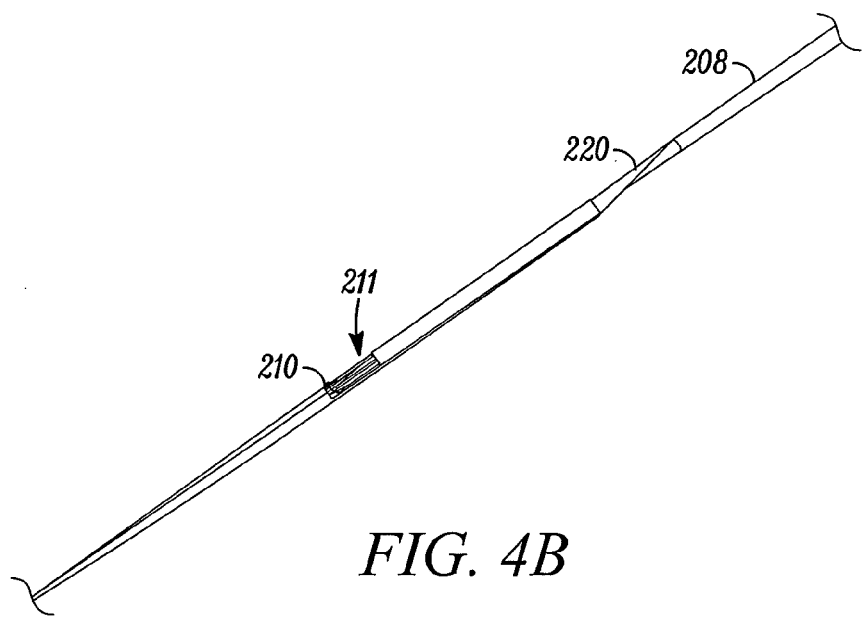
FIG. 4B is a perspective view of a portion of the tissue modification device of FIG. 4A.
Figure 4C:
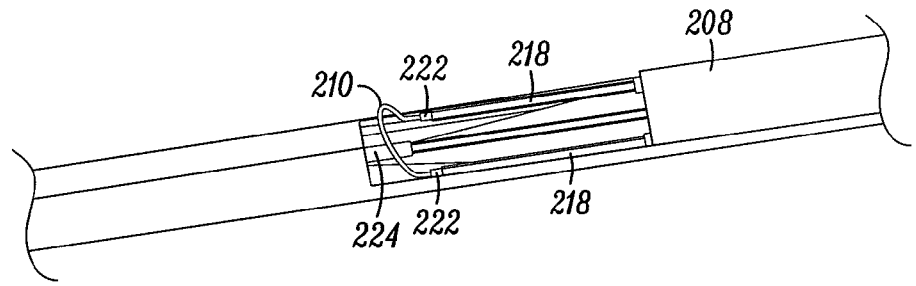
FIG. 4C is a close-up, perspective view of a portion of the tissue modification device of FIGS. 4A and 4B, showing a tissue modifying member according to one embodiment of the present invention.

Referring now to FIGS. 4A-4C, in an alternative embodiment, a tissue modification device 202 may include an elongate body 208 having a proximal portion and a distal portion 209, a handle 204 and actuator 206 coupled with proximal portion, and a window 211 and tissue modifying member 210 disposed near distal portion 209. As seen more clearly in FIGS. 4B and 4C, in the embodiment shown, tissue modifying member 210 comprises an RF electrode wire loop. Wire loop 210 may comprise any suitable RF electrode, such as those commonly used and known in the electrosurgical arts, and may be powered by an internal or external RF generator, such as the RF generators provided by Gyrus Medical, Inc. (Maple Grove, Minn.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Distal portion 209 includes a tapered tip, similar to that described above, to facilitate passage of elongate body 208 into narrow anatomical sites. Handle 204 and actuator 206 are similar to those described above, although in the embodiment of FIGS. 4A-4C, actuator 206 may be used to change the diameter of the wire loop 210. Using actuator 206, wire loop 210 may be caused to extend out of window 211, expand, retract, translate and/or the like. Some embodiments may optionally include a second actuator (not shown), such as a foot switch for activating an RF generator to delivery RF current to an electrode.

Elongate body 208 may be fabricated from any suitable material and have any of a number of configurations. In one embodiment, body 208 comprises a metal tube with a full-thickness slit (to unfold the tube into a flat form—not shown) or stiffening element (not shown). The split tube provides for a simple manufacturing process as well as a conductive pathway for bi-polar RF operation.

Referring to FIG. 4C, insulators 222 may be disposed around a portion of wire loop 210 so that only a desired portion of wire loop 210 may transfer RF current into the tissue for tissue modifying capability. Wire loop 210, covered with insulators 222 may extend proximally into support tubes 218. In various alternative embodiments, an electrode tissue modifying member (of which wire loop 210 is but one example) may be bipolar or monopolar. For example, as shown in FIG. 4C, a sleeve 224 housed toward the distal portion of window 211 may act as a return electrode for wire loop 210 in a bipolar device. Wire loop electrodes 210 may be made from various conductive metals such as stainless steel alloys, nickel titanium alloys, titanium alloys, tungsten alloys and the like. Insulators 222 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 222 may be composed of a ceramic-based material.

In one embodiment, wire loop 210 may be housed within elongate body 208 during delivery of tissue modification device 202 into a patient, and then caused to extend up out of window 211, relative to the rest of body 208, to remove tissue. Wire loop 210 may also be flexible so that it may pop or bow up out of window 211 and may deflect when it encounters hard tissue surfaces. Wire loop 210 may have any of a number of shapes, such as curved, flat, spiral or ridged. Wire loop 210 may have a diameter similar to the width of body 208, while in alternative embodiments it may expand when extended out of window 211 to have a smaller or larger diameter than that of body 208. Pull wires (not shown) may be retracted proximally, in a manner similar to that described above, in order to collapse wire loop 210, decrease the diameter and lower the profile of the wire loop 210, and/or pull wire loop 210 proximally to remove tissue or be housed within body 208. The low profile of the collapsed wire loop 210, facilitates insertion and removal of tissue modification device 202 prior to and after tissue modification. As the wire loop 210 diameter is reduced, support tubes 218 deflect toward the center of elongate body 208.

In an alternative embodiment (not shown), tissue modification device 202 may include multiple RF wire loops 210 or other RF members. In another embodiment, device 202 may include one or more blades as well as RF wire loop 210. In such an embodiment, wire loop 210 may be used to remove or otherwise modify soft tissues, such as ligamentum flavum, or to provide hemostasis, and blades may be used to modify hard tissues, such as bone. In other embodiments, as described further below, two separate tissue modification devices (or more than two devices) may be used in one procedure to modify different types of tissue, enhance modification of one type of tissue or the like.

In other alternative embodiments, tissue modification devices 202 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods.

Figure 5A:
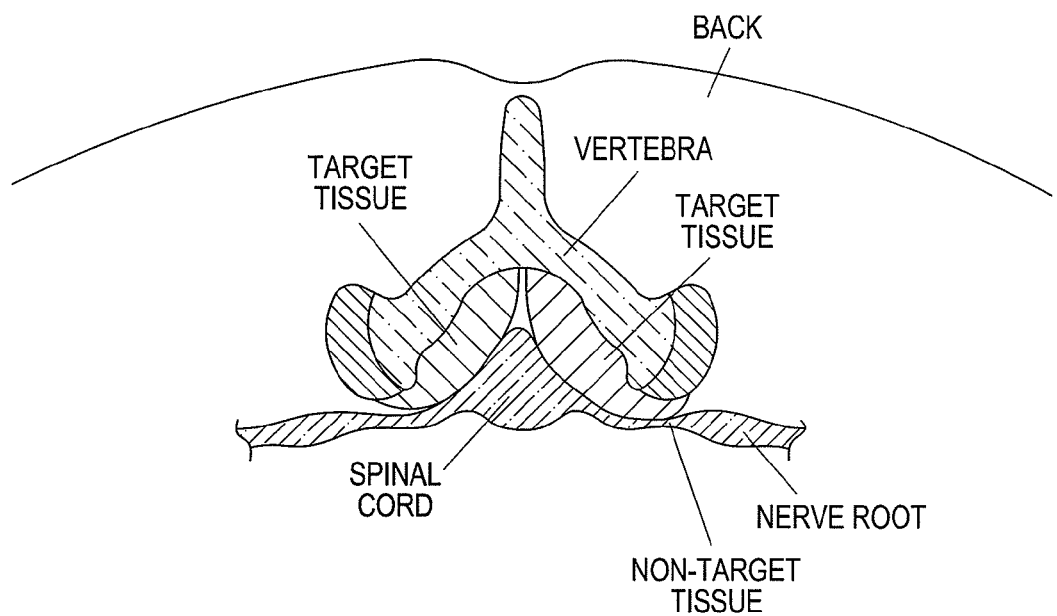
FIGS. 5A-5D are cross-sectional views of a spine and demonstrate a method for using a tissue modification device according to one embodiment of the present invention.

Referring now to FIGS. 5A-5D, one embodiment of a method for modifying tissue in a spine is demonstrated in simplified, diagrammatic, cross-sectional views of a portion of a patient's back and spine. FIG. 5A shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

Figure 5B:
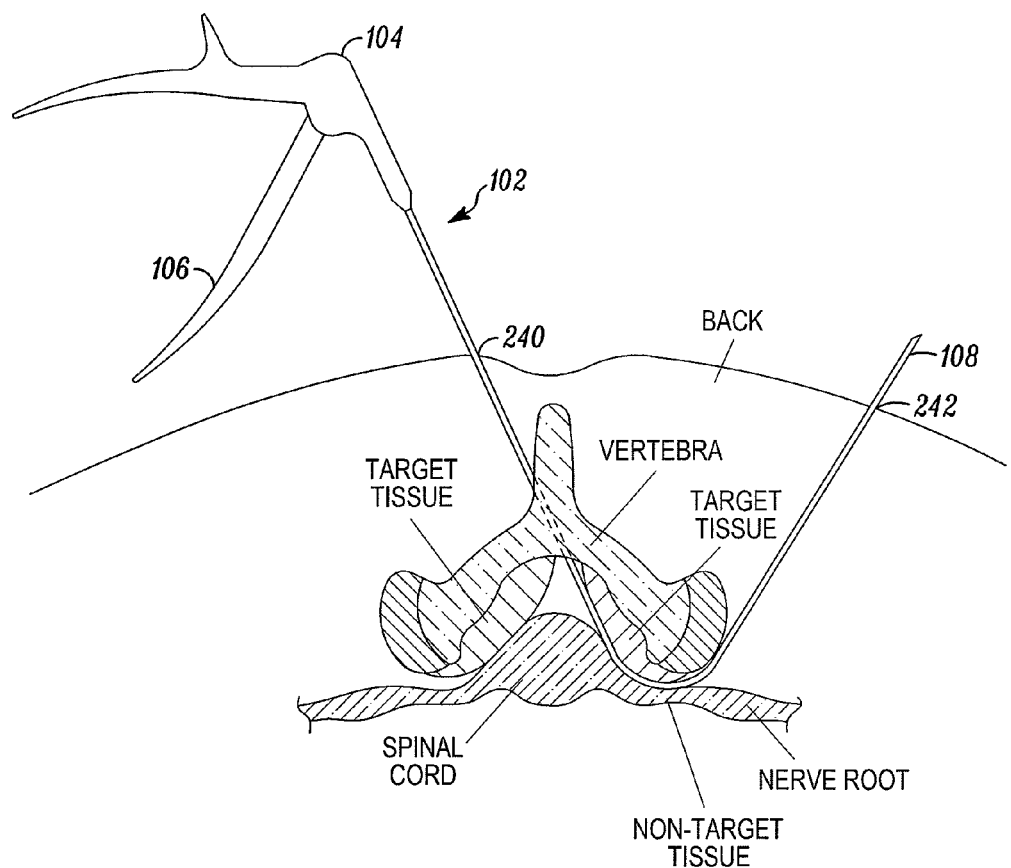

In FIG. 5B, tissue modification device 102 has been positioned in the patient's back to perform a tissue modification procedure. Various methods, devices and systems for introducing device 102 into the patient and advancing it to the position for modifying tissue are described in further detail below. Generally, device 102 may be positioned via a percutaneous or open surgical procedure, according to various embodiments. In one embodiment, device 102 may be inserted into the patient through a first incision 240, advanced into the spine and between target tissue and non-target tissue (such as spinal cord, nerve roots, nerves and/or neurovascular tissue), and further advanced so a distal portion of elongate body 108 exits a second (or distal) incision 242 to reside outside the patient. In positioning device 102, one or more tissue modifying members (not shown) are positioned to face the target tissue, while one or more protective portions of elongate body 108 face non-target tissue.

Figure 5C:
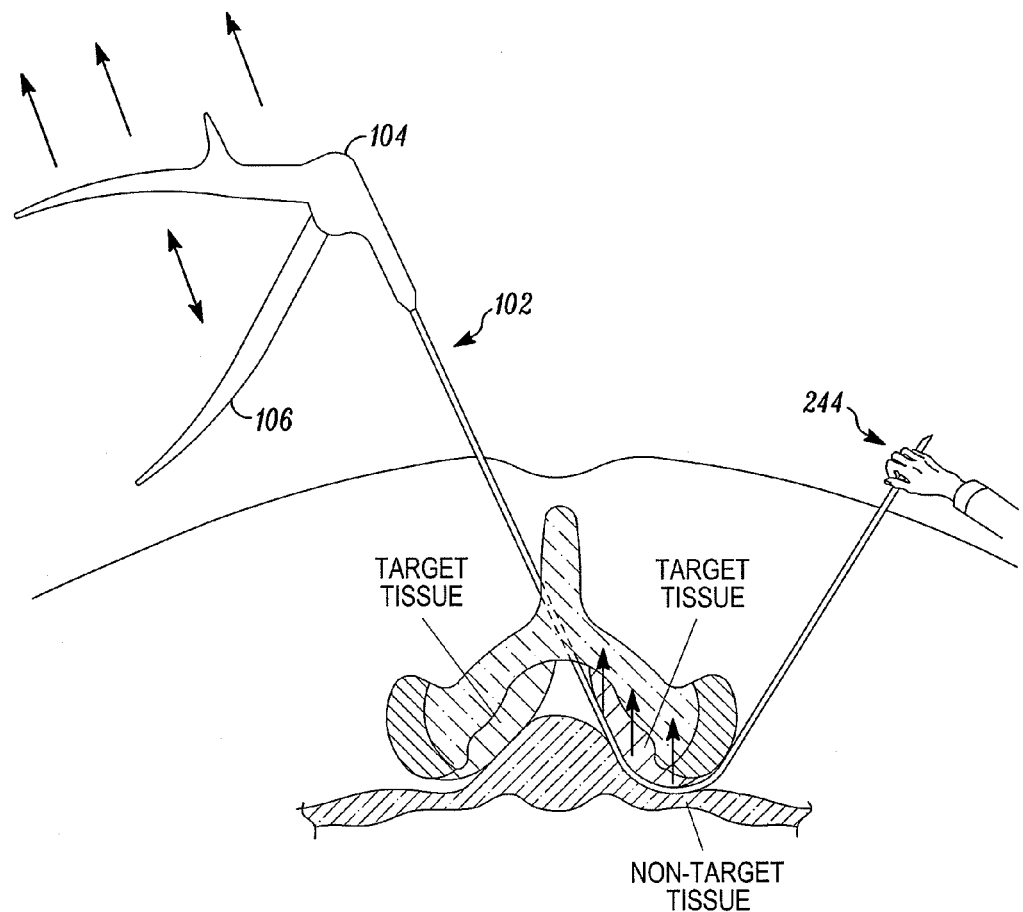

Referring to FIG. 5C, once device 102 is positioned in a desired location, anchoring force may be applied at or near the distal portion of elongate body 108. In one embodiment, applying anchoring force involves a user 244 grasping body 108 at or near its distal portion. In alternative embodiments, as described further below, anchoring force may be applied by deploying one or more anchor members disposed at or near the distal portion of body 108, or by grasping a guidewire or other guide member extending through at least part of body 108. Once the anchoring force is applied, proximally-directed tensioning force may be applied to device 102, such as by pulling proximally on handle 104 (one-directional, diagonal arrows). This tensioning force, when applied to the substantially anchored device 102, may help urge the tissue modifying member(s) against the target tissue (one-directional, vertical arrows near target tissue), thus enhancing contact with the target tissue and facilitating its modification. With the tissue modifying member(s) contacting the target tissue, actuator 106 may be squeezed or pulled (two-headed arrow) to cause the tissue modifying member(s) to modify tissue. (Alternative actuators may be activated in different ways in alternative embodiments.)

In various alternative embodiments, certain of the above-described steps may be carried out in different order. For example, in one embodiment the distal portion of elongate body 108 may be anchored within or outside the patient before the tissue modifying members are positioned adjacent the target tissue. In another alternative embodiment, the proximal portion of device 102 may be anchored, and the tensioning force may be applied to the distal portion of device 102. In yet another embodiment, tensioning force may be applied to both ends of the device. In yet another embodiment, a second handle and actuator may be coupled with the distal end of body 108 after it exits the patient's back, allowing tensioning forces as well as tissue modifying actuation to occur at both the proximal and distal portions of device 102. By anchoring one end of device 102 and applying tensioning force to the opposite end, contact of the tissue modifying members with the target tissue is enhanced, thus reducing or eliminating the need for translating or otherwise moving device 102 as a whole and reducing the overall profile and the resulting access pathway required to position the device. Reducing movement and profile of device 102 and using tissue modifying members confined to a relatively small area of device 102 helps facilitate target tissue modification while minimizing or eliminating damage to surrounding tissues or structures.

As mentioned above, tissue may be modified using one tissue modification device or multiple devices, according to various embodiments. In one embodiment, for example, an RF electrosurgical tissue modification device may be used in the patient to remove soft tissue such as ligament, and a bladed tissue modification device such as a rongeur may then be used to remove additional soft tissue, calcified soft tissue, or hard tissue such as bone. In some embodiments, such multiple devices may be inserted, used and removed serially, while in alternative embodiments such devices may be inserted into the patient at the same time to be used in combination.

Figure 5D:
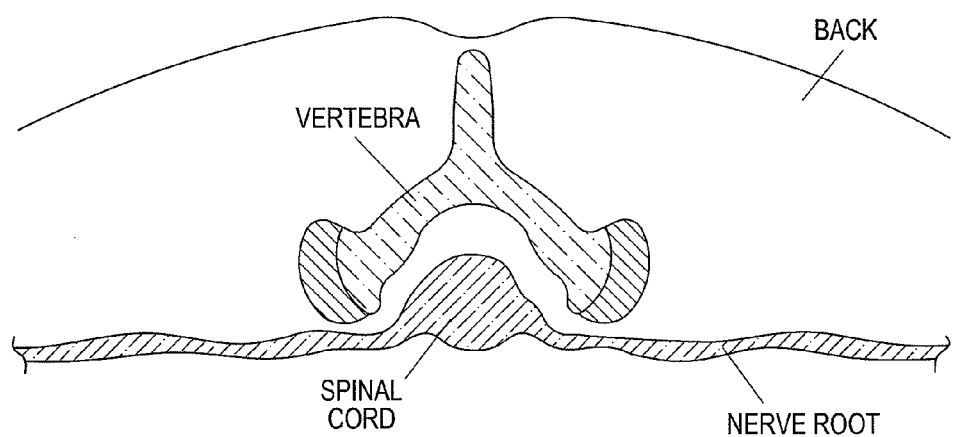

Referring to FIG. 5D, using one or more tissue modification devices 102, a desired amount of target tissue may be removed from more than one area in the spine. FIGS. 5A-5C demonstrate removal of target tissue on one side of the spine, and that method or a similar method may also be used to remove target tissue on an opposite side of the spine, as shown in FIG. 5D, where target tissue has been removed from both sides. That the desired amount of tissue has been removed may be confirmed by tactile feedback from the device or from a separate device, by testing nerve conduction through one or more previously impinged nerves, by testing blood flow through one or more previously impinged blood vessels, by passing (independently or over the guide member) a measurement probe or sound through the treated portion, through one or more radiographic tests, through some combination thereof, or by any other reasonable means.

Figure 6A:
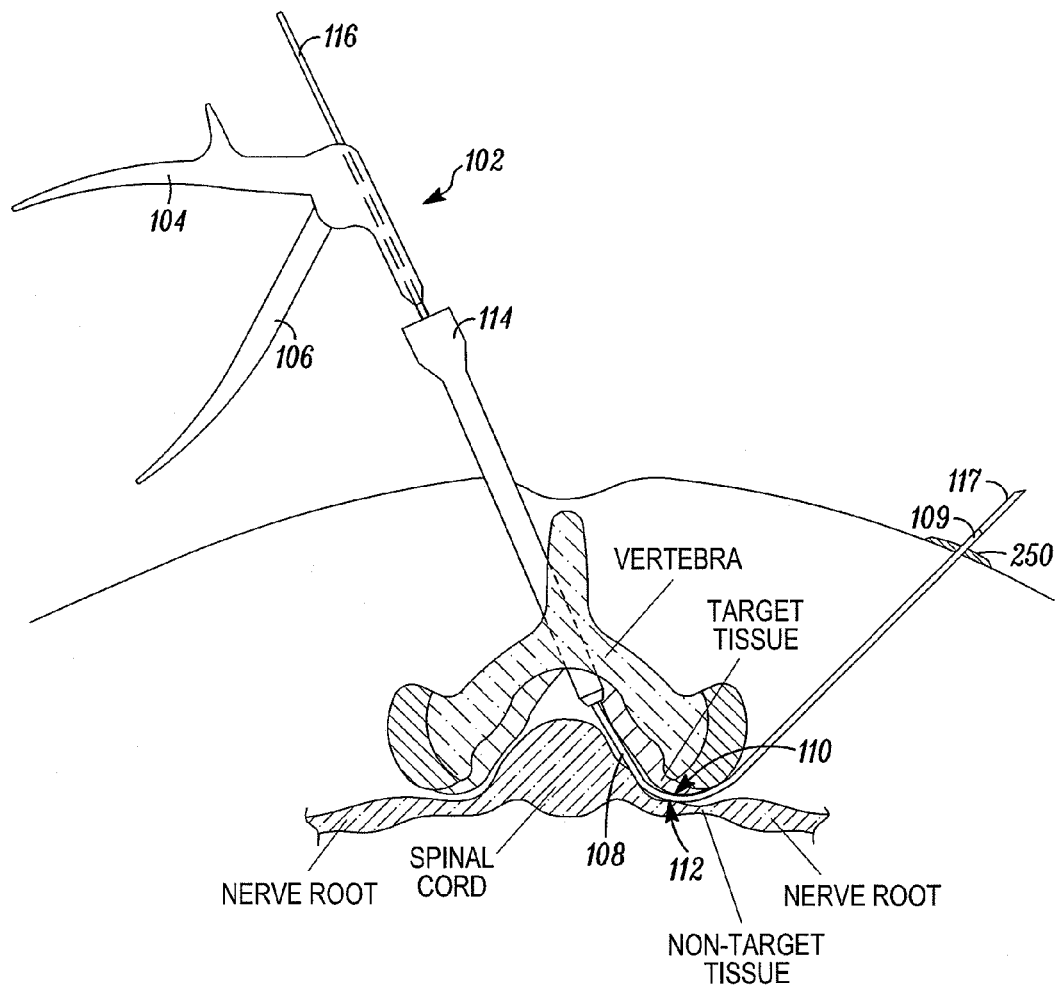
FIG. 6A is a cross-sectional view of a portion of a patient's spine and back, with apparatus for modifying tissue in position for modifying spinal tissue and with a distal portion of the apparatus anchored outside the patient according to one embodiment of the present invention.

Referring now to FIG. 6A, tissue modification device 102 is shown with one embodiment of a distal anchoring member 250 deployed at the patient's skin. In various embodiments, anchoring members may include but are not limited to one or more handles, barbs, hooks, screws, toggle bolts, needles, inflatable balloons, meshes, stents, wires, lassos, backstops or the like. In some embodiments, anchoring members 250 may be disposed at the extreme distal portion 109 of elongate body 108, while in other embodiments anchoring members 250 may be located more proximally. In the embodiment shown, anchoring members 250 are deployed at the patient's skin. In an alternative embodiment, anchoring may be achieved outside the patient by deploying one or more anchoring members 250 above the skin and having a user grasp the anchoring members 250. In an alternative embodiment, anchoring may be achieved outside the patient by deploying one or more anchoring members 250 above the skin and having a user grasp anchoring members 250, after tissue modification device 102 has been anchored to the guide member. In another alternative embodiment, anchoring may be achieved outside the patient by attaching anchoring member 250 to an external device, for example one that is mounted on the patient or on the procedure table. In a further alternative embodiment, anchoring may be achieved outside the patient by attaching the guide member to an external device, for example one that is mounted to on the patient or on the procedure table, after tissue modification device 102 has been anchored to the guide member. Anchoring members 250 generally are deployable from a first, contracted configuration to facilitate delivery of device 102, to a second, expanded configuration to facilitate anchoring. This change in configuration may be achieved, for example, by using shape memory or superelastic materials, by spring loading anchoring members 250 into body 108 or the like. In most embodiments, anchoring members 250 may also be collapsed down into the first, contracted configuration after a tissue modification procedure has been performed, to facilitate withdrawal of device 102 from the patient. In an alternative embodiment, anchoring members 250 may detach from body 108 and may be easily removable from the patient's skin.

Figure 6B:
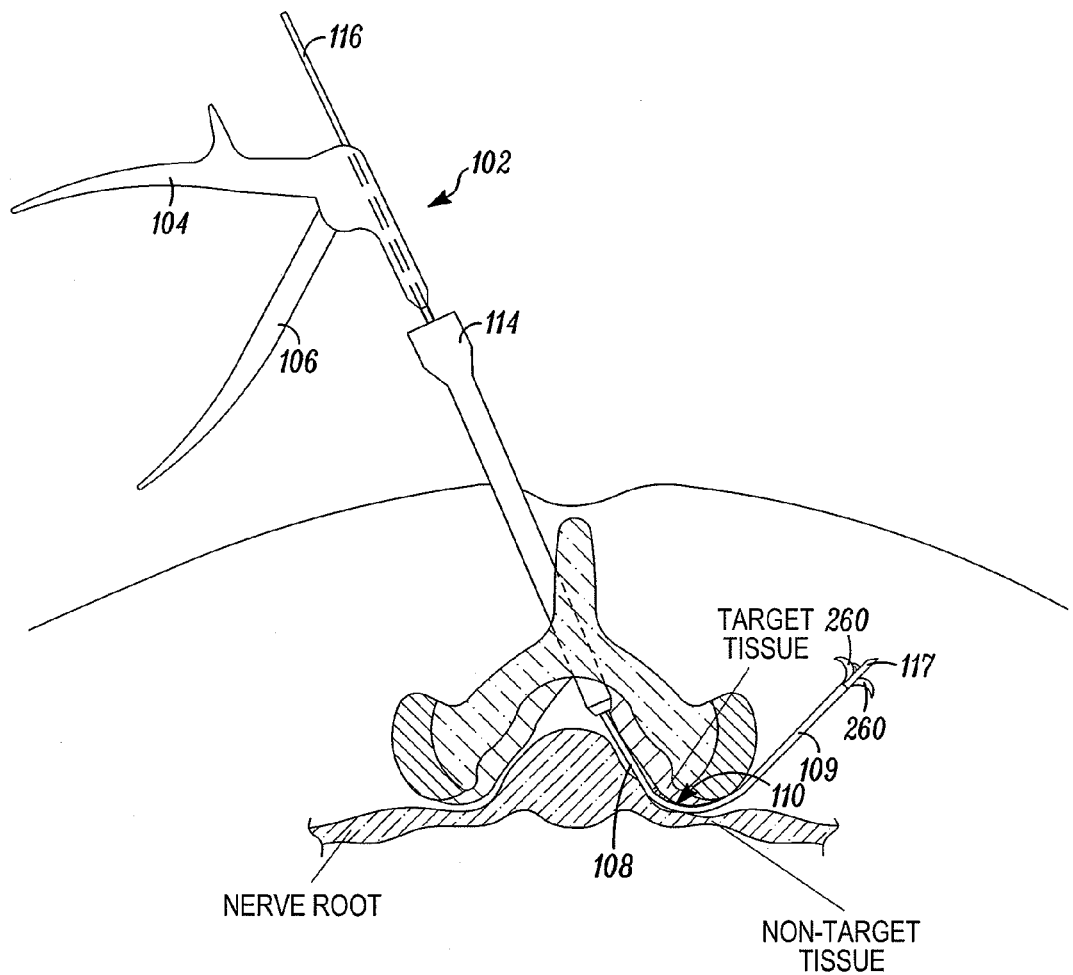
FIG. 6B is a cross-sectional view of a portion of a patient's spine and back, with apparatus for modifying tissue in position for modifying spinal tissue and with a distal portion of the apparatus anchored inside the patient according to one embodiment of the present invention.

FIG. 6B shows tissue modification device 102 with an alternative embodiment of a distal anchoring member 260. Here, distal anchoring member 260 includes multiple hooks or barbs extended out the distal portion 109 of elongate body 108 within the patient's back. In using such an embodiment, it may not be necessary to pass guide member 117 through a second, distal incision on the patient, although in some embodiments guide member 117 may extend significantly beyond distal portion 109. Anchoring member(s) 260, according to various embodiments, may be deployed so as to anchor to bone, ligament, tendon, capsule, cartilage, muscle, or any other suitable tissue of the patient. They may be deployed into vertebral bone or other suitable tissue immediately adjacent an intervertebral foramen or at a location more distant from the intervertebral foramen. When a tissue modification procedure is complete, anchoring members 260 are retracted within elongate body for removal of device 102 from the patient.

Figure 7A:
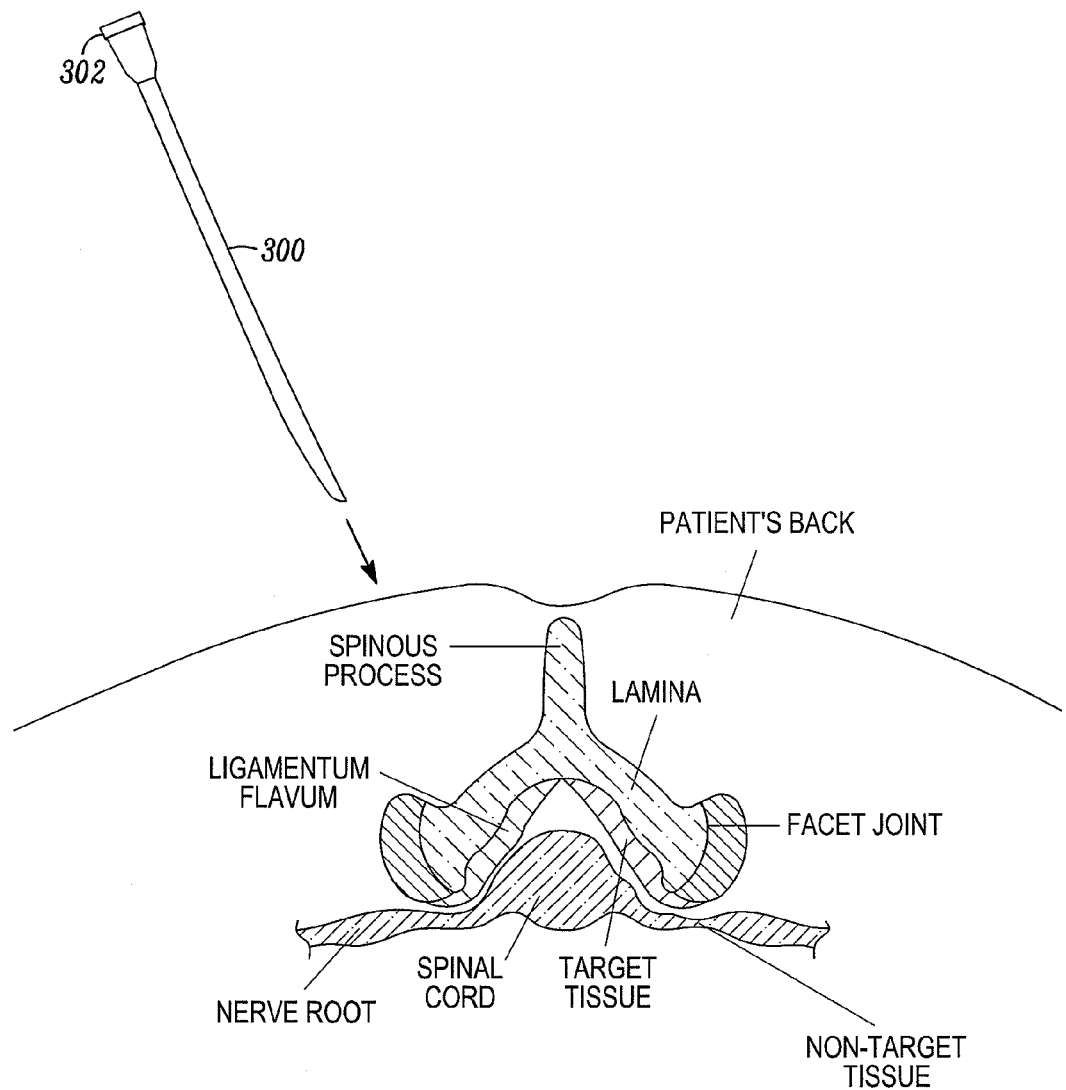
FIGS. 7A-7S are cross-sectional views of a portion of a patient's spine and back, demonstrating a method for introducing apparatus for modifying spinal tissue to an area in the spine for performing the tissue modification according to one embodiment of the present invention.
Figure 7B:
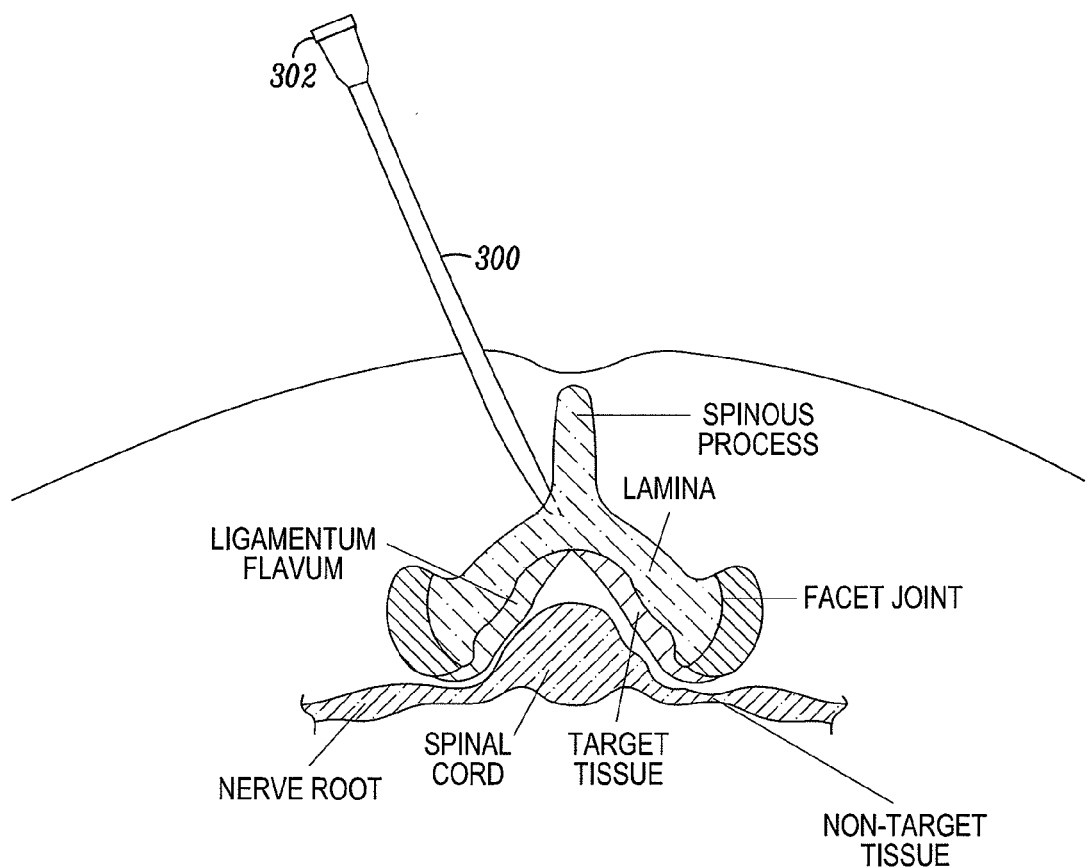
Figure 7C:
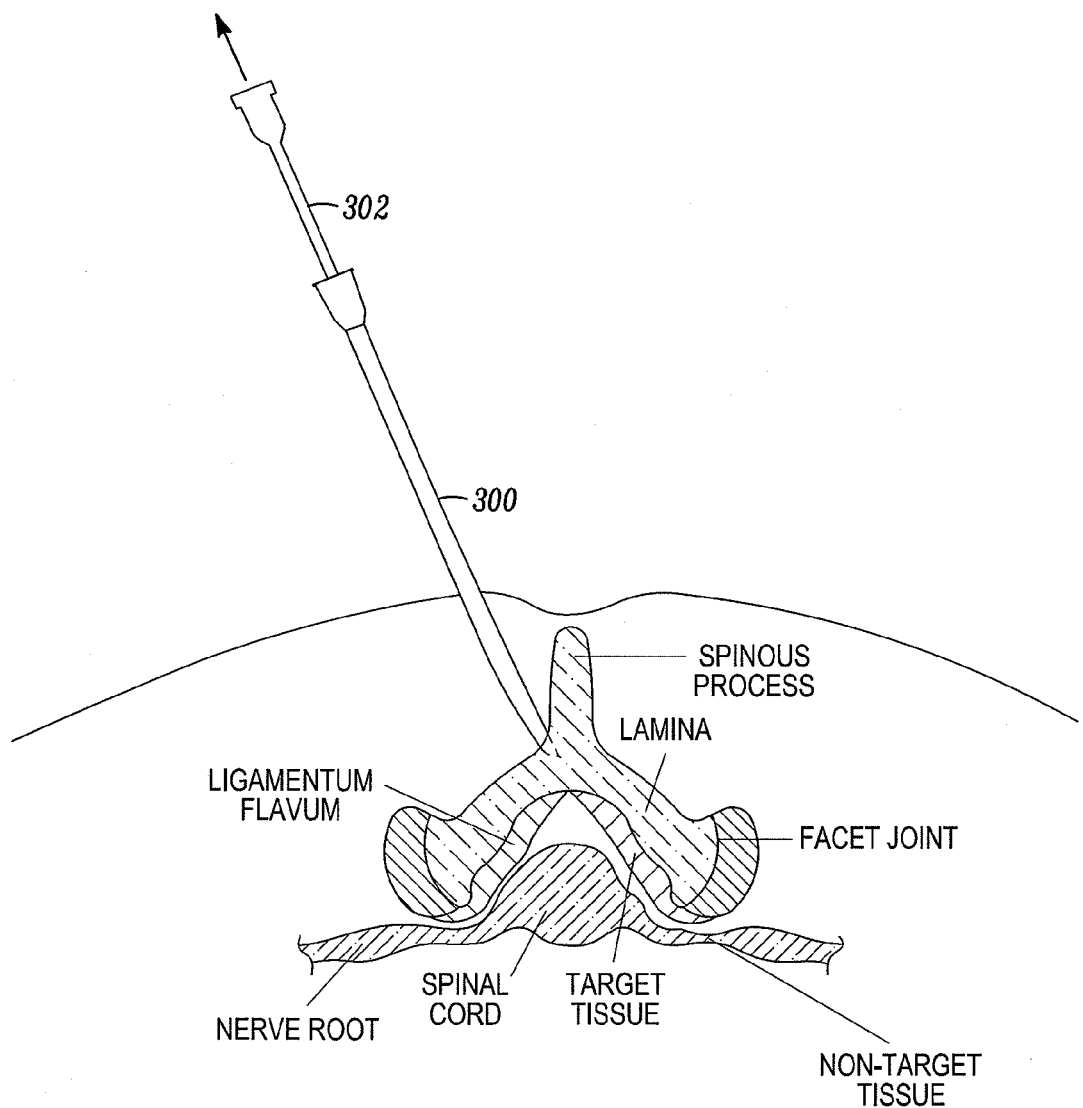
Figure 7D:
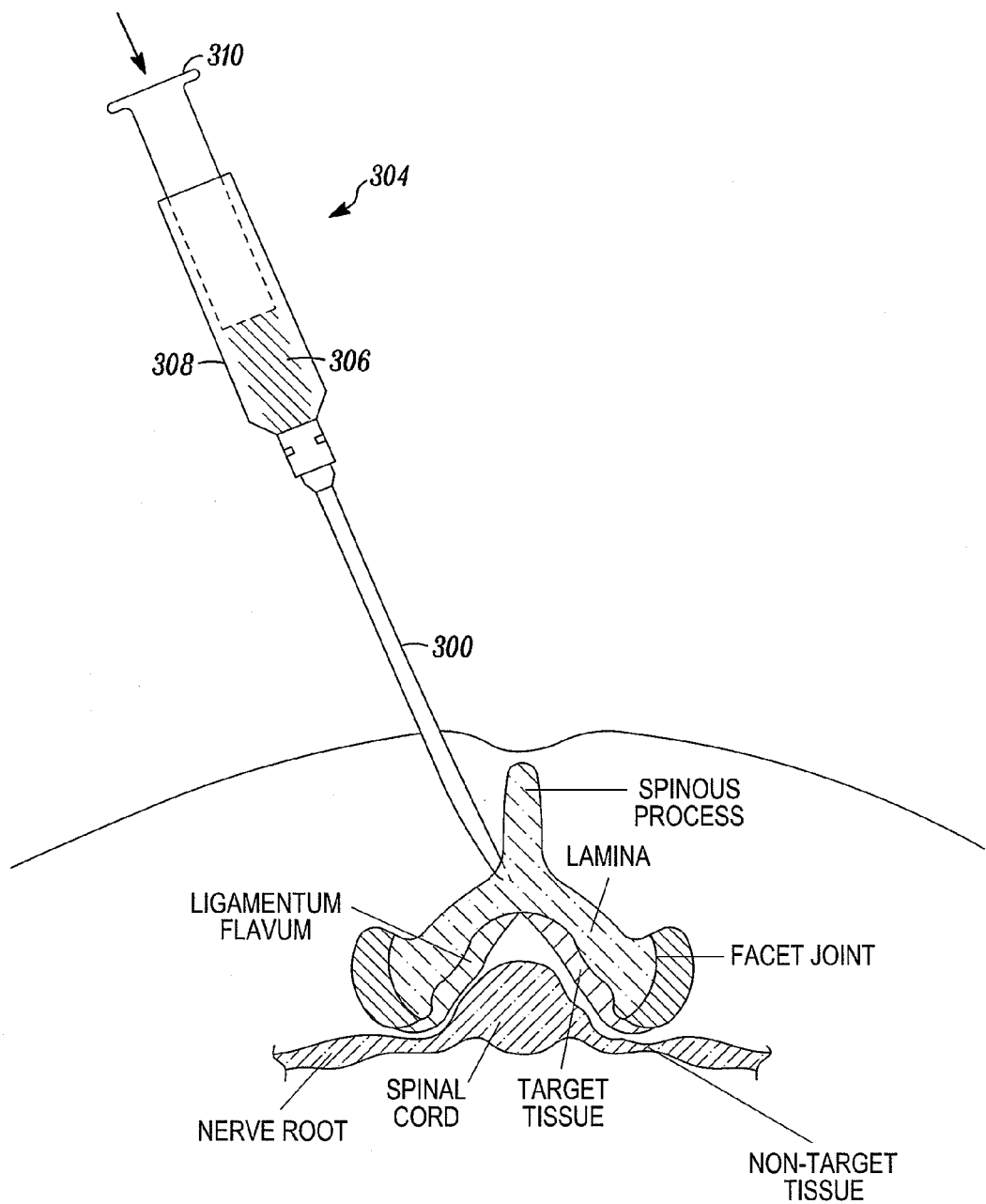
Figure 7E:
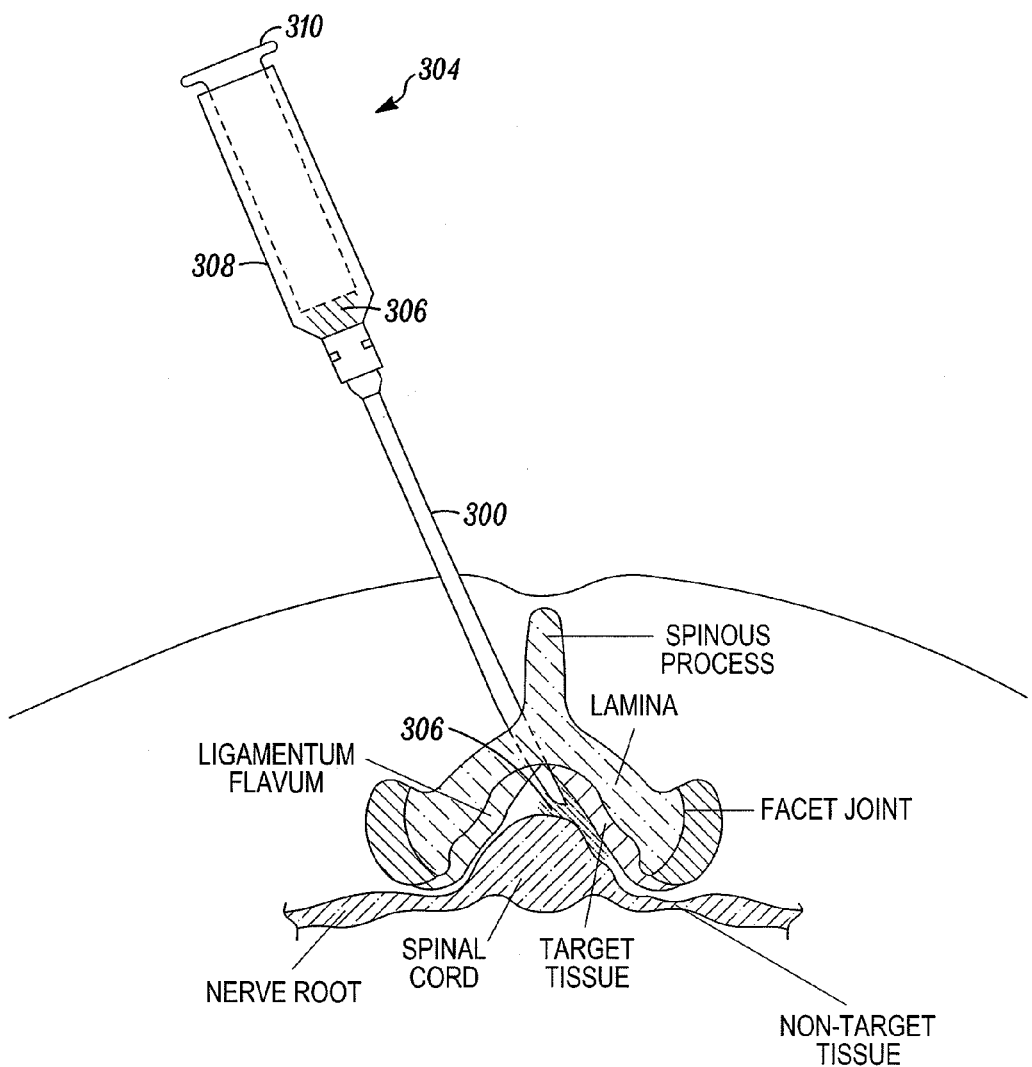
Figure 7F:
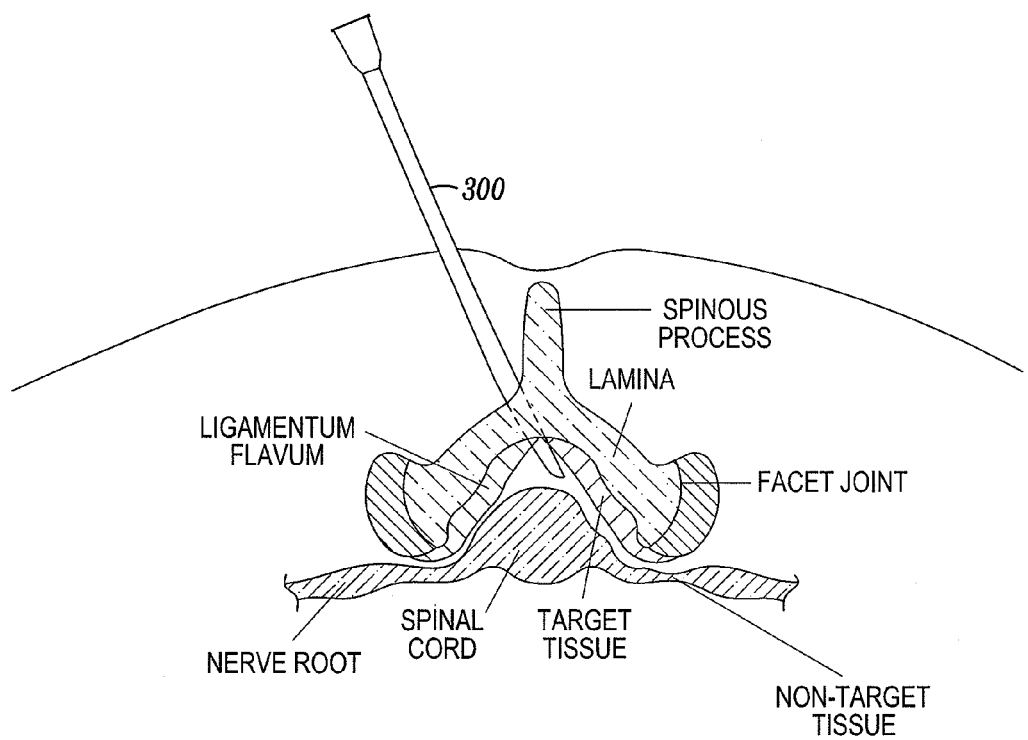
Figure 7G:
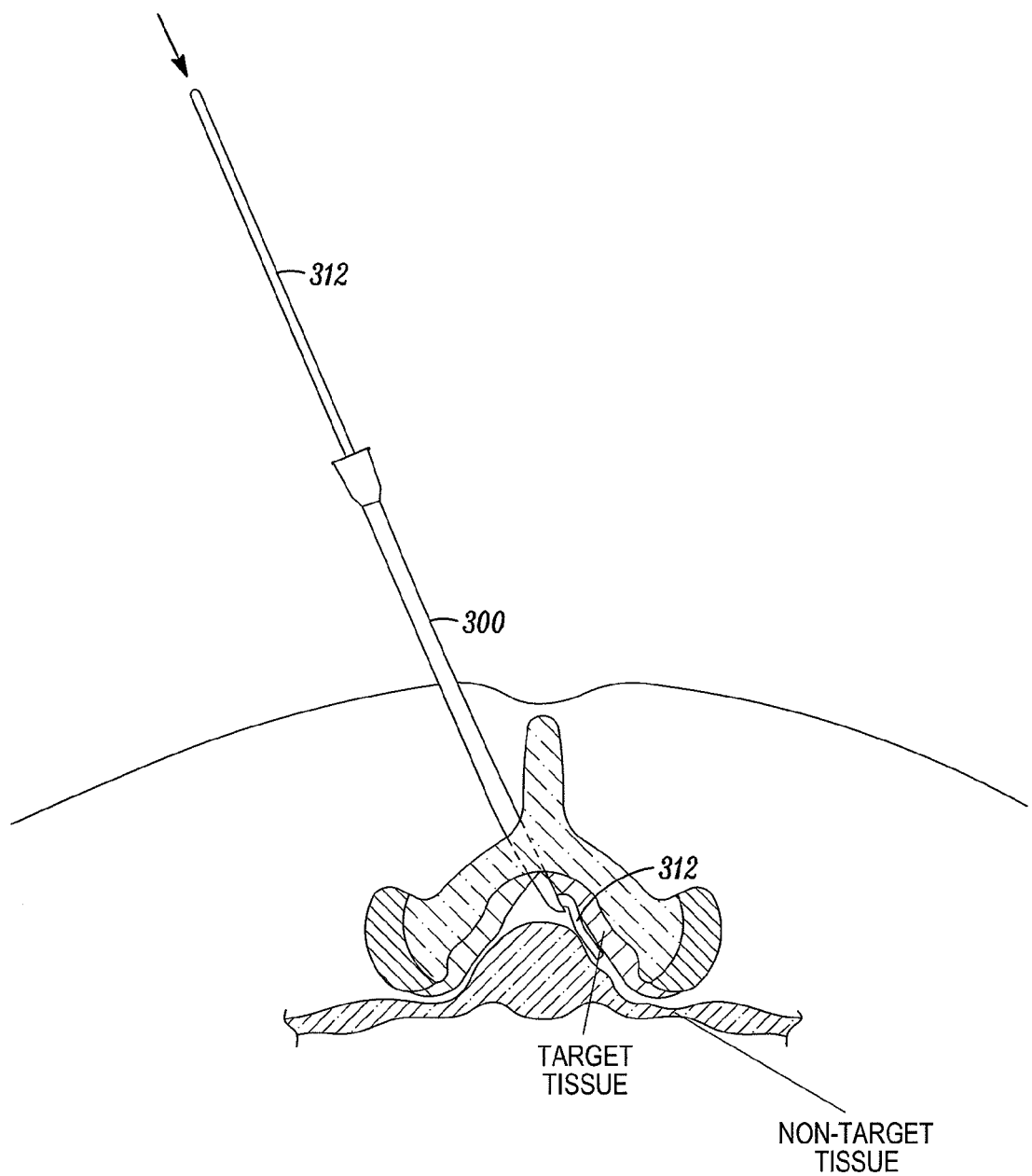
Figure 7H:
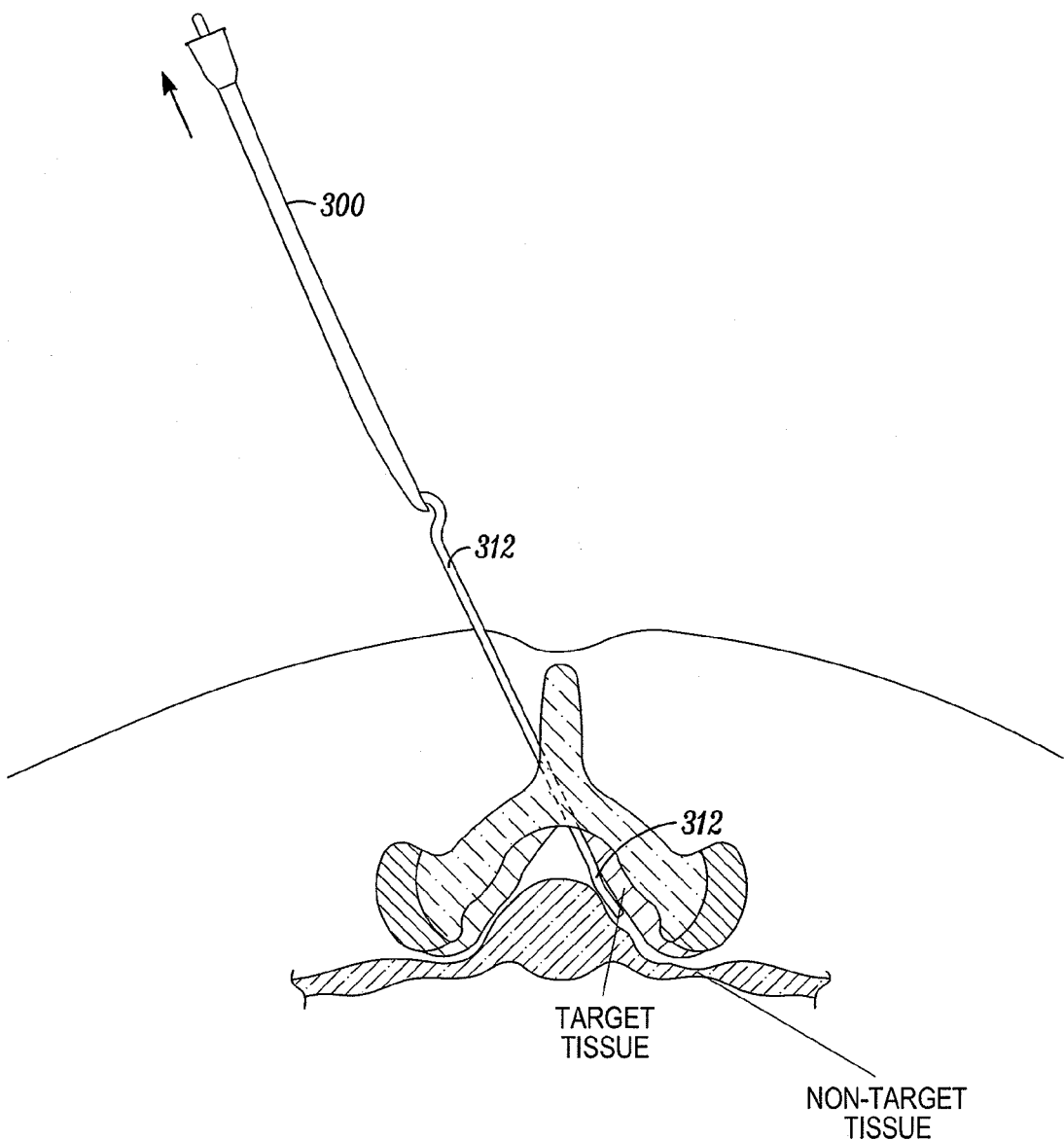
Figure 71:
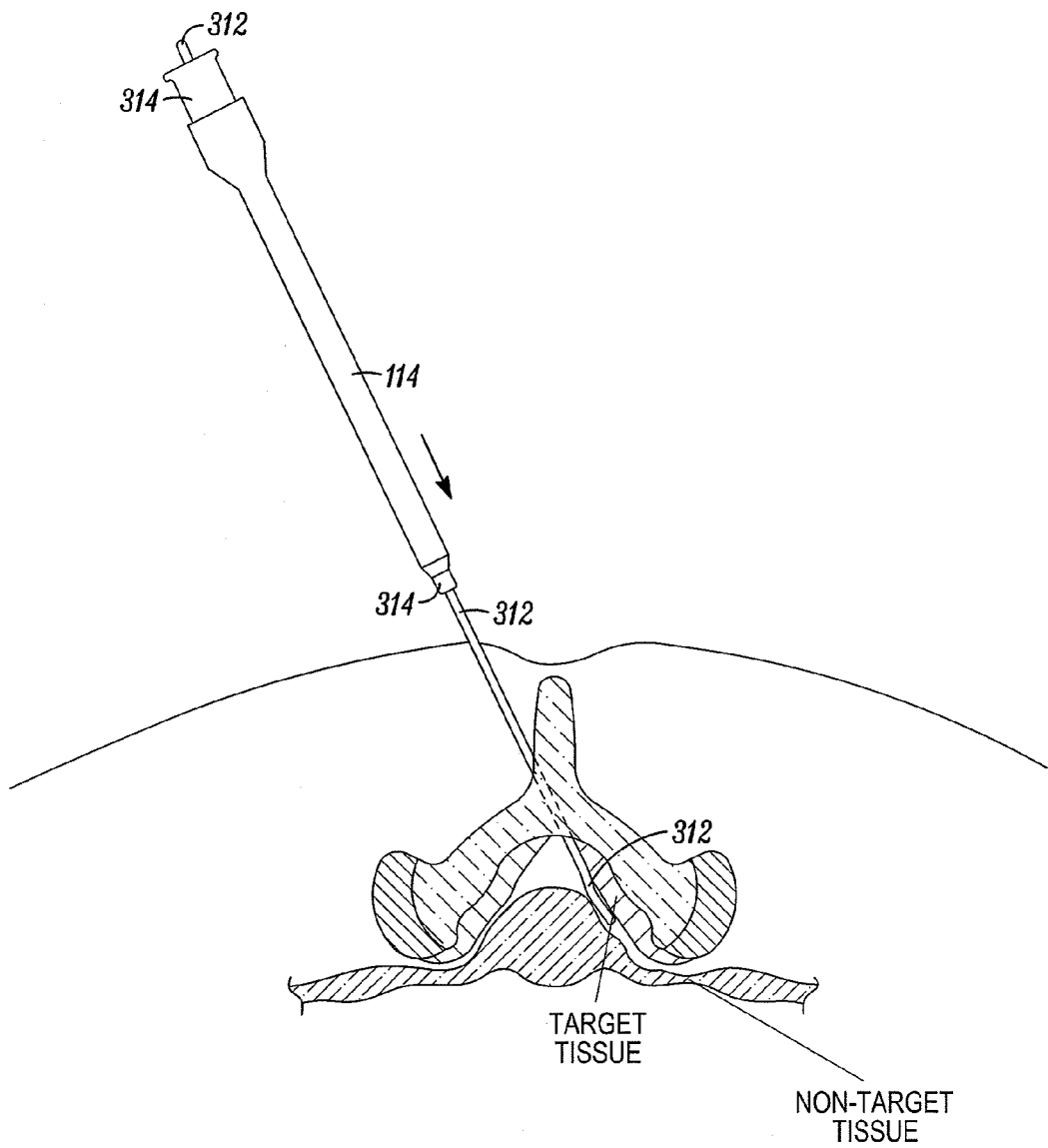
Figure 7J:
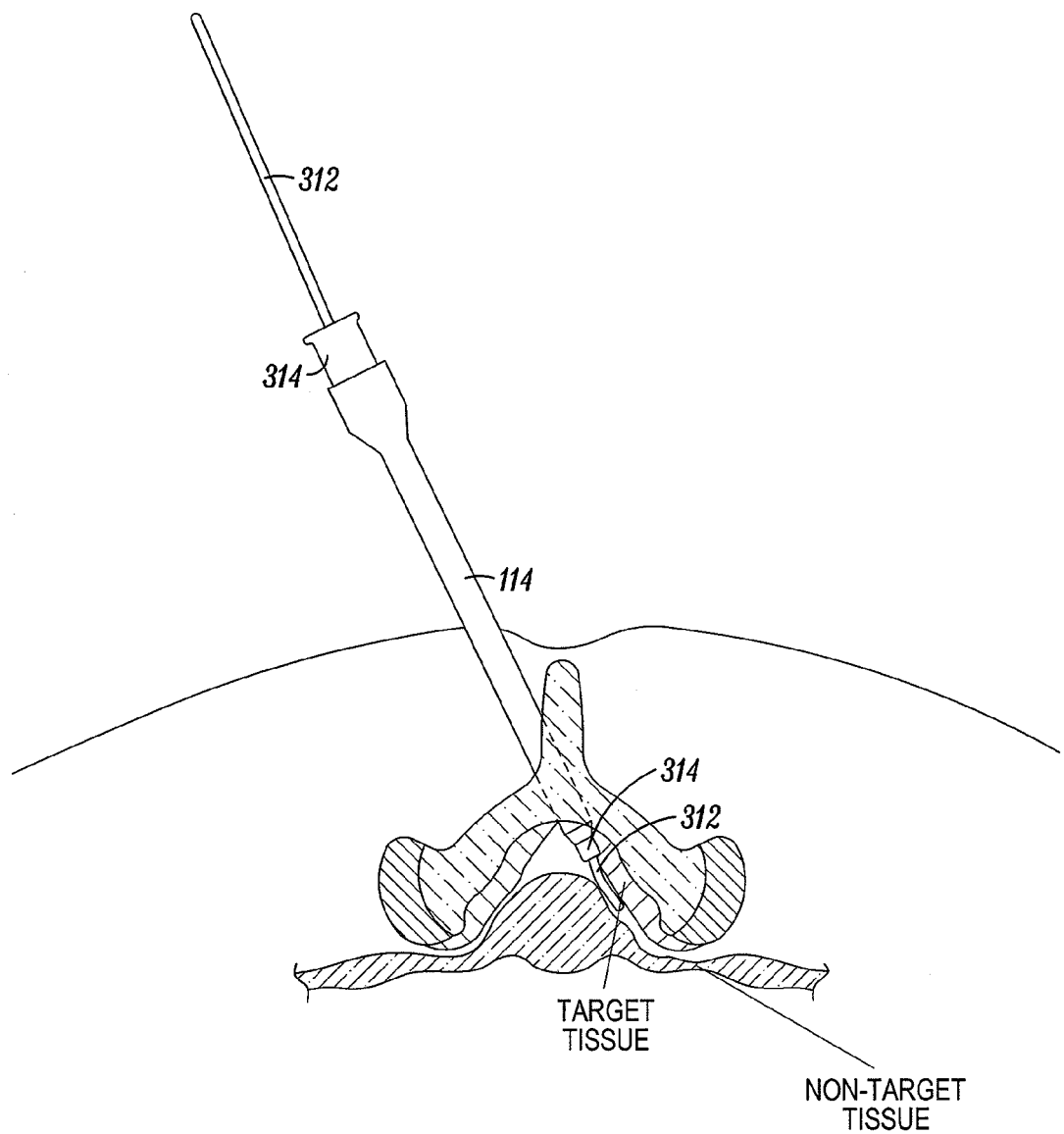
Figure 7K:
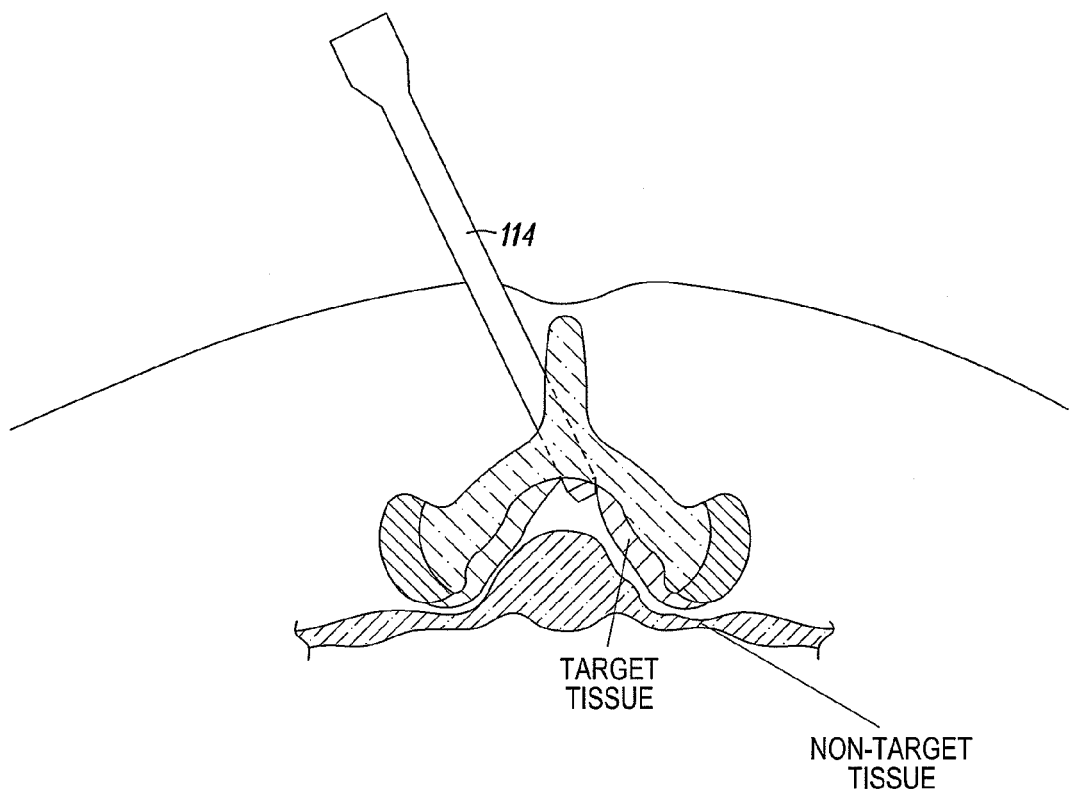
Figure 7L:
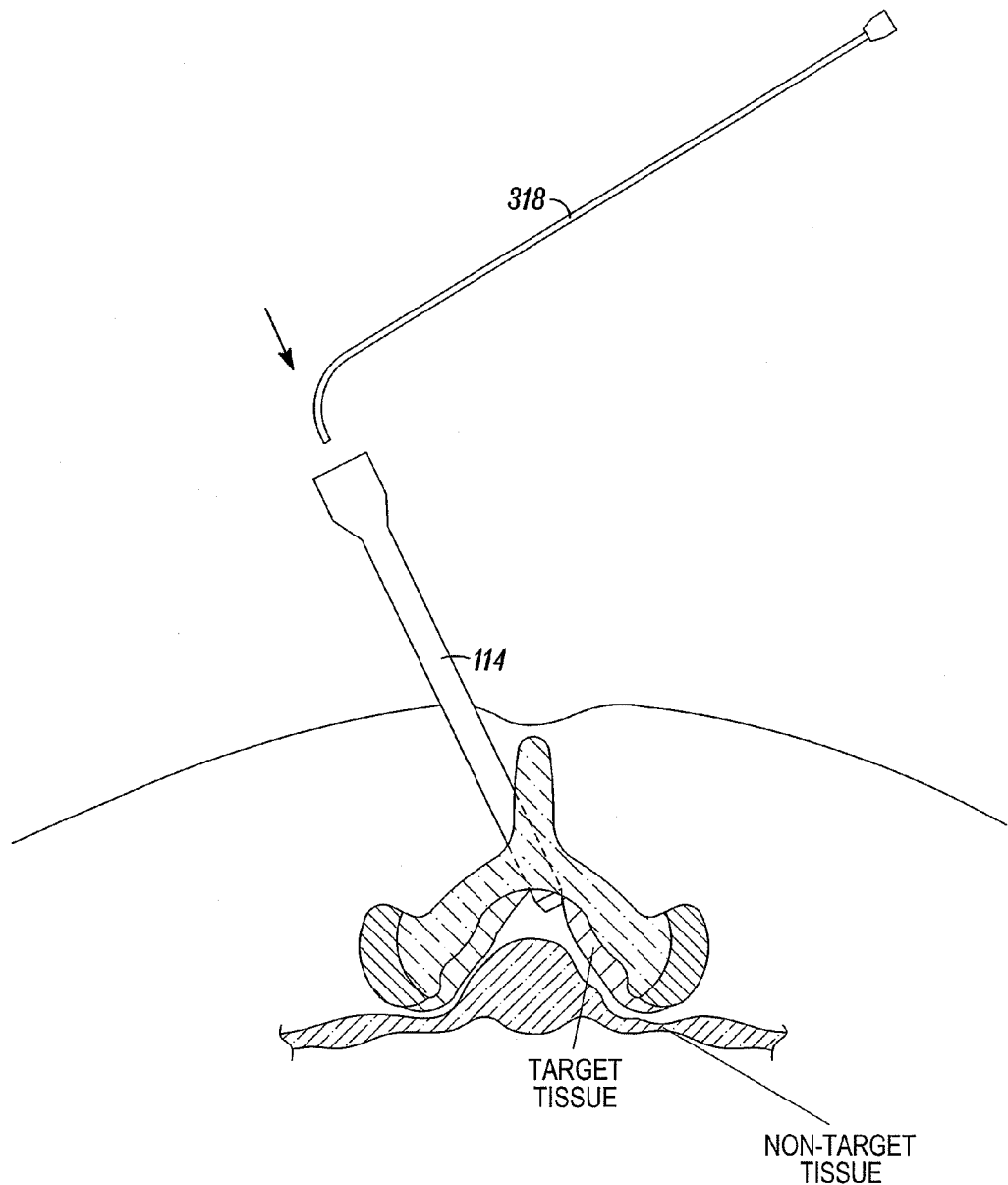
Figure 7M:
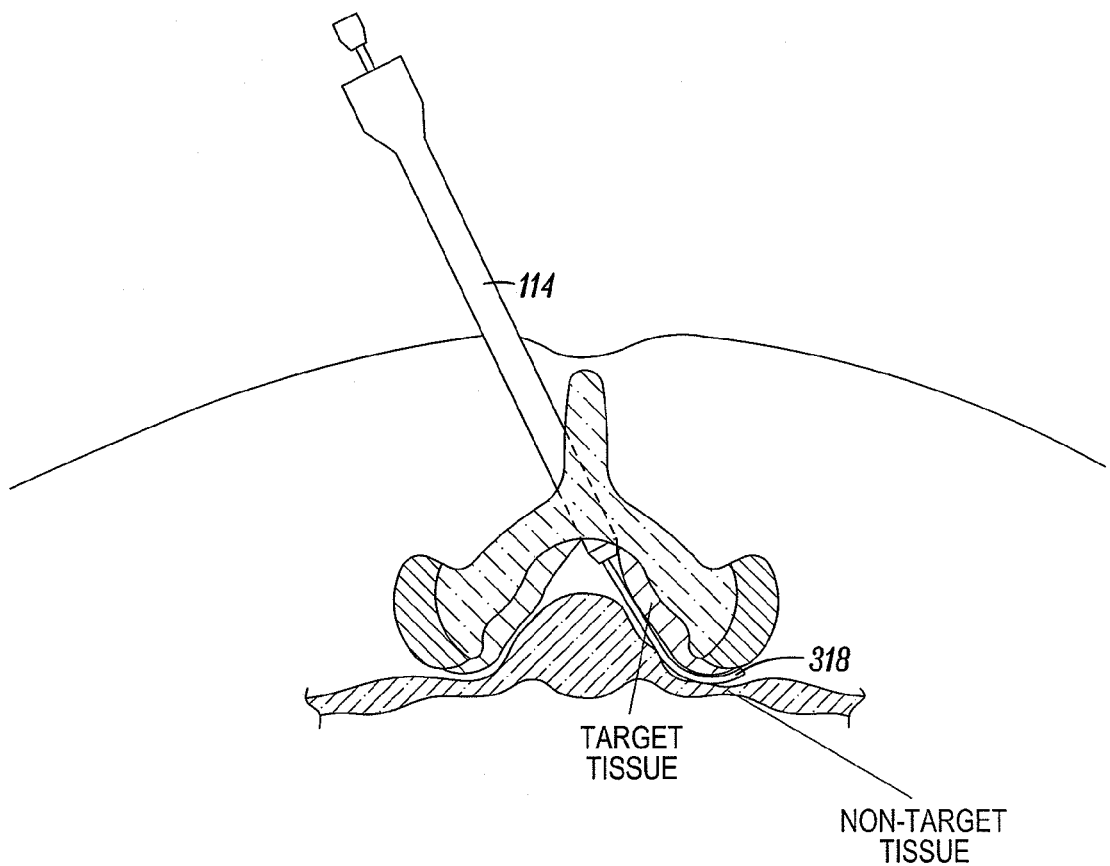
Figure 7N:
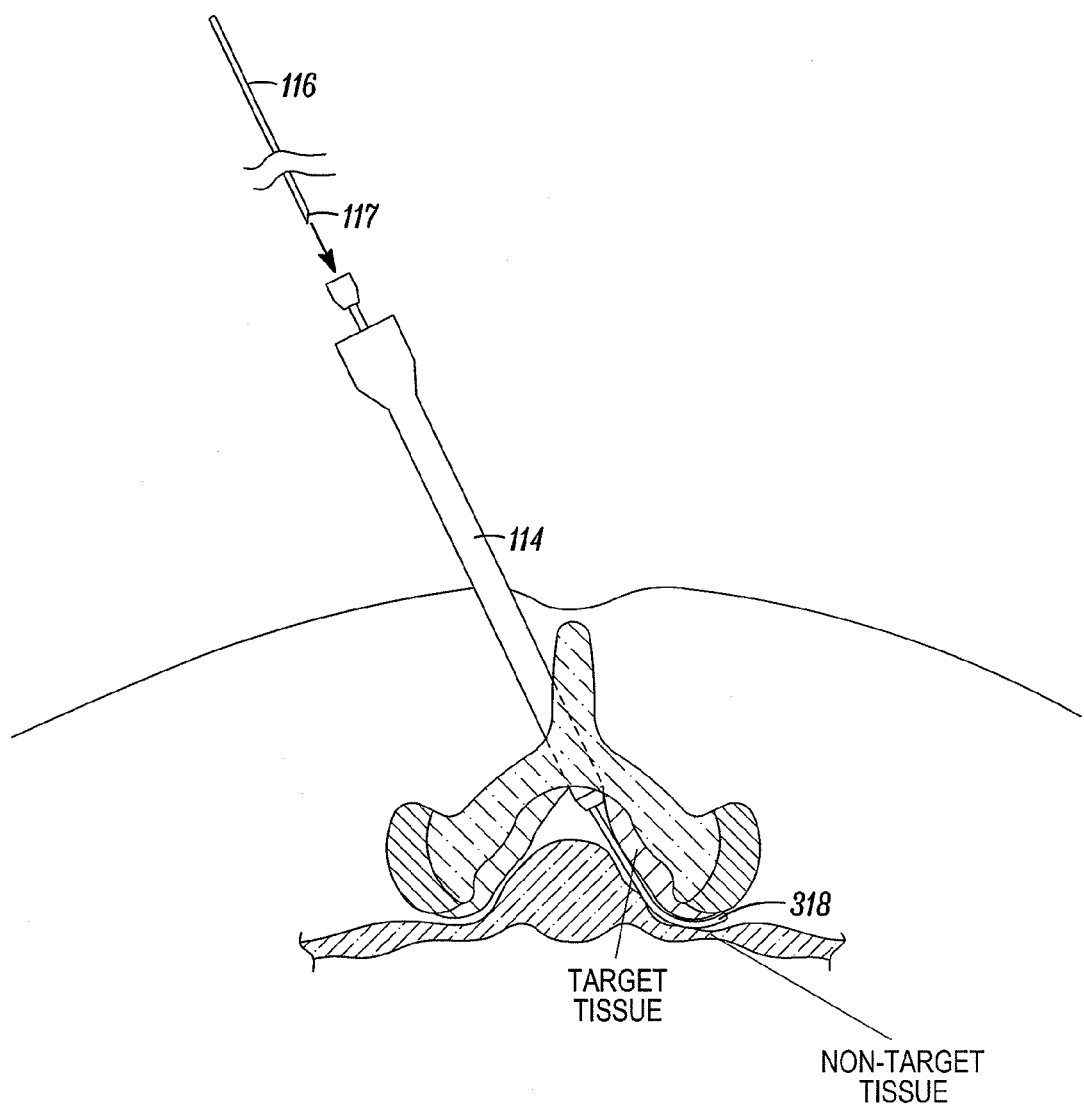
Figure 7O:
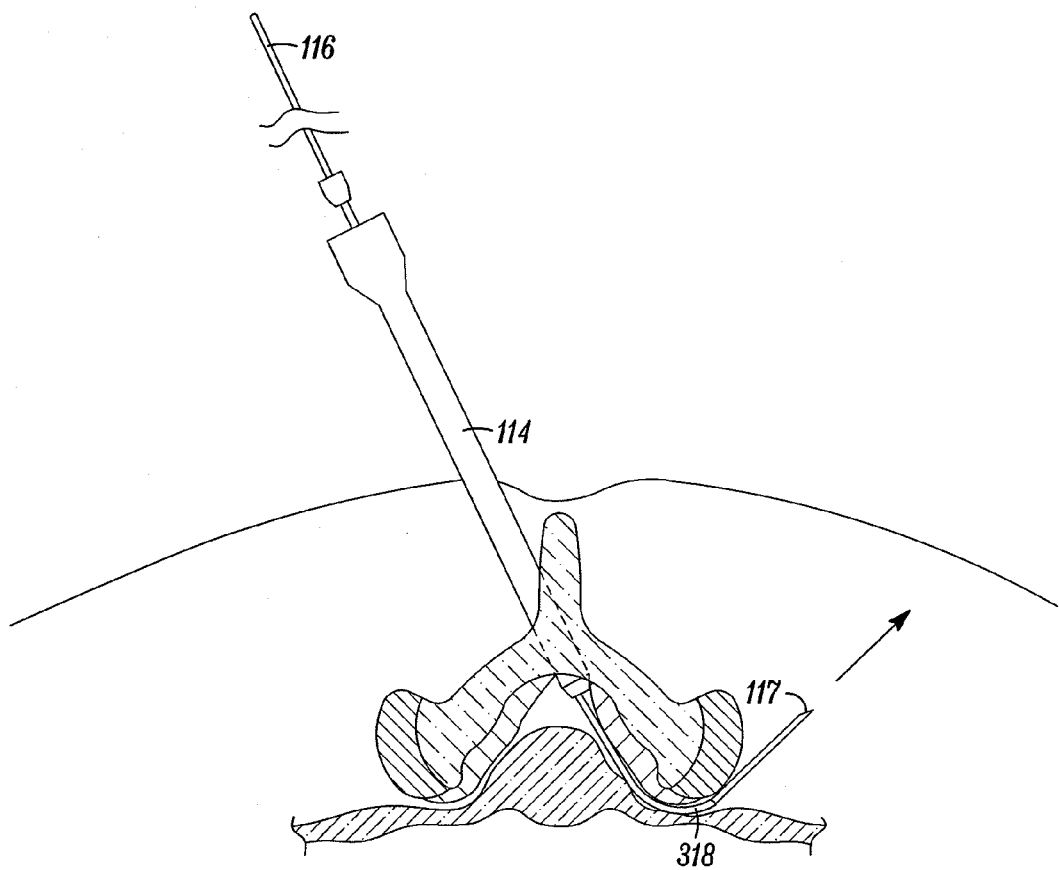
Figure 7P:
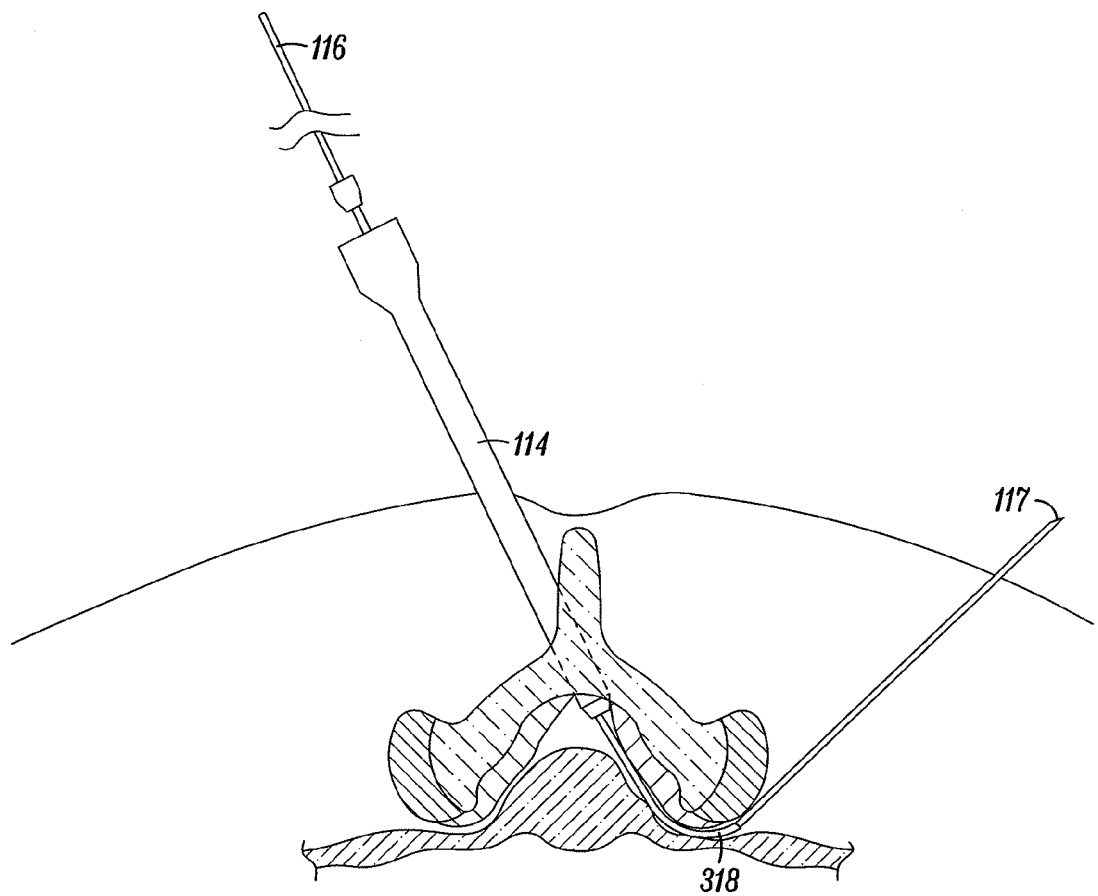
Figure 7Q:
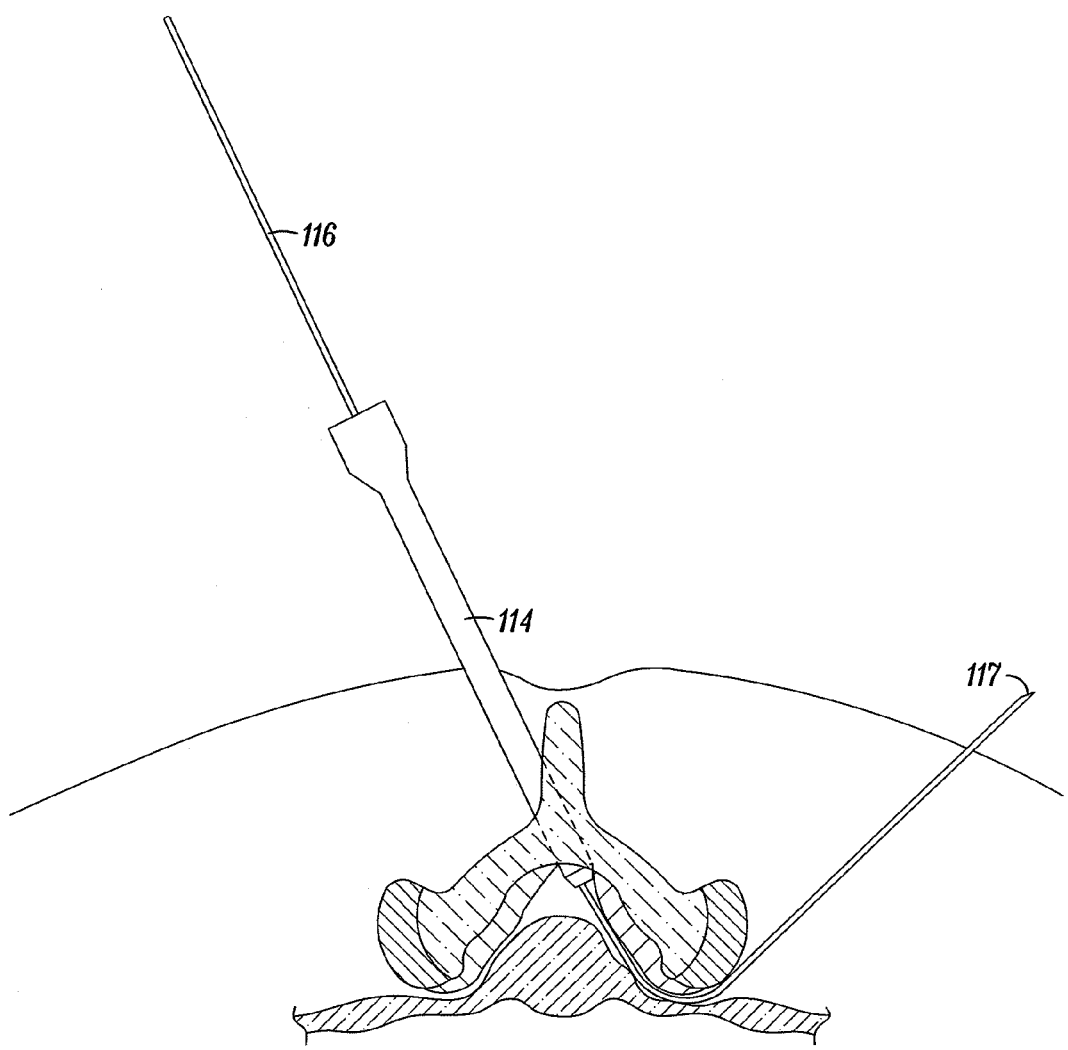
Figure 7R:
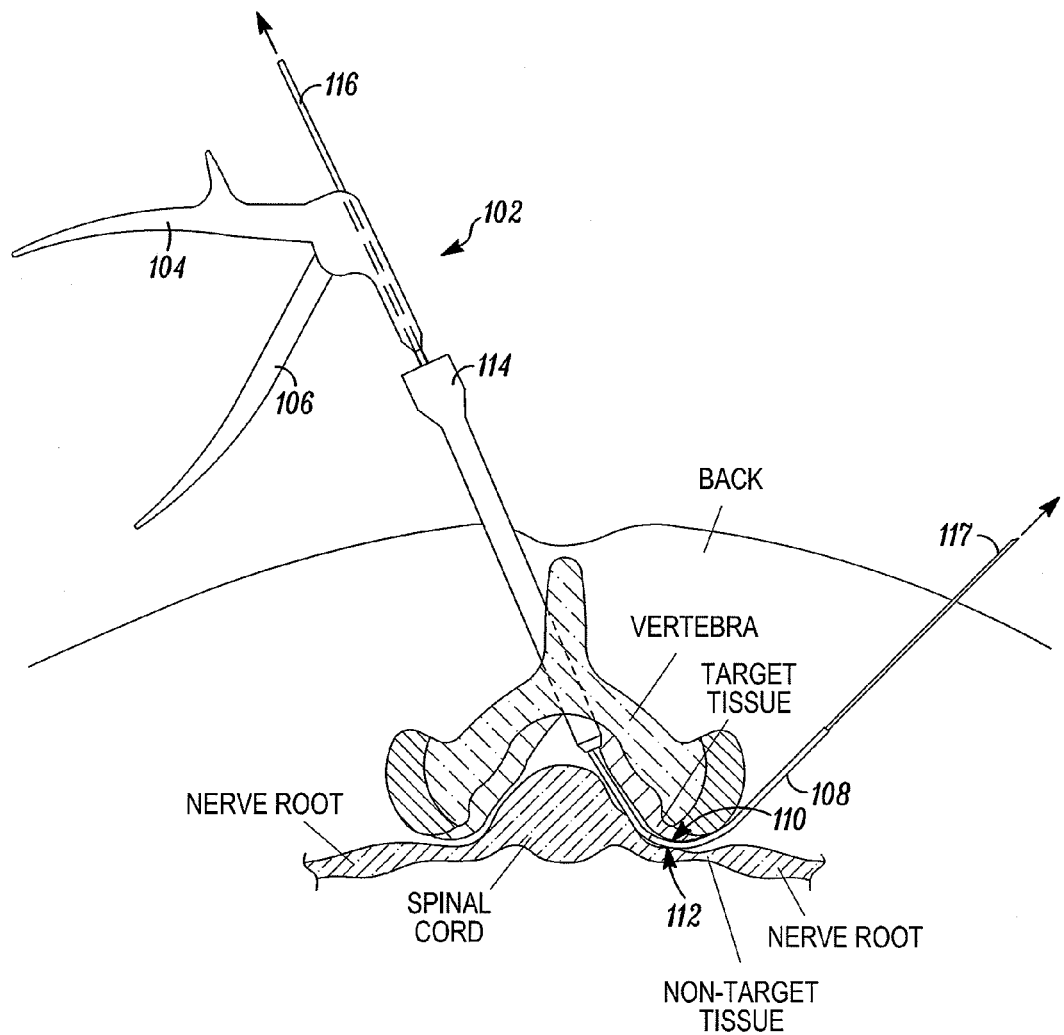
Figure 7S:
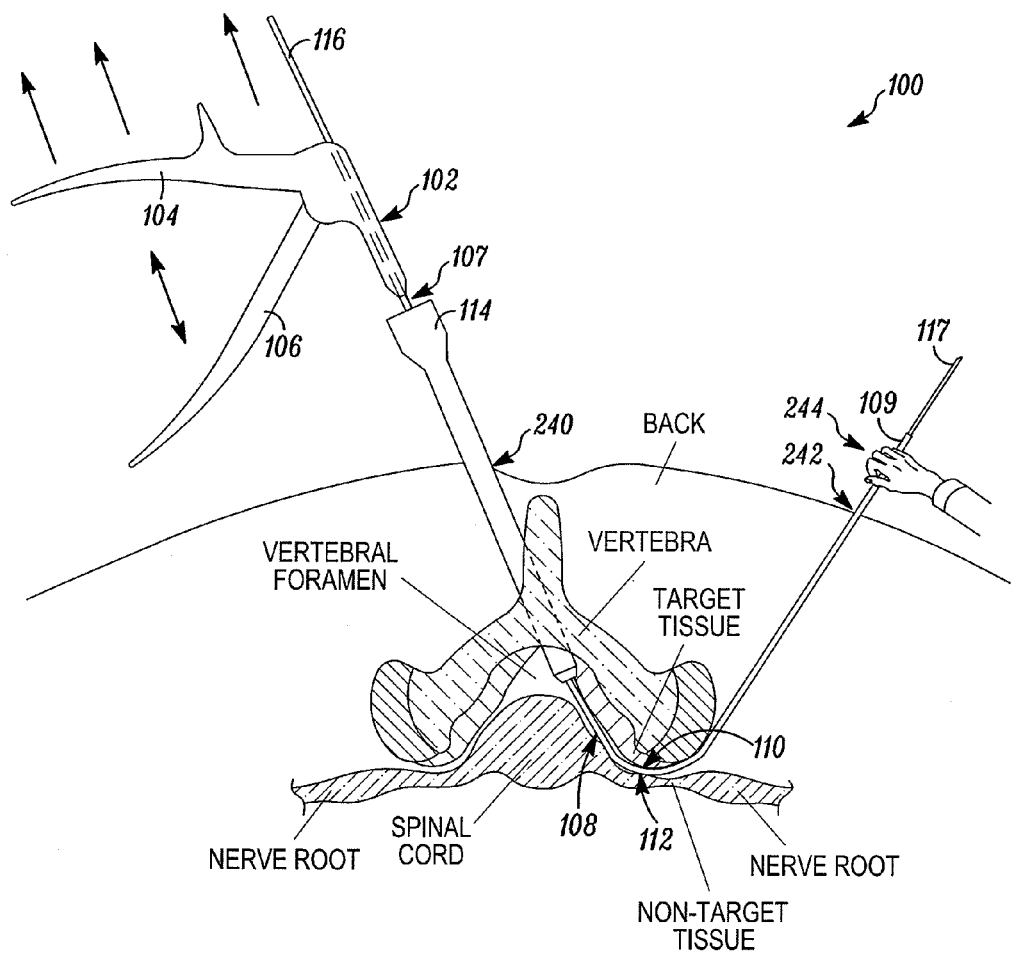

Referring now to FIGS. 7A-7S, a system and method for introducing a tissue modification device into a spine is demonstrated. This system and method may be referred to as an "access system" or "access method," in that they provide or facilitate gaining access to a target tissue to be modified. Of course, the embodiment shown is merely one exemplary embodiment, and any of a number of other suitable methods, devices or systems may be used to introduce one or more devices for modifying tissue in spine. For example, in one alternative embodiment a spinal tissue modification procedure may be carried out through an open surgical approach. Therefore, the following description is provided primarily for exemplary purposes and should not be interpreted to limit the scope of the invention as it is defined in the claims.

Referring to FIG. 7A, in one embodiment a device delivery method first involves advancing an introducer cannula 300 coupled with a stylet 302 into the patient's back. Cannula 300 and stylet 302 are then passed between adjacent vertebrae and into the ligamentum flavum or an adjacent spinal ligament, as shown further in FIG. 7B. As shown in FIG. 7C, when the distal tip of cannula is positioned as desired, stylet 302 is removed. Referring to FIGS. 7D and 7E, a loss of resistance syringe 304 including a plunger 310, barrel 308 and fluid and/or air 306, is coupled with the proximal portion of cannula 300. The distal portion of cannula 300 is advanced through the ligamentum flavum until it enters the central spinal canal where a loss of resistance to pressure placed on plunger 310 is encountered, and fluid and/or air 306 is injected into central spinal canal to confirm correct placement of cannula 300 as shown in FIG. 7E. Syringe 304 is then removed, as in FIG. 7F, and a guidewire 312 with a non-rigid, atraumatic tip is advanced through cannula 300 into the central spinal canal, as in FIG. 7G. Next, cannula 300 is removed, as in FIG. 7H, leaving behind guidewire 312. As shown in FIGS. 7I and 7J, an introducer sheath 114, coupled with a dilator 314, is then advanced over guidewire 312 to position a distal portion of sheath 114 at a desired location within the spine. Dilator 314 and guidewire 312 are then removed, as in FIG. 7K.

Once introducer sheath 114 is in place, one or more curved or steerable guide devices 318 may be advanced through it to desired positions in and/or through the spine, as shown in FIGS. 7L and 7M. One or more guide members 116, may then be advanced through the guide device 318, as shown in FIGS. 7N-7P. Finally, guide device 318 may be removed, as in FIG. 7Q, and elongate body 108 of tissue modification device 102 may be advanced over guide member 116 and through introducer sheath 114 to a desired position in the spine, as in FIG. 7R. As shown in FIG. 7S, elongate body 108 may be tensioned to urge tissue modifying members 110 against target tissue, as shown with arrows at opposite ends of device 102, while distal portion 109 is anchored, in this case by hand 244. In an alternative embodiment, guide member 116 may be tensioned to urge tissue modifying members 110 against target tissue as shown in FIG. 7R.

Once tissue modification device 102 is in a desired position, tissues which may be modified in various embodiments include, but are not limited to, ligament, tendon, tumor, cyst, cartilage, scar, "bone spurs," inflammatory and bone tissue. In some embodiments, modifying the target tissue reduces impingement of the tissue on a spinal cord, a branching nerve or nerve root, a dorsal root ganglia, and/or vascular tissue in the spine. Actuator 106 on handle 104 is activated to modify target tissue using tissue modification member(s) 110, while elongate body 108 is held relatively stable by hand 244 and by tension force applied to handle 104.

In various embodiments, the system and method described immediately above may include additional features or steps, may have fewer features or steps, may have an alternate order of implementation of steps, or may have different features or steps. For example, in some embodiments placement of device 102 will be performed in a medial-to-lateral direction (relative to the patient), while in alternative embodiments device placement will be performed lateral-to-medial. In some embodiments, one or more components of the system described may be anchored to the patient, such as guide member 116 or introducer sheath 114. In various embodiments, one or more guide members 116 may include one or more wires, rails or tracks and may be inserted through guide device 318, introducer sheath 114 without guide device 318, cannula 300, an epidural needle, a lumen of an endoscope, a lumen of a tissue shield or barrier device, a curved guide device 318 placed through a lumen of an endoscope, or the like. In other embodiments, for example, guide device 318 may be placed through introducer cannula 300 and then introducer sheath 114 may be passed over guide device 318. Tissue modification device 102 may similarly be inserted with or without using any of these devices or components in various combinations. Various guidewires 312, guide devices 318 and/or guide members 116 may be pre-shaped to have one or more curves, may be steerable, and/or may include one or more rails, tracks, grooves, lumens, slots, partial lumens, or some combination thereof.

In some embodiments, tissue modification device 102 is inserted through one or more hollow devices as described above (such as introducer sheath 114, as shown, or cannula 300 in an alternative embodiment) in such a way that device 102 expands upon extending out of a distal portion of the hollow delivery device thereby assuming a wider profile for modifying a greater amount of target tissue from a single location. In an alternative embodiment, device 102 retains the same overall profile during insertion and during use. In some embodiments, one or more delivery devices will remain in the patient during use of tissue modification device 102, while in alternative embodiments all delivery devices are removed from the patient when tissue modification device 102 is operating. In some embodiments, tissue modification device 102 may be slidably coupled with one or more delivery devices during delivery and/or during use. In one embodiment, tissue modification device 102 is advanced through introducer sheath 114 and sheath 114 is used as an irrigation and evacuation lumen to irrigate the area of the target tissue and evacuate removed tissue and other debris, typically by applying a vacuum. In alternative embodiments, tissue modification device 102 may include an irrigation and/or evacuation lumen to irrigate an area of the target tissue and evacuate removed tissue and other debris.

Some embodiments of an access system for facilitating tissue modification may further include one or more visualization devices (not shown). Such devices may be used to facilitate placement of the access system for introducing the tissue modification device, to facilitate tissue modification itself, or any combination of these functions. Examples of visualization devices that may be used include flexible, partially flexible, or rigid fiber optic scopes, rigid rod and lens endoscopes, CCD or CMOS chips at the distal portion of rigid or flexible probes, LED illumination, fibers or transmission of an external light source for illumination or the like. Such devices may be slidably couplable with one or more components of an access system or may be slidably or fixedly coupled with a tissue modification device. In other embodiments, additional or alternative devices for helping position, use or assess the effect of a tissue modification device may be included. Examples of other such devices may include one or more neural stimulation electrodes with EMG or SSEP monitoring, ultrasound imaging transducers external or internal to the patient, a computed tomography (CT) scanner, a magnetic resonance imaging (MRI) scanner, a reflectance spectrophotometry device, and a tissue impedance monitor disposed across a bipolar electrode tissue modification member or disposed elsewhere on a tissue modification device or disposed on the access system.

Figure 8A:
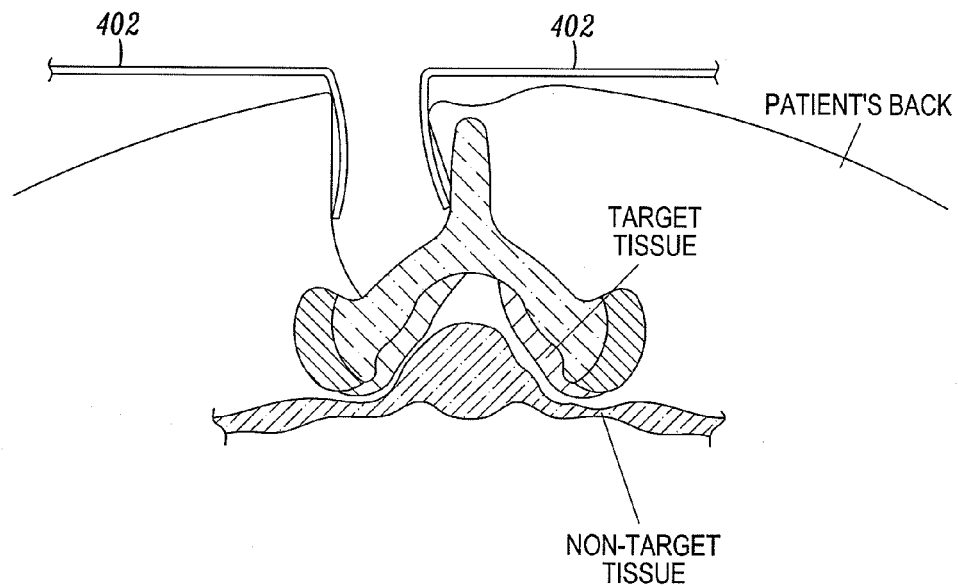
FIGS. 8A-8F are cross-sectional views of a portion of a patient's spine and back, demonstrating a method for introducing apparatus for modifying spinal tissue to an area in the spine for performing the tissue modification according to an alternative embodiment of the present invention.
Figure 8B:
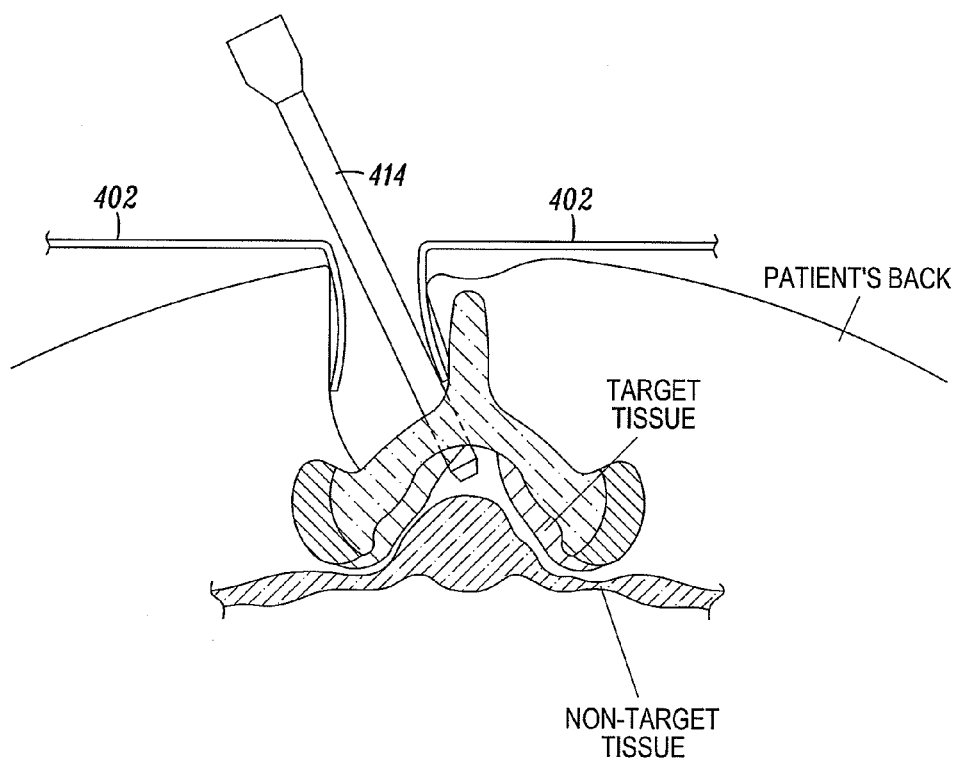
Figure 8C:
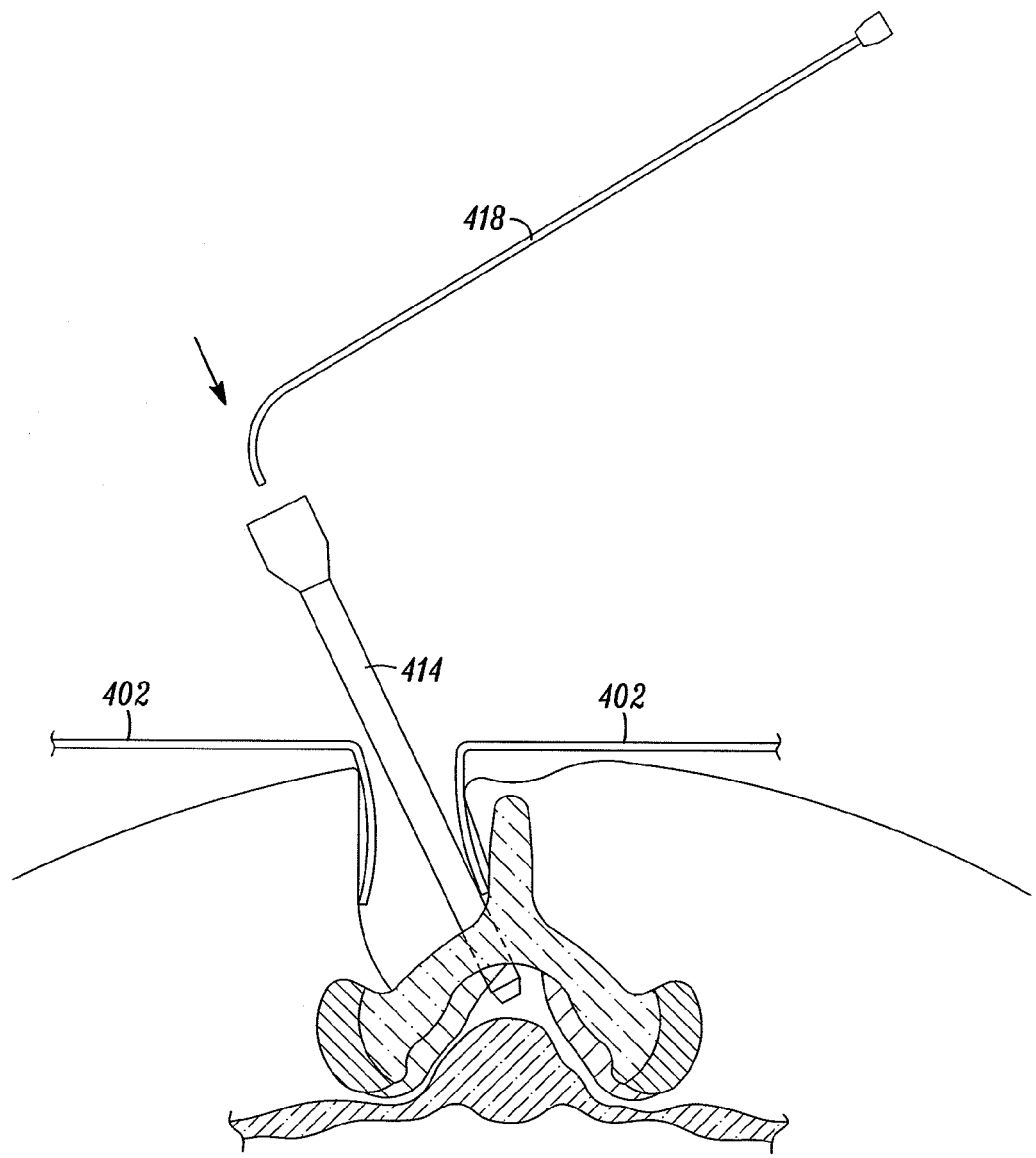
Figure 8D:
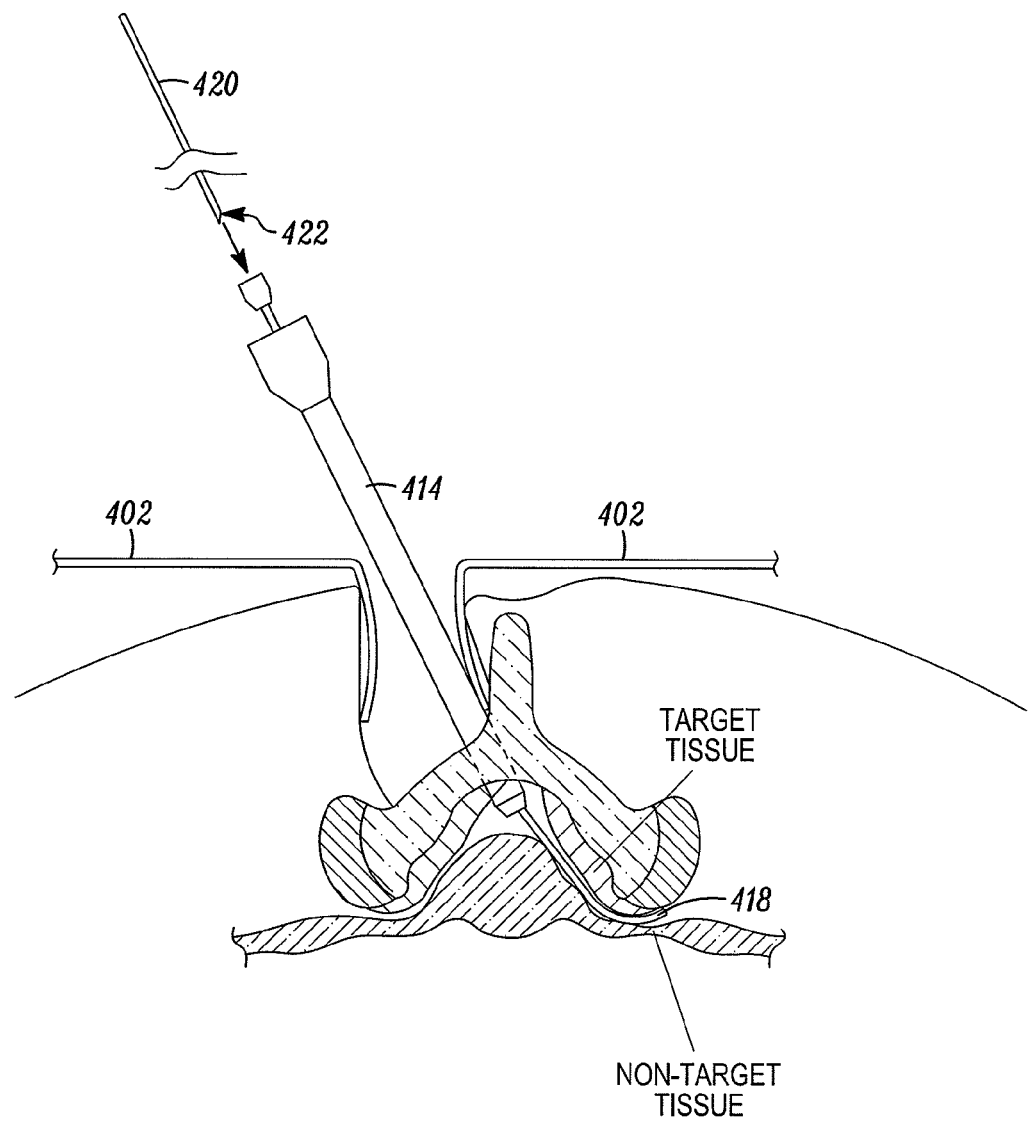

Referring now to FIGS. 8A-8E, in an alternative embodiment, a tissue modification device and optionally one or more introduction/access devices may be positioned in a patient using an open surgical technique. As shown in FIG. 8A, for example, in one embodiment an open surgical incision is made on a patient's back, and two retractors 402 are used to expose a portion of the patient's vertebra. As shown in FIG. 8B, an introducer sheath 414 may then be inserted through the incision, between retractors 402. As in FIG. 8C, a curved guide device 418 may then be inserted through introducer sheath 414. Guide device 418 extends into the epidural space and through the intervertebral foramen as shown in FIG. 8D.

In some embodiments, a curved and cannulated thin, blunt probe may be placed directly through the open incision into the epidural space of the spine, or alternatively may be placed through introducer sheath 414. The probe tip may be advanced to or through a neural foramen. Such a probe may be similar in shape, for example, to a Woodson elevator, Penfield 3, hockey stick probe, ball tipped probe, or the like. In alternative embodiments, probes that may be manually bent to change their shapes, or probes with articulating tips, or probes with shape lock portions, and/or probes having grooves instead of cannulas may be used.

Figure 8E:
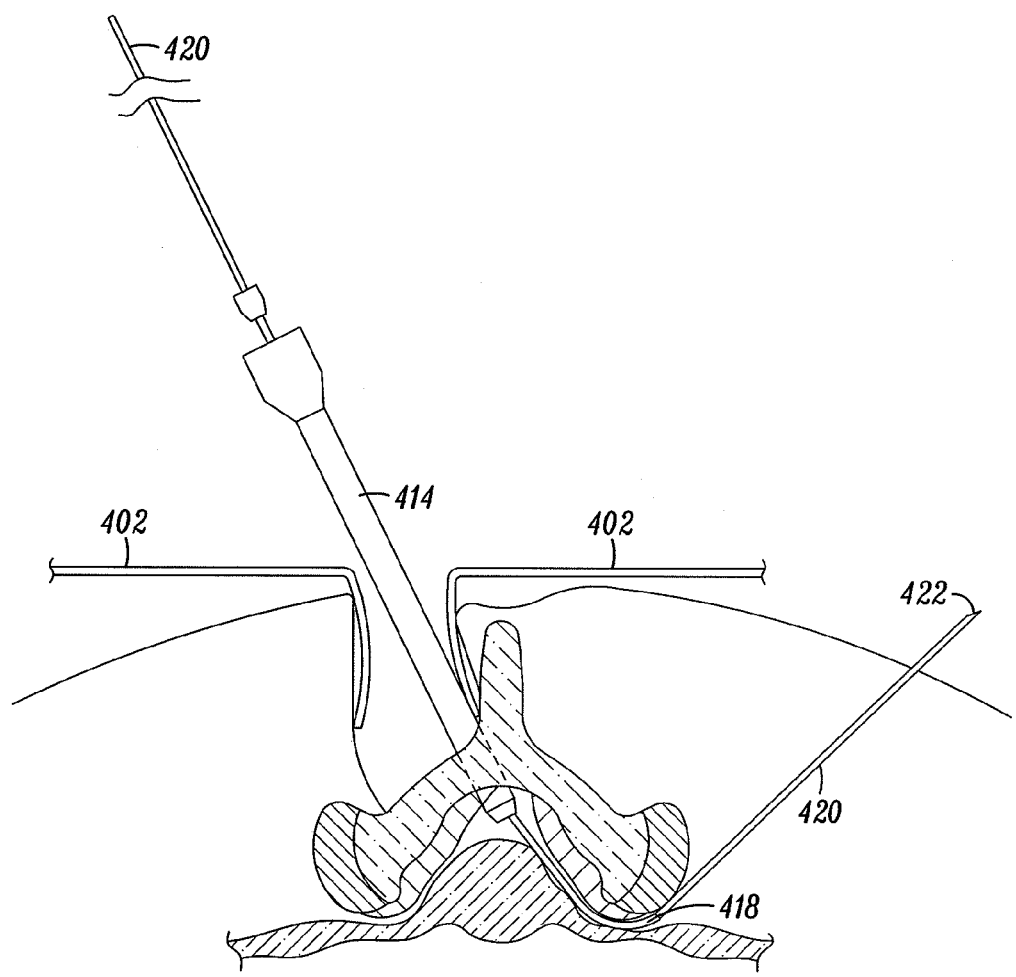
Figure 8F:
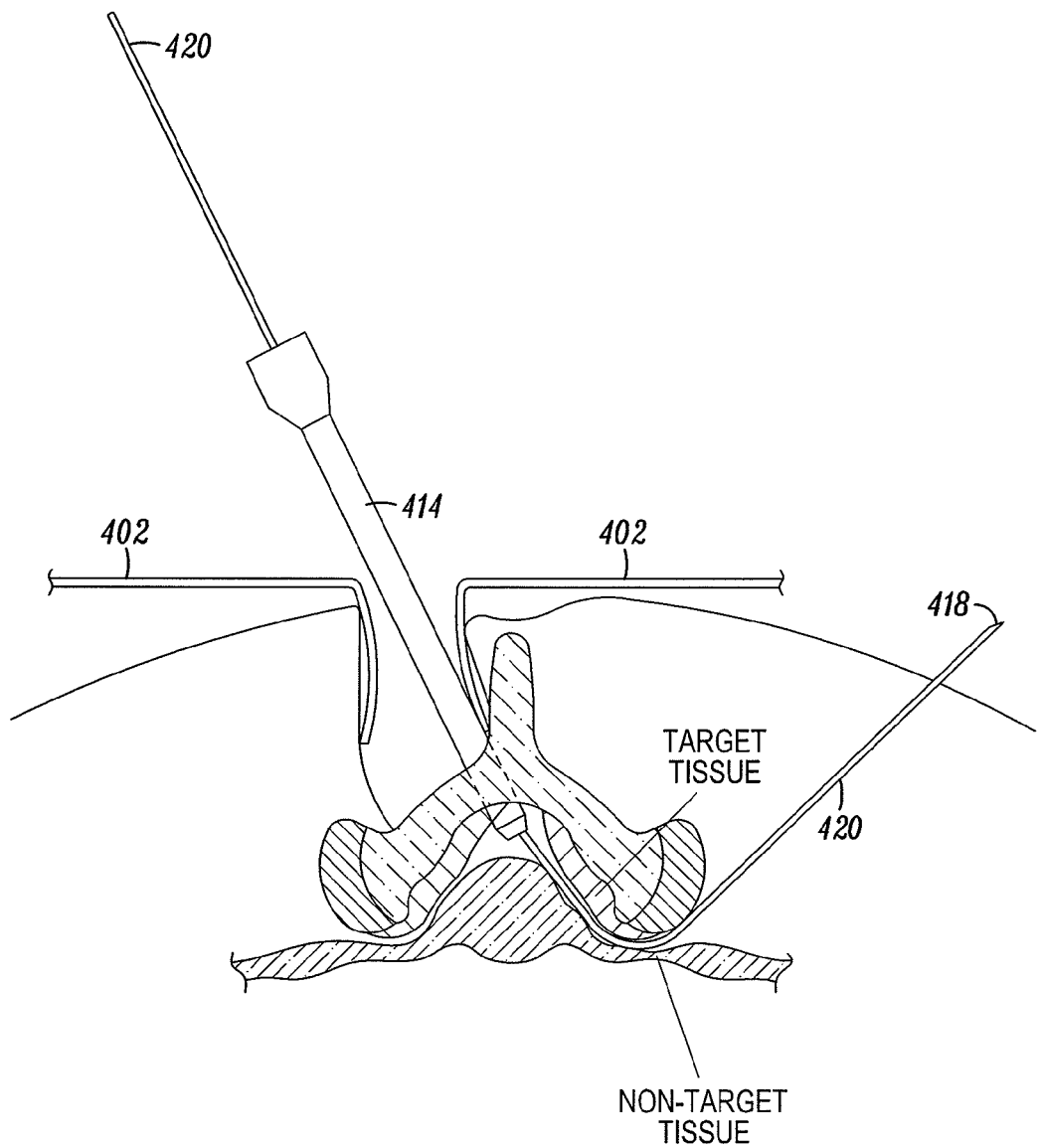

As shown in FIGS. 8D-8E, a substantially straight, flexible guidewire 420 with a sharp tip 422 may then be inserted through curved guide device 418 and advanced so that its distal portion with sharp tip 422 extends outside the patient's back at a location separate from the open incision (FIG. 8E). Guide device 418 may then be removed, as in FIG. 8F, and in subsequent steps a tissue modification device may be inserted over guide wire 420 and through introducer sheath 414 and used to modify tissue as described in more detail above. In an alternative embodiment, a curved, flexible cannula may be inserted through the curved guide device, until it extends lateral to the neural foramen, after which a substantially straight, flexible guidewire with a sharp tip may then be inserted through curved cannula and advanced so that its distal portion with sharp tip extends outside the patient's back.

Figure 9A:
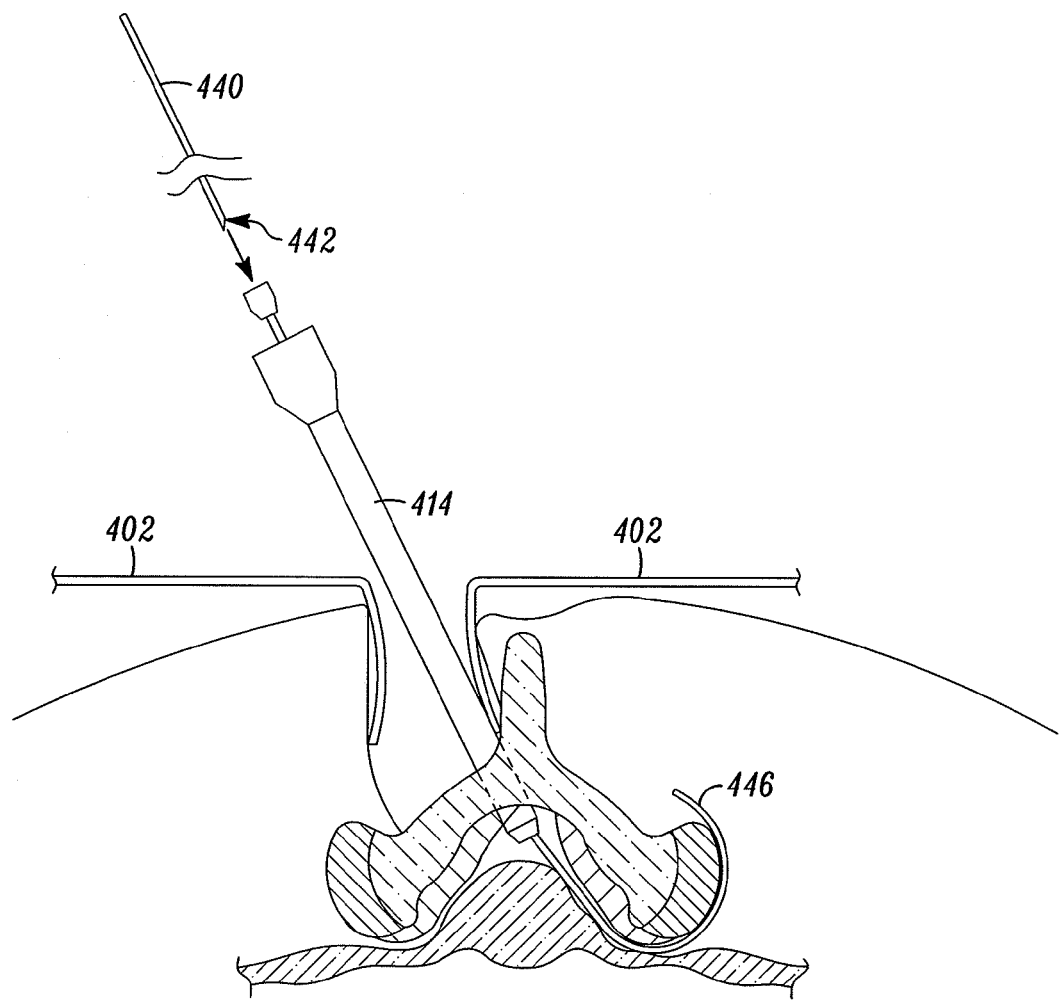
FIGS. 9A-9B are cross-sectional views of a portion of a patient's spine and back, demonstrating a method for introducing apparatus for modifying spinal tissue to an area in the spine for performing the tissue modification according to an alternative embodiment of the present invention.
Figure 9B:
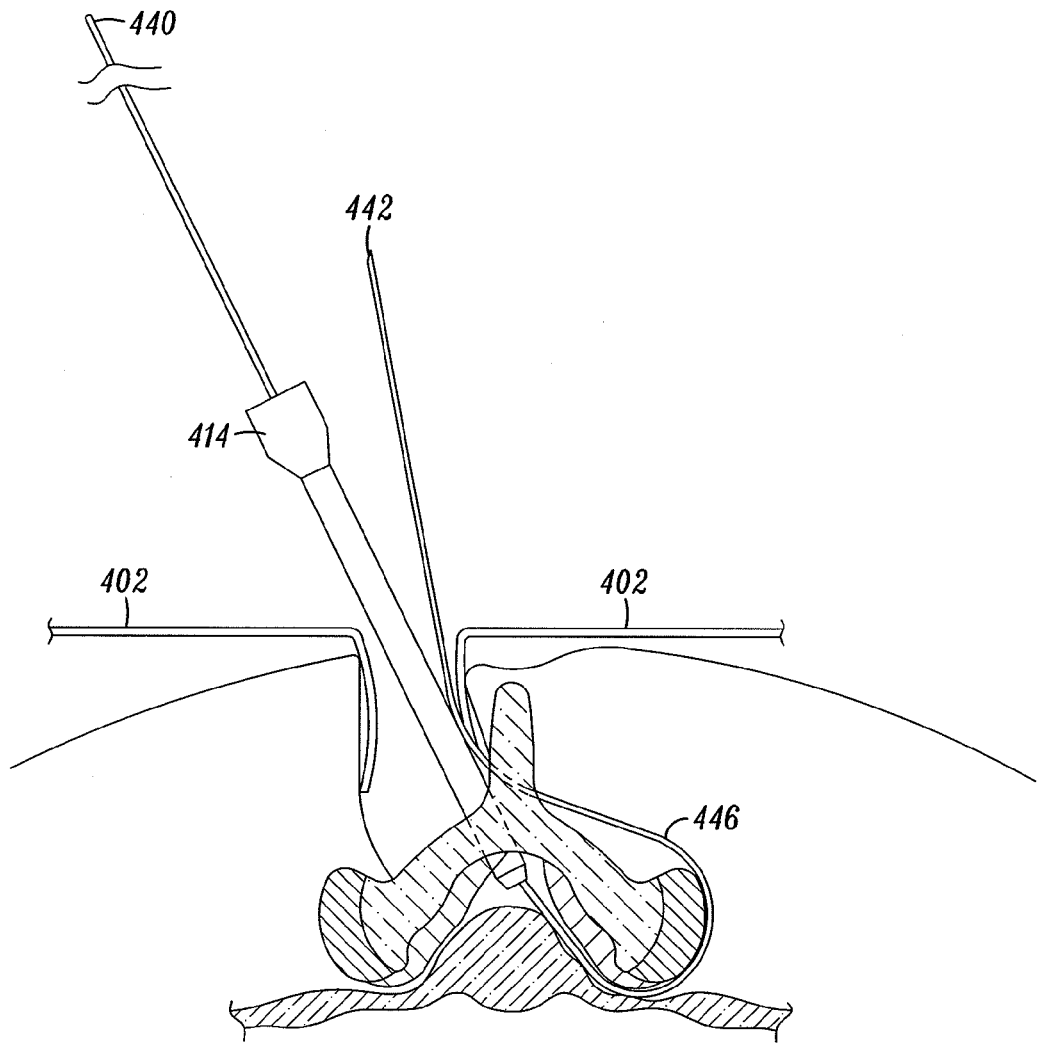

Referring now to FIGS. 9A and 9B, another alternative open surgical access method is shown. In FIG. 9A, a curved guide device 446 is shown in place through the epidural space and intervertebral foramen, and a guidewire 440 with a beveled distal tip 442 is about to be advanced through guide device 446. As shown in FIG. 9B, in this embodiment, guidewire 440 is directed by guide device 446 back through the open incision through which the various access devices are introduced. In such an embodiment, then, only one incision is created and the proximal and distal portions of one or more devices extend out of the patient's back through the same incision.

In various alternative embodiments, open surgical access may be through exposure down to a vertebral lamina, through ligamentum flavum without lamina removal, through ligamentum flavum with partial or complete lamina removal, through ligamentum flavum with or without lamina removal with partial or complete medial facet joint removal, through open exposure and out through skin laterally, through open exposure and back out through the open exposure, or through a lateral open exposure that accesses the neural foramen from the lateral side. One or more visualization devices may be used with open surgical access procedures as well as with percutaneous or other less invasive procedures. In another alternative embodiment (not shown), a tissue modification device may be placed in the patient directly, without any introduction devices.

Referring now to FIGS. 10A-10E, in the embodiments described above, the tissue modification devices 102, 202 include at least one non-tissue-modifying (or "protective") portion, side or surface. The non-tissue-modifying portion is located on tissue modification device 102, 202 so as to be positioned adjacent non-target tissue when tissue modifying members 110, 210 are facing the target tissue. The non-tissue-modification surface of the device is configured so as to not modify or damage tissue, and thus the non-target tissue is protected from unwanted modification or damage during a tissue modification procedure. Alternatively, in some embodiments, a protective surface or portion of tissue modification device 102, 202 may actually modify non-target tissue in a protective manner, such as by delivering a protective drug, coating, fluid, energy or the like to the non-target tissue.

Optionally, in some embodiments, tissue modification devices or systems may further include one or more tissue barriers (or "shields") for further protecting non-target tissues. Such barriers may be slidably coupled with, fixedly coupled with, or separate from the tissue modification devices with which they are used. In various embodiments, a barrier may be delivered between target and non-target tissues before delivering the tissue modification device, may be delivered along with the tissue modification device, or may be delivered after delivery of the tissue modification device but before the device is activated or otherwise used to modify target tissue. Generally, such a barrier may be interposed between the non-target tissue and one or more tissue modification devices to prevent unwanted damage of the non-target tissue.

Figure 10A:
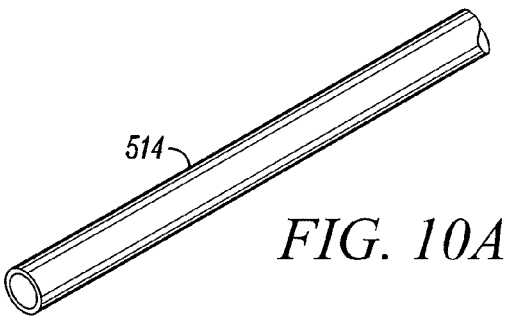
FIG. 10A is a perspective view of a distal portion of an introducer sheath according to one embodiment of the present invention.
Figure 10B:
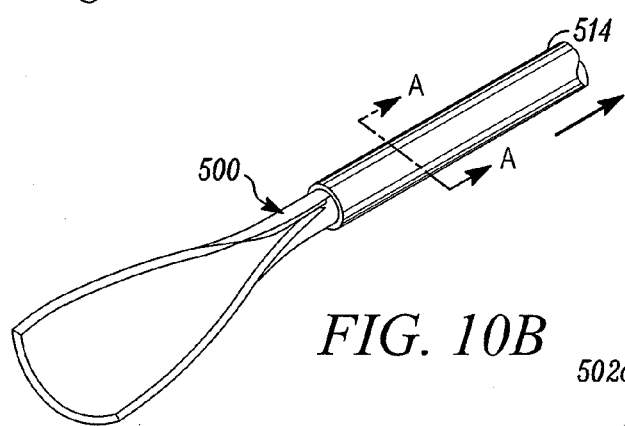
FIGS. 10B and 10C are perspective and cross-sectional views, respectively, of a tissue shield device according to one embodiment of the present invention.
Figure 10C:
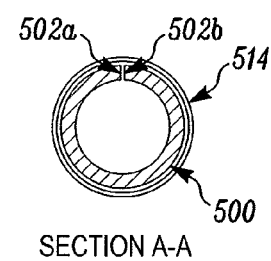
Figure 10D:
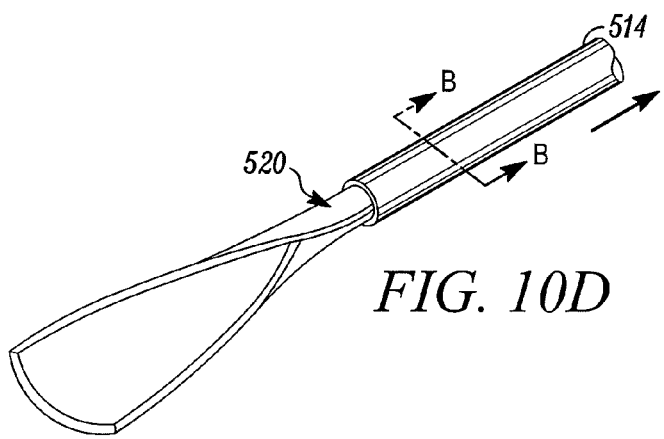
FIGS. 10D and 10E are perspective and cross-sectional views, respectively, of a tissue shield device according to an alternative embodiment of the present invention.
Figure 10E:
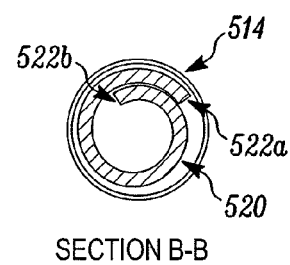

FIG. 10A shows a distal portion of an introducer device 514 through which a barrier may be introduced. FIGS. 10B and 10C show one embodiment of a barrier 500 partially deployed and in cross-section, respectively. Typically, barrier 500 will have a first, small-profile configuration for delivery to an area near non-target tissue and a second, expanded configuration for protecting the non target tissue. In various embodiments, some of which are described more fully below, barrier 500 may be configured as one piece of super-elastic or shape-memory material, as a scaffold with material draped between the scaffolding, as a series of expandable wires or tubes, as a semicircular stent-like device, as one or more expandable balloons or bladders, as a fan or spring-loaded device, or as any of a number of different devices configured to expand upon release from delivery device 514 to protect tissue. As shown in FIGS. 10B and 10C, barrier 500 may comprise a sheet of material disposed with a first end 502a abutting a second end 502b within introducer device 514 and unfurling upon delivery. In an alternative embodiment, as shown in FIGS. 10D and 10E, opposite ends 522a and 522b of a barrier 520 may overlap in introducer device 514. Generally, barrier 500, 520 may be introduced via introducer device 514 in one embodiment or, alternatively, may be introduced via any of the various means for introducing the tissue modification device, such as those described in conjunction with FIGS. 7A-7S, 8A-8F and 9A-9B. In some embodiments, barrier 500, 520 may be fixedly coupled with or an extension of a tissue modification device. Barrier 500, 520 may also include one or more lumens, rails, passages or the like for passing a guidewire or other guide member, for introducing, removing or exchanging any of a variety of tissue modification, drug delivery, or diagnostic devices, for passing a visualization device, for providing irrigation fluid at the tissue modification site, and or the like. In some embodiments, barrier 500, 520 is advanced over multiple guidewires and the guidewires remain in place during a tissue modification procedure to enhance the stability and/or maintain positioning of barrier 500, 520.

Figure 11A:
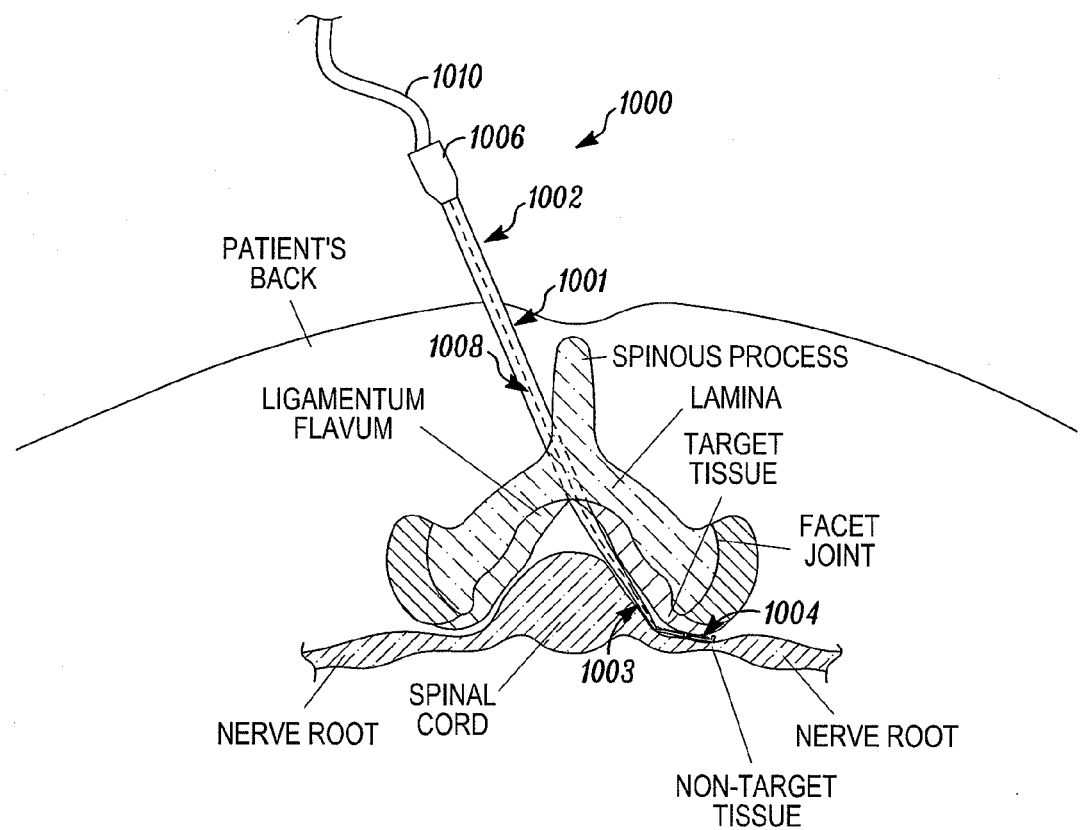
FIGS. 11A and 11B are cross-sectional views of a spine with a tissue modification device in position for modifying tissue according to various embodiments of the present invention.
Figure 11B:
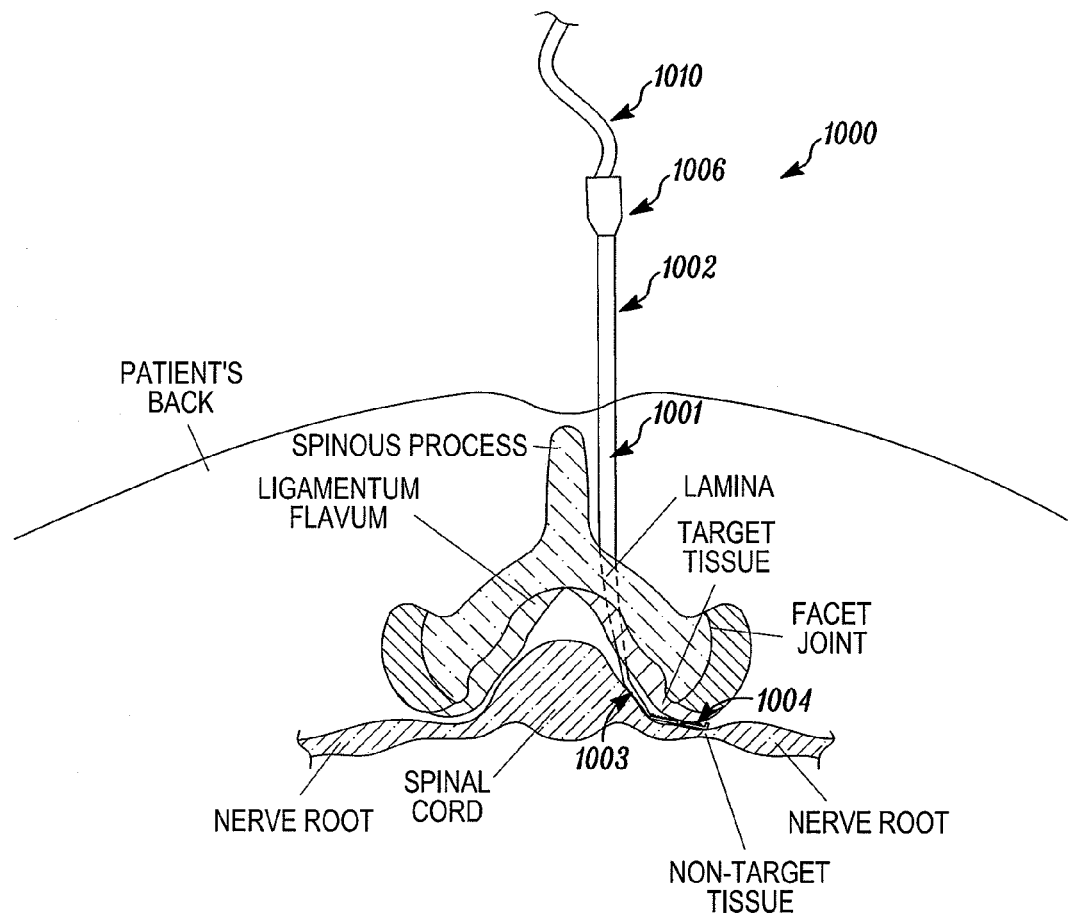

Referring now to FIGS. 11A and 11B, in an alternative embodiment, a powered tissue modification device 1000 suitably includes an elongate shaft 1001 having a proximal portion 1002, a distal portion 1003 and a longitudinal axis 1008, one or more tissue modifying members 1004 coupled with shaft 1001 at or near distal portion 1003, and a handle 1006 coupled with shaft 1001 at or near proximal portion 1002. Optionally, some embodiments may also include one or more power connectors 1010 for connecting device 1000 with one or more power sources. In some embodiments, shaft 1001 has a size and shape that facilitate passage of at least distal portion 1003 into an epidural space of the spine and between target tissue, such as ligamentum flavum, and non-target tissue, such as neural and/or neurovascular tissue. In some embodiments, shaft 1001 may include one or more bends or curves at or near its distal portion 1003 to further facilitate passage and positioning of device 1000. In some embodiments, for example, a bend or curve may facilitate passage of at least part of distal portion 1003 at least partway into an intervertebral foramen.

In some embodiments, as shown in FIG. 11A, distal portion 1003 of device 1000 may be advanced through the skin of the back of a patient, adjacent a spinous process. Distal portion 1003 may then be advanced between the lamina of adjacent vertebral bodies, into the epidural space, and between target and non-target tissues to position tissue modifying member(s) 1004 in a desired location for modifying target tissue. Power may then be provided to activate tissue modifying member(s) 1004 and thus to modify target tissue. A portion of device 1000 adjacent tissue modifying member(s) 1004 may be configured to face non-target tissue while tissue modifying member(s) 1004 face the target tissue, thus preventing unwanted damage or modification of the non-target tissue. In some embodiments, as described more fully above, the portion of device 1000 facing the non-target tissue may be configured to modify the non-target tissue in some way, such as to protect the tissue with a delivered substance, and/or to test the non-target tissue to confirm that it is non-target tissue.

In various embodiments, handle 1006 may have any suitable configuration and features. In some embodiments, handle 1006 includes one or more actuators for activating tissue modifying member(s) 1004. Power connector 1010 may have any suitable configuration and may deliver any suitable type of energy from an external power source (not shown) to device 1000 in various embodiments, such as but not limited to electric, radiofrequency, ultrasound, laser or conductive energy. In alternative embodiments, device 1000 may be battery operated or use any other suitable source of internal power or energy, and such internal energy source may be housed in handle 1006, for example. From whatever source, power is typically transmitted to tissue modifying member(s) 1004 to activate them and thus modify tissue.

With reference now to FIG. 11B, in various embodiments, tissue modification device 1000 may be advanced into a patient using any of a number of suitable techniques and approaches, some of which have been described previously. FIG. 11A illustrates one approach to advancing distal portion 1003 of device 1000 to a position between target and non-target tissue from a contralateral approach, while FIG. 11B illustrates an ipsilateral approach. As shown in FIG. 11B, distal portion 1003 may include two or more bends and/or may be at least partially flexible or steerable to facilitate a desired approach angle, according to various embodiments.

Figure 12:
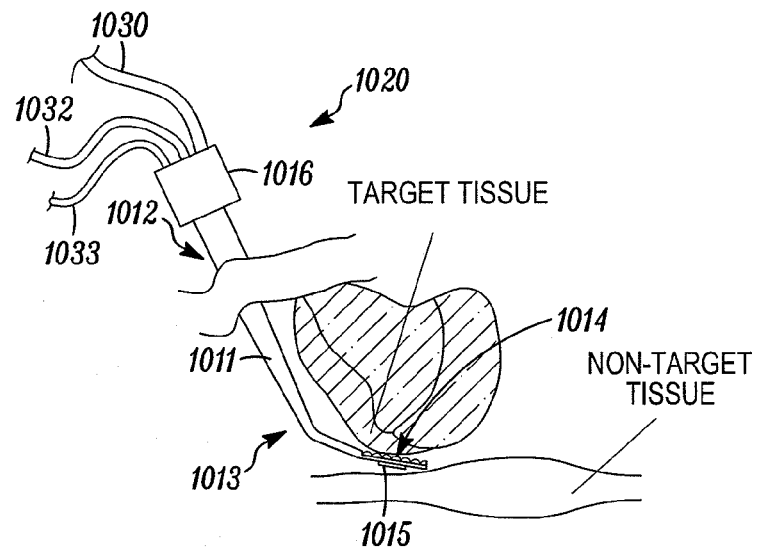
FIG. 12 is a cross-sectional view of a portion of a spine with a tissue modification device in position for modifying tissue according to an alternative embodiment of the present invention.

Turning to FIG. 12, in another embodiment a tissue modification device 1020 includes an elongate shaft 1011 having a proximal portion 1012 and a distal portion 1013, one or more tissue modification member(s) 1014, a conductive electrode 1015 coupled with shaft 1011, a handle 1016, a power connector 1030, and multiple additional connection members 1032, 1033. Electrode 1015 may be configured to deliver a non-target frequency and non-target amplitude of electrical current to non-target tissue. The non-target frequency and non-target amplitude may stimulate a response from a neural tissue. In one embodiment, a first connection member 1032 may provide power to electrode 1015, and if non-target-tissue is stimulated by current from the electrode, the observation of this stimulation, as measured by EMG, SSEP or watching for muscular activation, provides evidence that electrode 1015 is adjacent the non-target tissue. A target stimulating electric current may also be delivered through second connection member 1033 to tissue modifying member(s) 1014 (e.g., composed of electrically conductive material) and/or to a target stimulating electrode located adjacent and on the same side of device 1020 as tissue modifying member(s) 1014. For example, if the target simulating electric current is configured with a frequency and amplitude to stimulate a response from neural tissue, the type (e.g., neural, non-neural) of the tissue immediately adjacent tissue modifying member(s) 1014 may be determined based on the tissue response or lack thereof. In one embodiment, device 1020 may be configured to allow for control of the target stimulating electric current and the non-target stimulating electric current. For example, the target stimulating electric current and the non-target stimulating electric current may be sequentially delivered to distal portion 1013 of device 1020 to determine the location of neural tissue prior to activation of tissue modifying member(s) 1014, for example, to help ensure that tissue modifying member(s) 1014 do not damage neural tissue.

In various embodiments, tissue modifying member(s) 1014 may include one or more of a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode, a rotary powered mechanical shaver, a reciprocating powered mechanical shaver, a powered mechanical burr, a laser, an ultrasound crystal, a cryogenic probe, a pressurized water jet, or some combination thereof. Some embodiments include one tissue modifying member 1014, while others include multiple tissue modifying members 1014. As is described further below, tissue modifying member(s) 1014 may have any of a number of suitable sizes, shapes and configurations and may move or actuate in any suitable way.

Figure 13A:
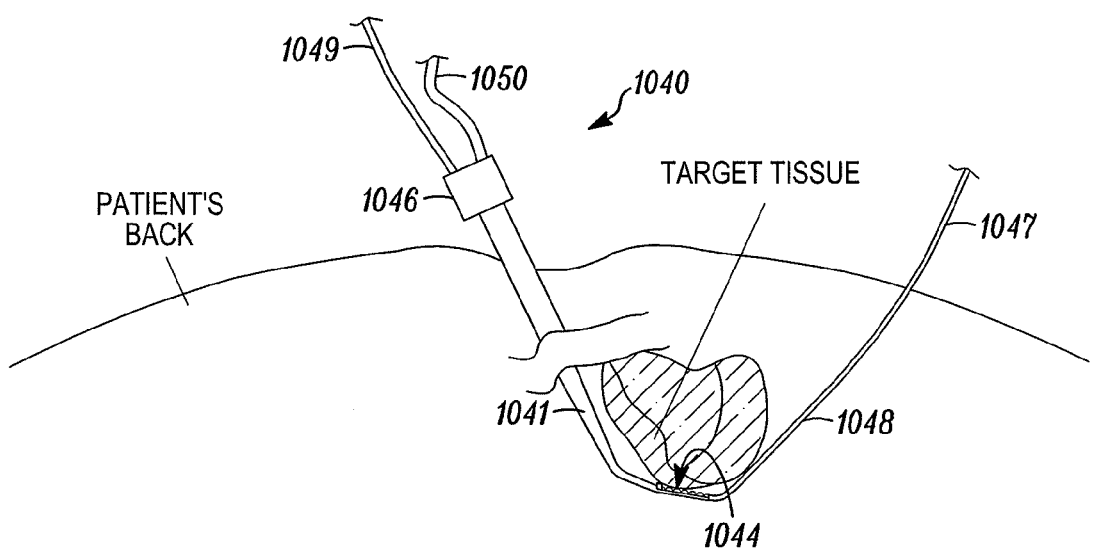
FIGS. 13A-13E are cross-sectional views of a portion of a spine with a tissue modification device in position for modifying tissue according to various alternative embodiments of the present invention.

Referring now to FIG. 13A, in an alternative embodiment, a tissue modification device 1040 includes an elongate shaft 1041, one or more tissue modifying member(s) 1044, a handle 1046 and a power connector 1050. Additionally, device 1040 may include a guidewire lumen (not shown) extending through all or part of shaft 1041, which may allow passage of a guidewire 1048 having proximal 1049 and distal 1047 ends therethrough. In one embodiment, for example, guidewire 1048 may extend from a proximal end of shaft 1041 through a distal end of shaft 1041 and out the patient. In some embodiments, as described previously above, anchoring and/or tensioning force may be applied at or near distal end 1047 and/or proximal end 1049 to help urge tissue modifying member(s) 1044 against target tissue.

Figure 13B:
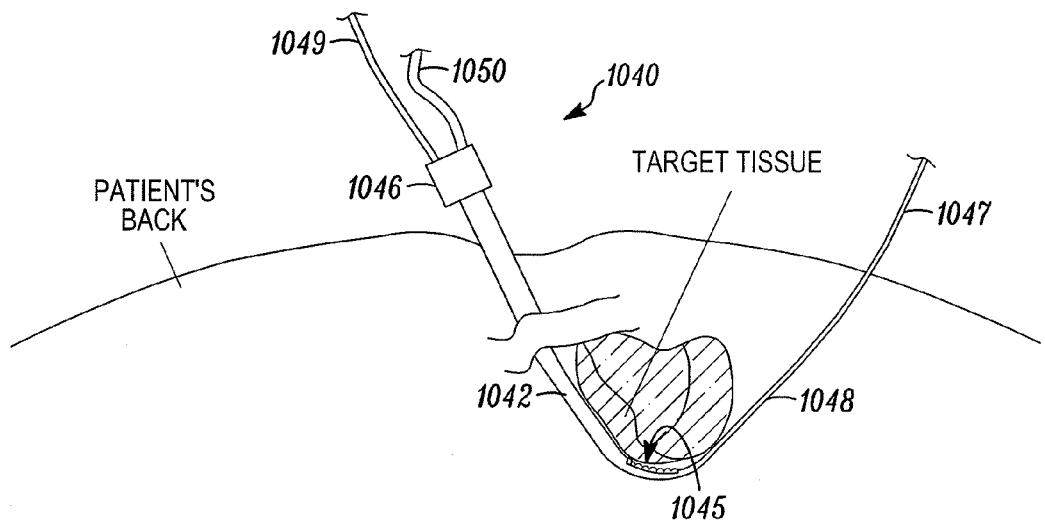

In the embodiment shown in FIG. 13A, tissue modifying member 1044 is shown having relatively flat configuration. In many of the subsequent embodiments described herein, various embodiments of tissue modifying members are also shown as having flat configurations, primarily for ease of description. In alternative embodiments, however, and with reference now to FIG. 13B, tissue modification device may include a curved and/or flexible tissue modifying member 1045 (or multiple curved and/or flexible members), having a curved/flexible surface for contacting target tissue. Device 1040 may also include a curved and/or flexible shaft 1042. Such curved and/or flexible tissue modifying members 1045 (or tissue modifying surfaces) and shafts 1042 may facilitate tissue modification in some embodiments, in that tissue modifying members 1045 may more readily conform to target tissue. In alternative embodiments, many if not all of the devices described in the present application may have such curved and/or flexible tissue modifying member(s).

Figure 13C:
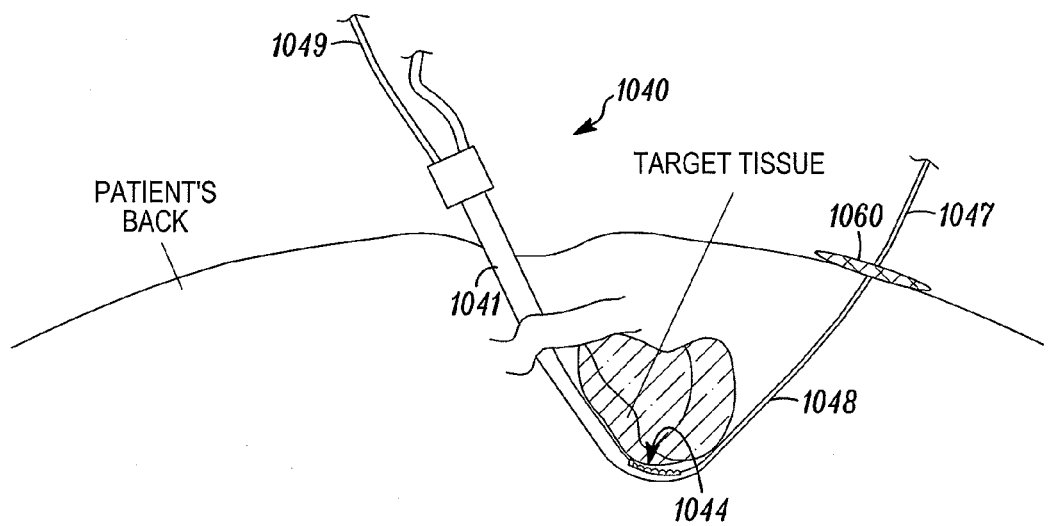
Figure 13D:
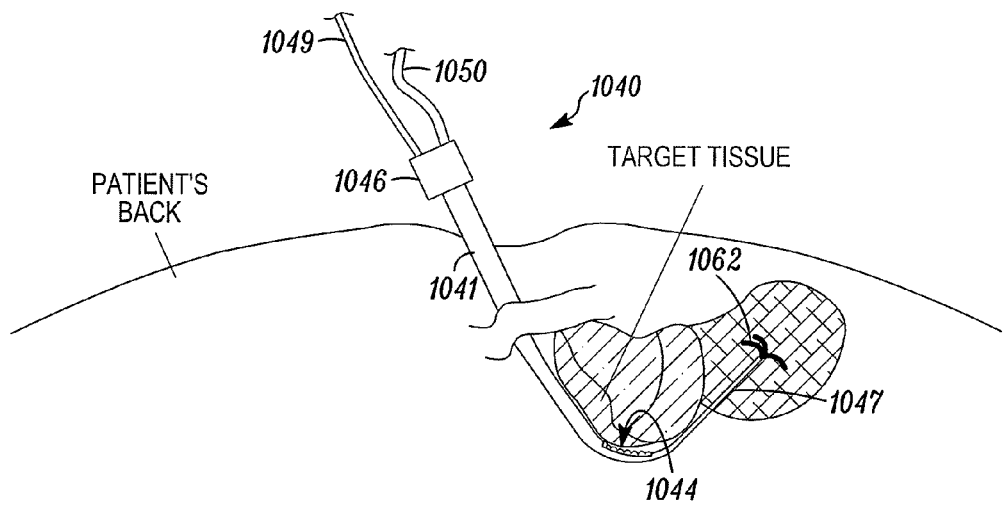
Figure 13E:
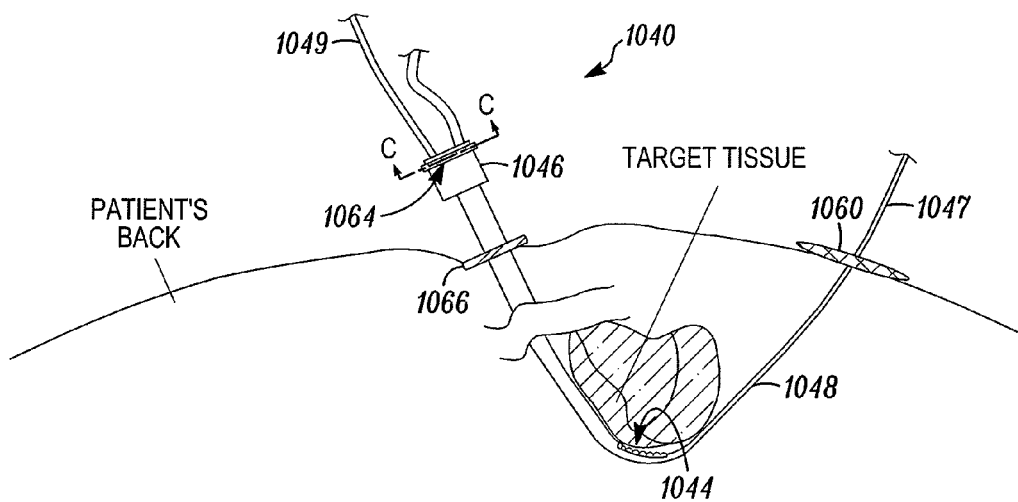

Referring now to FIGS. 13C-13E, several alternative embodiments of anchoring members for use with a tissue modification device are shown. FIG. 13C, for example, shows tissue modification device 1040 including a wire anchor 1060 coupled with guidewire 1048. In various embodiments, wire anchor 1060 may be either removably or permanently attached to guidewire 1048 at or near its distal end 1047 to provide anchoring force against the patient's back from outside the patient. Wire anchor 1060 may minimize or prevent guidewire 1048 from moving through the patient's back towards proximal end 1049. In alternative embodiments, additional anchoring and/or tensioning force may be applied to distal end 1047, such as by holding and/or pulling distal end 1047 by hand.

In an alternative embodiment, as shown in FIG. 13D, distal end 1047 of guidewire 1048 may include one or more deployable anchoring members 1062, which may be deployed within the patient to anchor into tissue of the patient's back, such as muscle, bone, ligament or the like. In one embodiment, for example, guidewire 1048 may have one or more lumens (not shown), and anchoring members 1062 may be translated through the lumen(s) to extend out of distal end 1047. When a tissue modification procedure is complete, anchoring members 1062 may be retracted within the lumen(s) so that guidewire 1048 may be more easily removed from the patient.

Referring to FIG. 13E, in another embodiment tissue removal device 1040 may also include one or more proximal shaft anchoring members 1066 and/or one or more proximal guidewire anchoring members 1064. Shaft anchoring member 1066 may, in alternative embodiments, either be coupled with or removably couplable with shaft 1041 to facilitate application of anchoring force. For example, in one embodiment, shaft anchoring member 1066 may abut the patient's back to resist translation of shaft 1041 into the patient.

Proximal guidewire anchoring member 1064 may be included in handle 1046, as shown, or in other embodiments may be located proximal or distal to handle 1046. Guidewire anchoring member 1064 may be used to lock or anchor guidewire 1048 to prevent or minimize its translation into or out of device 1040. This may help facilitate application of tensioning and/or anchoring force via guidewire 1048.

Figure 13F:
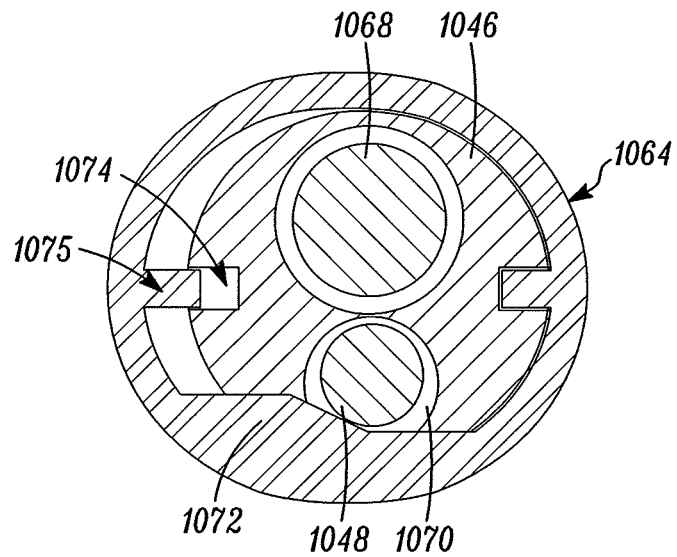
FIGS. 13F and 13G are cross-sectional views of a portion of the tissue modification device of FIG. 13E, through line C-C on FIG. 13E, in various configurations according to one embodiment of the present invention.
Figure 13G:
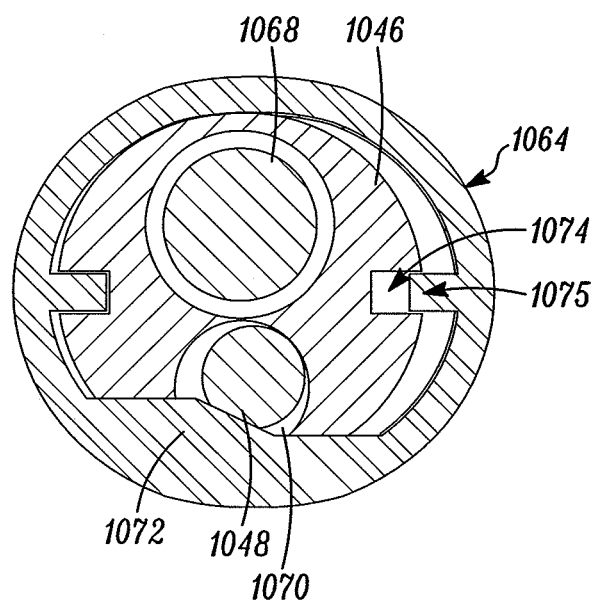

FIGS. 13F and 13G show cross-sectional views of handle 1046 and proximal guidewire anchoring member 1064 taken through line C-C on FIG. 13D. In one embodiment, handle 1046 may include proximal guidewire anchoring member 1064, a tissue modifying drive 1068 in a first lumen, a guidewire 1048 in a guidewire lumen 1070, multiple guiding slots 1074 with corresponding guiding tabs 1075, and one or more lobes 1072. As shown in FIG. 13F, when guidewire anchoring member 1064 is disengaged, guidewire 1048 may freely translate within guidewire lumen 1070, because lobe 1072 does not interfere. As shown in FIG. 13G, when guidewire anchoring member 1064 is engaged, for example by translating and/or rotating guidewire anchoring member 1064 with respect to handle 1046, guidewire 1048 may friction fit (e.g., clamp, pinch) between lobe 1072 of guidewire anchoring member 1064 and the wall of guide wire lumen 1070. Guidewire anchoring member 1064 may then be translated and/or rotated back to the original position (FIG. 13F) to disengage guidewire 1048.

Figure 14:
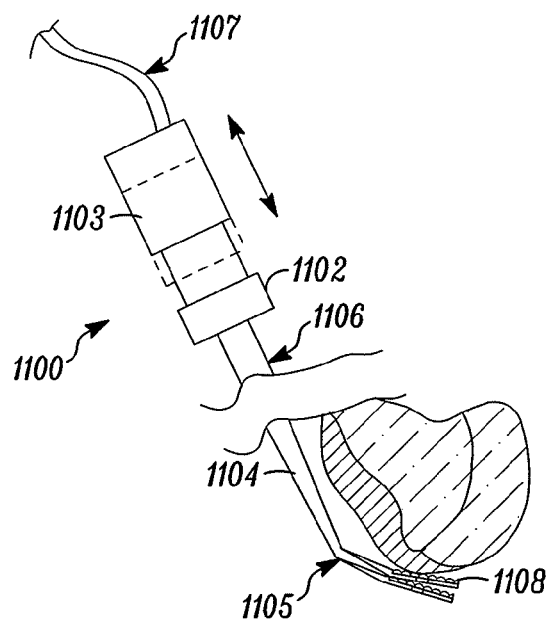
FIG. 14 is a cross-sectional view of a portion of a spine with a tissue modification device having a steerable distal portion in position for modifying tissue according to one embodiment of the present invention.

Referring now to FIG. 14, in some embodiments a tissue removal device 1100 may include an elongate shaft 1104 having proximal 1106 and distal 1105 portions, one or more tissue modifying members 1108, a movable handle 1103 coupled with proximal portion 1106, and a power connector 1107. In the embodiment shown, distal portion 1105 is at least partially steerable (shown in FIG. 14 as two, overlapping distal portions), and movable handle 1103 may be used (two-headed, straight arrow) to steer distal portion 1105 while holding shaft 1104 relatively stationary. A steerable distal portion 1105 may enhance the ability of tissue modifying members 1108 to contact and apply force against target tissue. In some embodiments, the location of tissue modifying members 1108 may be adjusted, using steerable distal portion 1105, without significantly moving shaft 1104. In some embodiments, steerable distal portion 1105 may move in multiple directions, such as laterally and up-and-down, relative to the longitudinal axis of shaft 1104. Movable handle 1103 may operate with a piston-like motion, in one embodiment, where a distal portion of handle 1102 is attached to the shaft and a proximal portion handle 1103 is attached to a tensioning member. The tensioning member may translate tension to steerable distal end 1105 when handle 1103 is actuated, which in turn deflects distal end 1105. In various alternative embodiments, any other handle steering mechanisms and/or other steering mechanisms, many of which are known in the art, may be used.

Figure 15A:
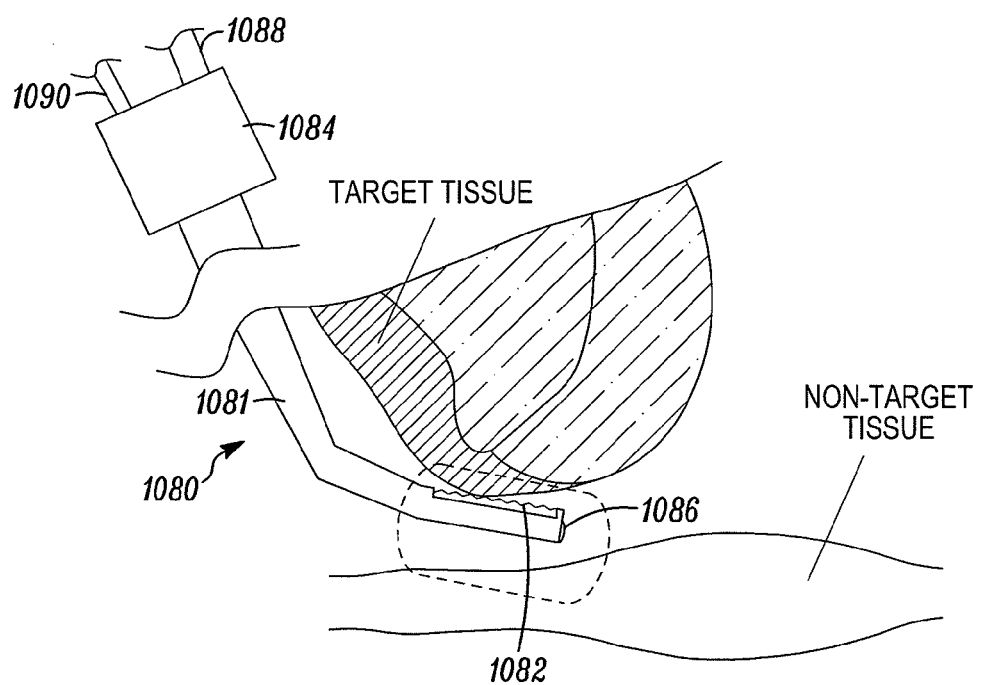
FIG. 15A is a cross-sectional view of a portion of a spine with a tissue modification device in position for modifying tissue according to one embodiment of the present invention.
Figure 15B:
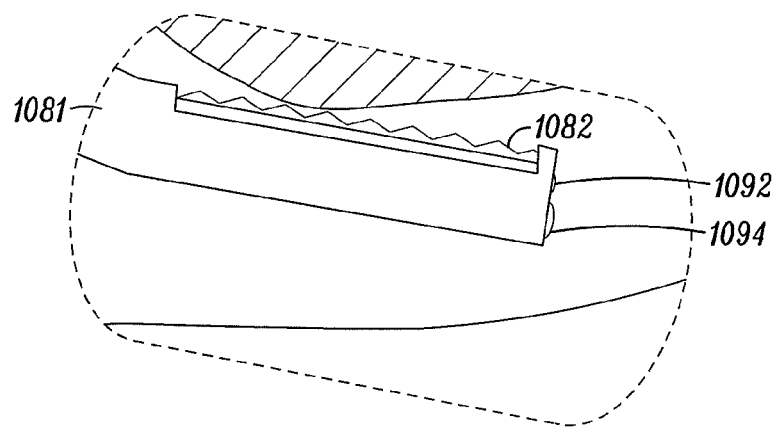
FIG. 15B is a close-up of portion D-D of FIG. 15A.

FIGS. 15A and 15B show one embodiment of a tissue modification device 1080, which includes an elongate shaft 1081, one or more tissue modifying members 1082, a handle 1084, a visualization device 1086, an optical cable 1090 and a power connector 1088. Visualization device 1086 may include any suitable device, such as but not limited to an endoscope. An endoscope visualization device may have lenses and/or fiber optics, for example, for delivering light (or other energy) to illuminate the tissue and capturing images. As shown in FIG. 15B, in some embodiments, visualization device 1086 may include one or more image capturing elements 1094 and one or more illuminating elements 1092. Image capturing element 1094 may include, for example, a CCD or CMOS chip, in some embodiments. Illuminating element 1092 may include, for example, one or more light emitting diodes (LEDs) or fiber optics, in some embodiments.

In some embodiments, optical cable 1090 may include fiber optics. Some or all of the fiber optics may comprise or may be coupled with illuminating elements 1092. Alternatively or additionally, some or all of the fiber optics may be connected to a camera (not shown). For example, such a camera may be attached to the proximal end of tissue modification device 1080. Optical cable 1090 may alternatively include one or more electrical wires connected to a power source (e.g., to power LED(s)) and/or an image capturing element 1094. Lenses, fiber optics, LED(s), or combinations thereof may be used for illumination with lenses, fiber optics, CCD, CMOS, or combinations thereof used for image capturing, according to various embodiments.

Figure 16:
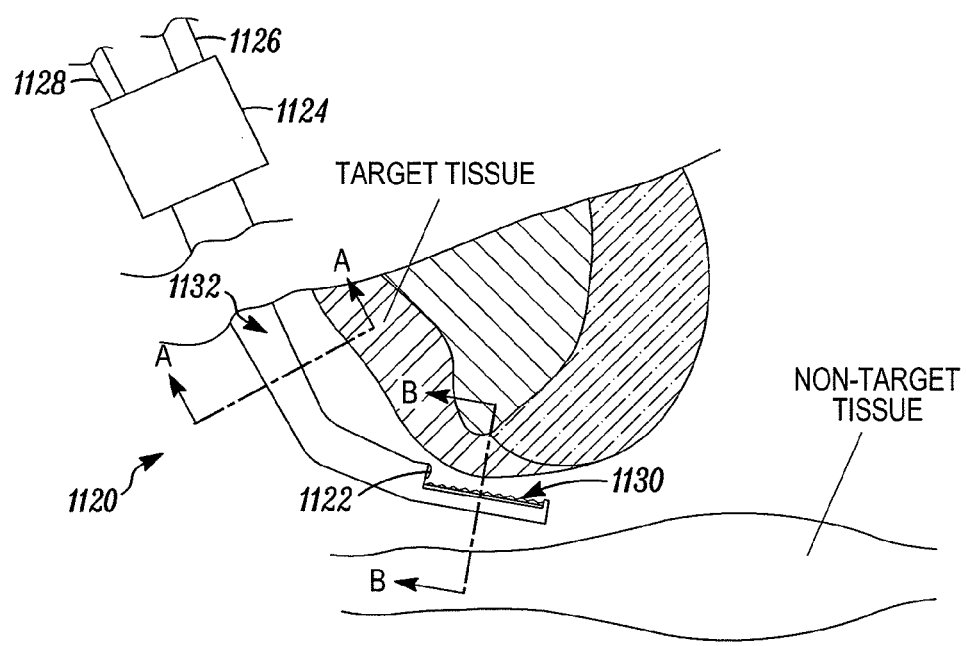
FIG. 16 is a cross-sectional view of a portion of a spine with a tissue modification device in position for modifying tissue according to one embodiment of the present invention.

Referring now to FIG. 16, another embodiment of a tissue modification device 1120 may suitably include an elongate shaft 1132, one or more tissue modifying members 1130, a handle 1124, a visualization device 1122, an optical cable 1128 and a power connector 1126. In this embodiment, visualization device 1122 is located proximal to tissue modifying member(s) 1130 on shaft 1132. In various embodiments, visualization device(s) 1112 may be positioned along shaft 1132 at any desired location.

FIGS. 17A-17E show cross-sectional views of various embodiments of shaft 1132, from the perspective of line A-A in FIG. 16. In the embodiment shown in FIG. 17A, for example, shaft 1132 may include a tissue modifying drive 1134 within a tissue modifying drive lumen 1140, and a guidewire 1136 within a guidewire lumen 1138. Tissue modifying drive 1134 may be configured to translate or rotate with respect to tissue modifying drive lumen 1140. Examples of tissue modifying drives 1134 include, but are not limited to, a drive shaft, one or more conductive wires, one or more optical fibers, or the like. Various embodiments may also include a motor, which may be located in the handle of the device, near the device distal end, in a separate drive apparatus, or the like.

Figure 17A:
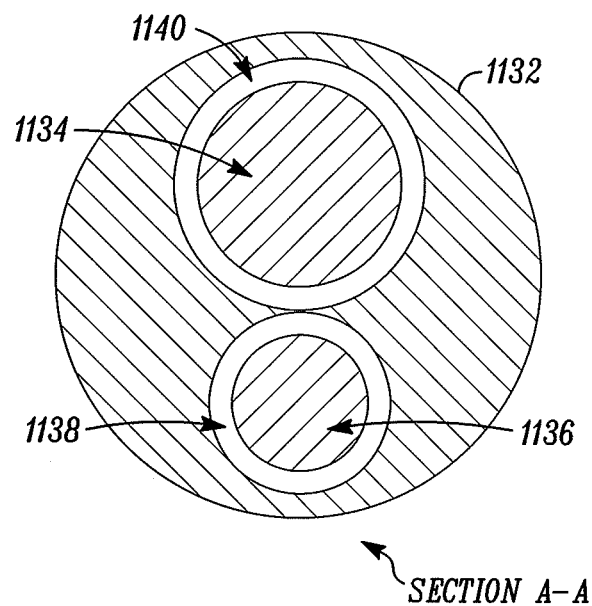
FIGS. 17A-17E are cross-sectional views taken through line A-A of FIG. 16 according to various alternative embodiments of the present invention.
Figure 17B:
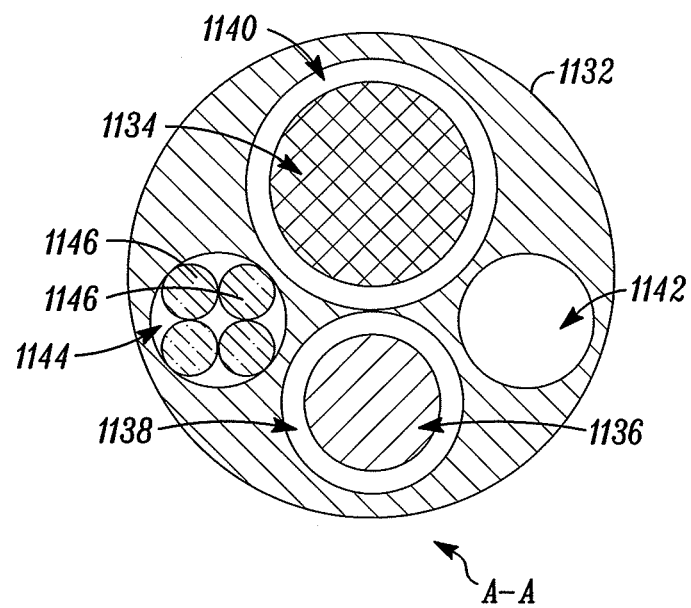

In an alternative embodiment, as shown in FIG. 17B, shaft 1132 may include tissue modifying drive 1134 within tissue modifying drive lumen 1140, guidewire 1136 within guidewire lumen 1138, conductive elements 1146 within a visualization lumen 1144, and suction/irrigation lumen 1142. Suction/irrigation lumen 1142 may be used, for example, to deliver gas, fluid or pushable solids (e.g., granular solids) from outside the patient to the distal end of the device or to aspirate gas, fluids, tissue and/or other material from the targeted tissue region to the outside of the patient. Suction/irrigation lumen 1142 may also be used, in some embodiments, to slidably pass instruments, such as a long flexible needle or biopsy forceps. Visualization lumen 1144, in some embodiments, may be configured to receive conductive elements 1146, such as elements to power LEDs at the distal end of the device, and/or to carry the signal from a CCD or CMOS chip located at the distal end of the device that has captured a visual image and converted it into an electronic signal to a display device located outside the patient.

Figure 17C:
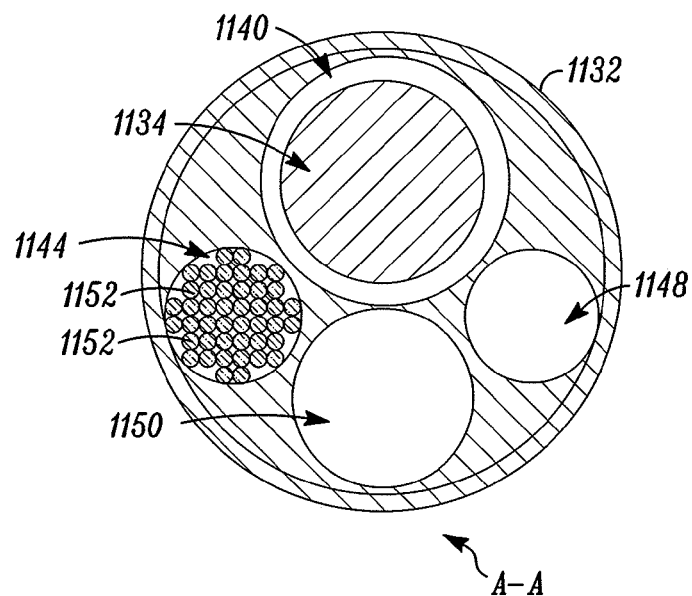

In yet another alternative embodiment, shown in FIG. 17C, shaft 1132 may include tissue modifying drive 1134 within tissue modifying drive lumen 1140, conductive elements and/or fiber optics 1152 within visualization lumen 1144, and separate suction 1150 and irrigation 1148 lumens. Suction lumen 1150 and irrigation lumen 1148 may be used, in some embodiments, to simultaneously or sequentially deliver and remove gases, fluids and/or pushable solids to and from the distal end of a tissue modification device. Delivery and removal of gases, fluids and/or pushable solids may help clear detached and/or non-detached target tissue and other debris from the treatment site and/or maintain a clear visualization of the target and non-target tissue via the visualization element.

Figure 17D:
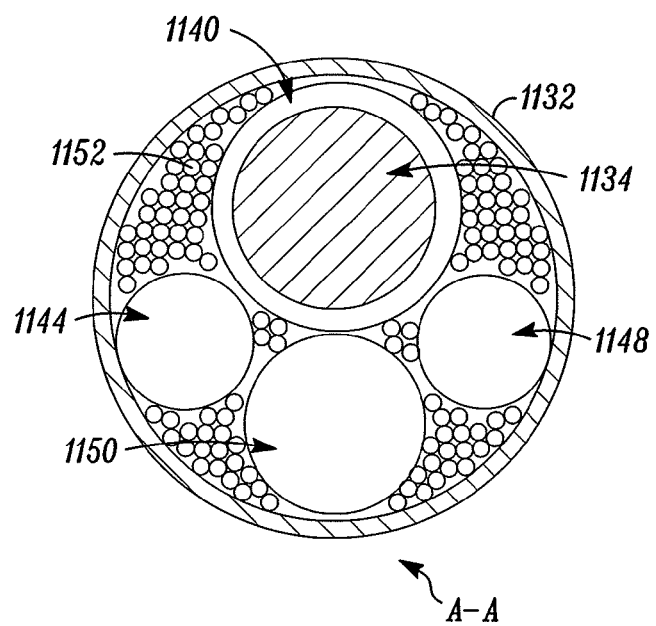

In another embodiment, illustrated in FIG. 17D, fiber optics 1152 may be disposed within a hollow shaft 1132, in between various lumens 1148, 1150, 1144, 1140. Alternatively, fiber optics 1152 may be replaced with electrical conductors in other embodiments. Fiber optics 1152 may deliver light to illuminate the target tissue and/or deliver light from the tissue to a viewing device. Visualization lumen 1144, in such an embodiment, may transport light or electrical signals in proximal and/or distal directions.

Figure 17E:
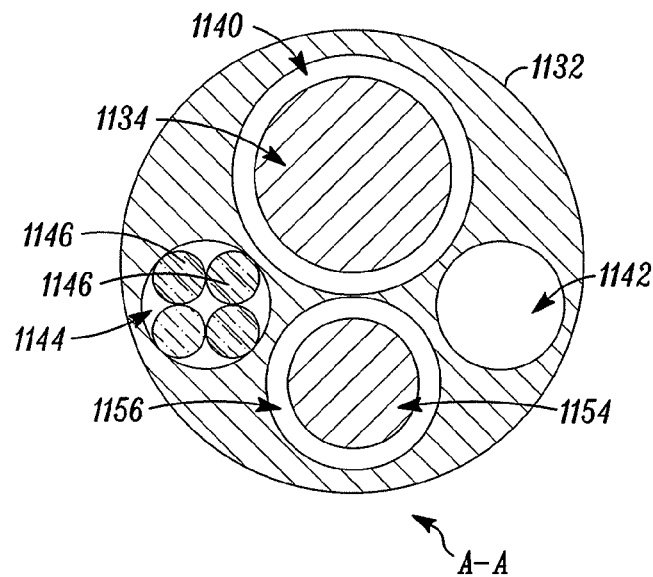

In yet another alternative embodiment, as in FIG. 17E, shaft 1132 may include a steering actuator 1154 within a steering lumen 1156. Steering actuator 1154 may be used, for example, to help steer a distal portion of a tissue modification device, as described in further detail above.

Figure 18:
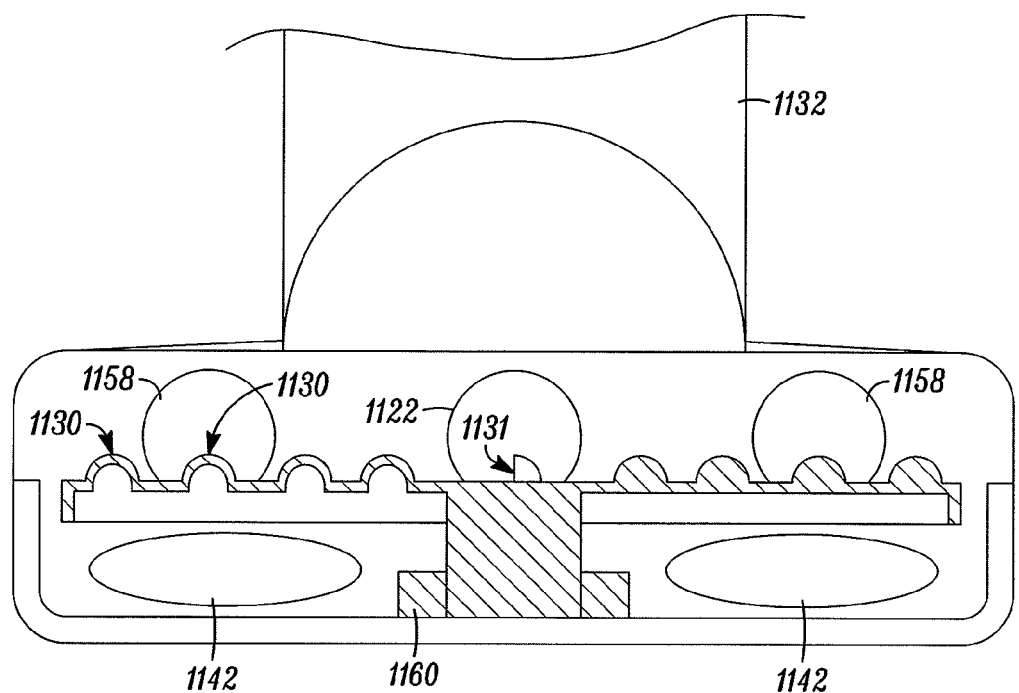
FIG. 18 is a cross-sectional view taken through line B-B of FIG. 16 according to one embodiment of the present invention.

FIG. 18 is an end-on cross-sectional view of tissue modification device 1120 of FIG. 16, shown from the perspective of line B-B. In this embodiment, visualization device 1122 and illuminating elements 1158 are located proximal to tissue modifying member 1130. In the embodiment shown, tissue modifying member 1130 includes a rotating disc mounted on a post in a bearing 1160, with multiple raised cutting edges 1131 on the disc. Two suction/irrigation lumens 1142 allow for introduction and suction of gas, fluid and/or pushable solids from an area of tissue modification.

Figure 19:
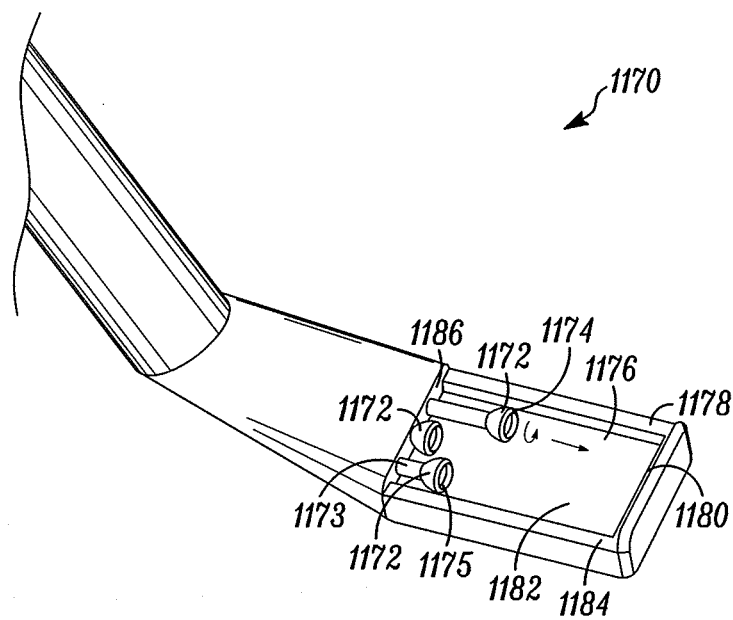
FIGS. 19-33 are perspective or side views of a distal portion of a tissue modification device according to various alternative embodiments of the present invention.

FIGS. 19-40F illustrate a number of embodiments of a distal end of a tissue modification device having various different tissue modifying members. Referring to FIG. 19, in one embodiment, a tissue modification device 1170 may include multiple tissue modifying members 1172, each including a cup 1174 attached to a drive shaft 1173 and having a cutting edge 1175. Tissue modifying members are located within an open chamber 1176 formed by multiple walls 1178, 1180, 1182, 1184, 1186. Cups 1174 may be rotated and/or translated to cut target tissue disposed in open chamber 1176, as shown by the curved and straight arrows.

Figure 19A:
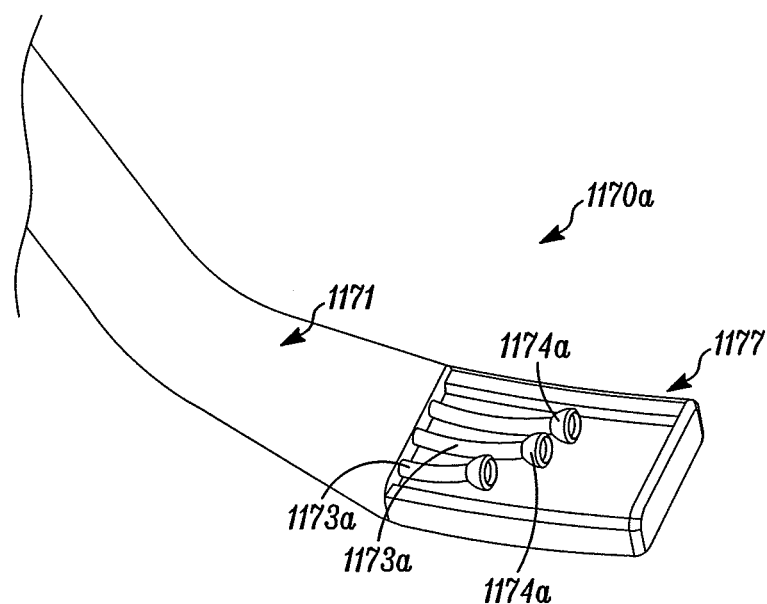

FIG. 19A illustrates an alternative embodiment in which a tissue modification device 1170a may include a shaft 1171, which is curved and/or flexible along at least part of its length, and a tissue modifying portion 1177, which is also curved and/or flexible. Tissue modifying portion 1177 may include curved and/or flexible shafts 1173a, and cups 1174a, similar to those shown in FIG. 19. As mentioned previously, many of the embodiments described herein may have either flat/straight tissue modifying members/surfaces or curved and/or flexible tissue modifying members/surfaces, according to various embodiments. Therefore, although many of the following embodiments of tissue modifying members are shown and described as having generally flat configurations, in alternative embodiments, many if not all such tissue modifying members may have curved and/or flexible configurations instead.

Figure 20:
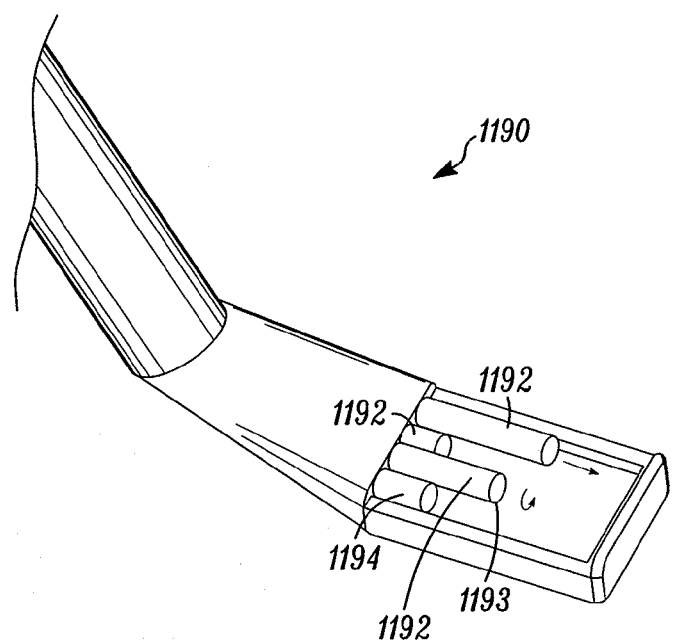

In an alternative embodiment, shown in FIG. 20, a tissue modification device 1190 may include multiple tissue modification members 1192, each comprising a hollow tube 1194 with a cutting edge 1193. In one embodiment, tubes 1194 may be rotated and translated to cut tissue. Tubes 1194 may also be used for suction and/or irrigation in some embodiments.

Figure 21:
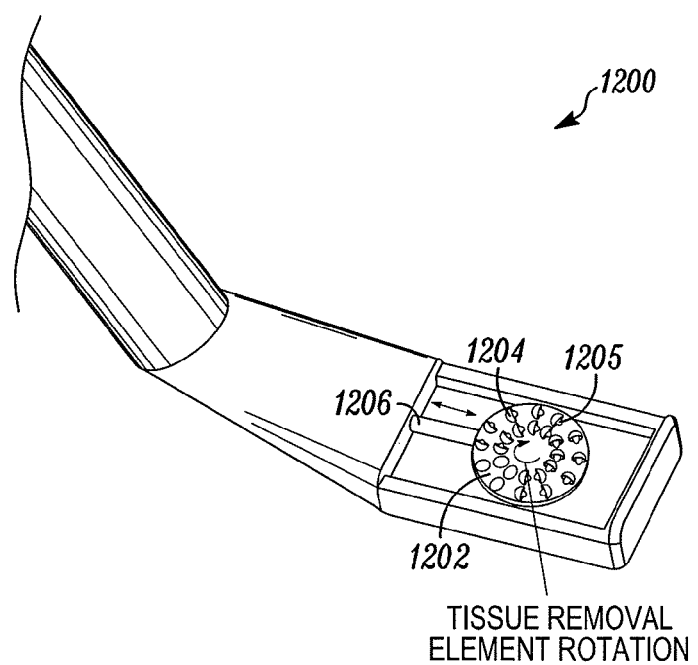

FIG. 21 shows another alternative embodiment, in which a tissue modification device 1200 includes a tissue modifying member 1202 comprising a disc and multiple raised cups 1204, each cup having a cutting edge 1205, and the disc being mounted on a drive shaft 1206. In one embodiment, tissue modifying member may oscillate by moving shaft 1206 back and forth and/or may rotate by rotating the disc around an axis.

Figure 22:
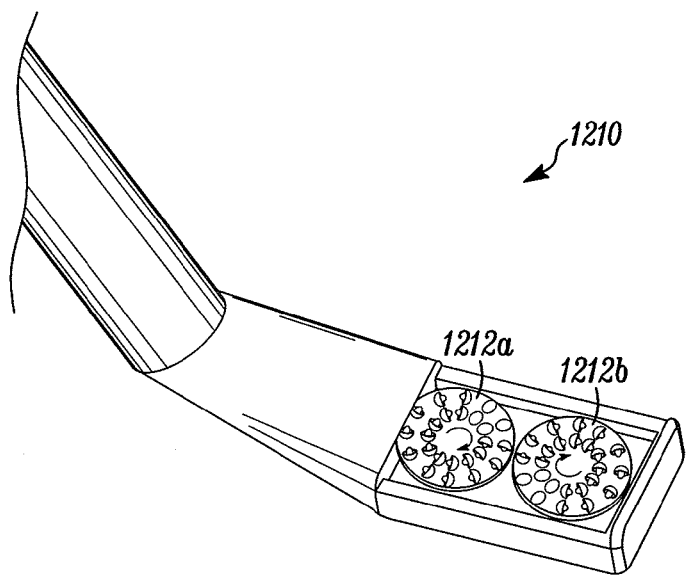

In another embodiment, as in FIG. 22, a tissue modification device 1210 may include two rotating tissue modification members 1212a, 1212b, each comprising a disc with raised cutting edges. The discs may rotate in the same directions or opposite directions in various embodiments. Rotating members 1212a, 1212b in opposite directions may help balance forces between the two members 1212a, 1212b and target tissue, thereby helping stabilize tissue modification device 1210 and enhance tissue modification procedures.

Figure 23:
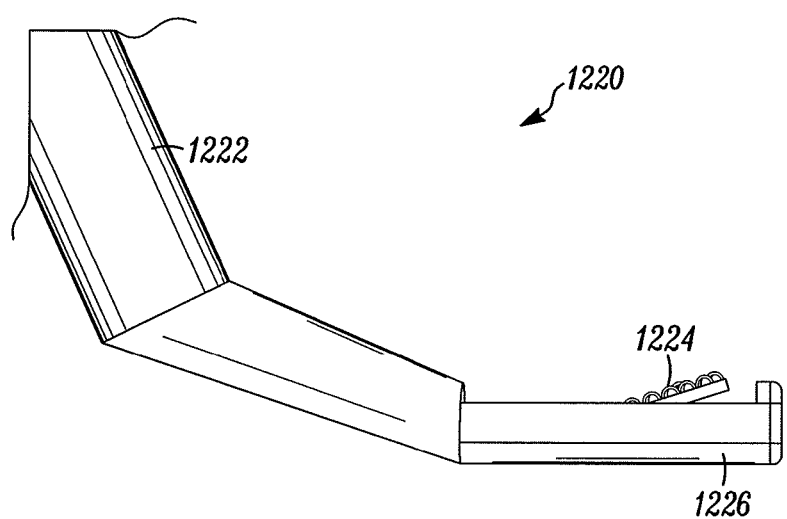

FIG. 23 illustrates that, in some embodiments, a tissue modifying member 1224 of a tissue modification device 1220 may be angled relative to a longitudinal axis of a distal portion 1126 of a shaft 1222. Angling tissue modifying member 1224 away from the long axis of distal portion 1126 may allow tissue modifying member 1224 to extend out of a an open chamber or window, for example, to facilitate tissue modification. The angle of tissue modification member 1224 may be fixed or adjustable in various embodiments. Angling tissue modifying member 1224 may also enhance contact of tissue modifying member 1224 with target tissue, thus enhancing tissue modification.

Figure 24:
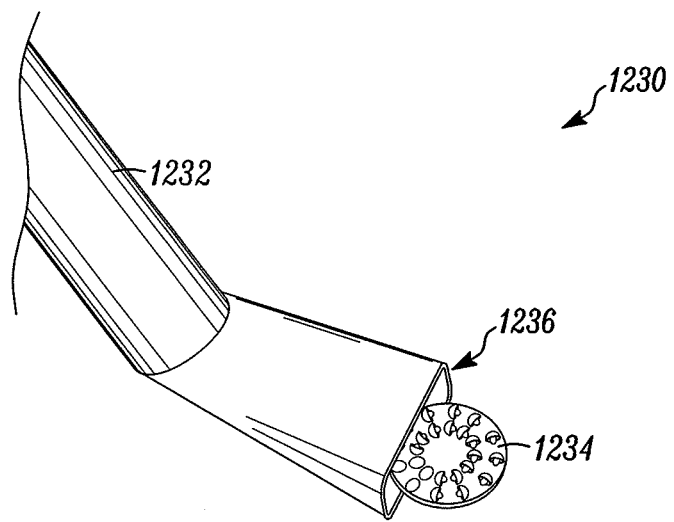

In another alternative embodiment, as in FIG. 24, a tissue modification device 1230 may include a tissue modification member 1234 that extends out of a distal opening 1236 at the distal end of a shaft 1232. In some embodiments, tissue modification member 1234 may be moved back and forth to be housed within or to extend out of distal opening 1236. In other embodiments, tissue modification member 1234 may be fixed in relation to opening 1236.

Figure 25:
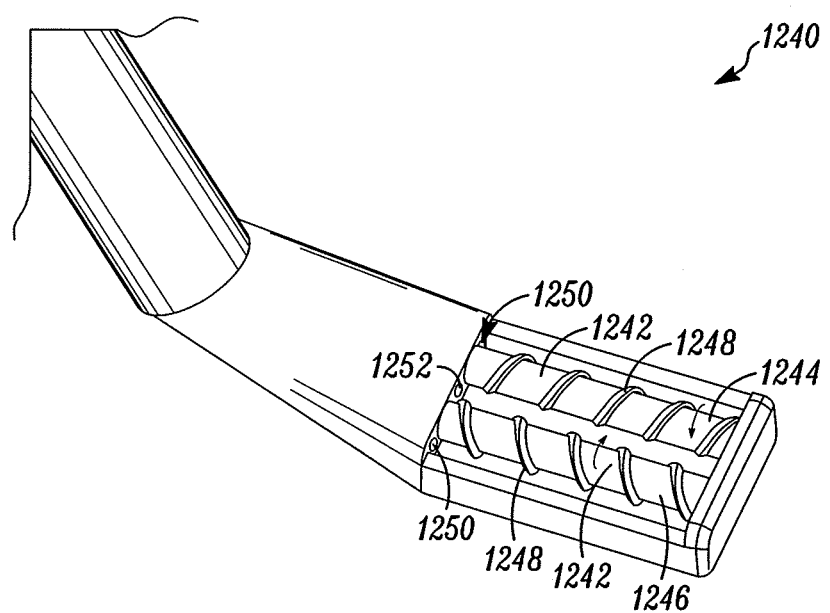

FIG. 25 shows another embodiment of a tissue modification device 1240, which includes tissue modifying members 1242, each including a rotating shaft 1244, 1246 and a helical cutting blade 1248. Device 1240 also may include one or more irrigation ports 1250 and one or more suction ports 1252. In various embodiments, cutting blades 1248 may be configured to remove both hard and/or soft tissue. Cutting blades 1248 may also be configured to transport separated tissue proximally toward and/or into the shaft of device 1240, and/or suction port 1252, so that such tissue may be removed from the patient. Rotating shafts 1244 may be configured to rotate in opposite directions, in some embodiments, thus helping balance forces exerted by tissue modifying members 1242 on target tissues.

Figure 26:
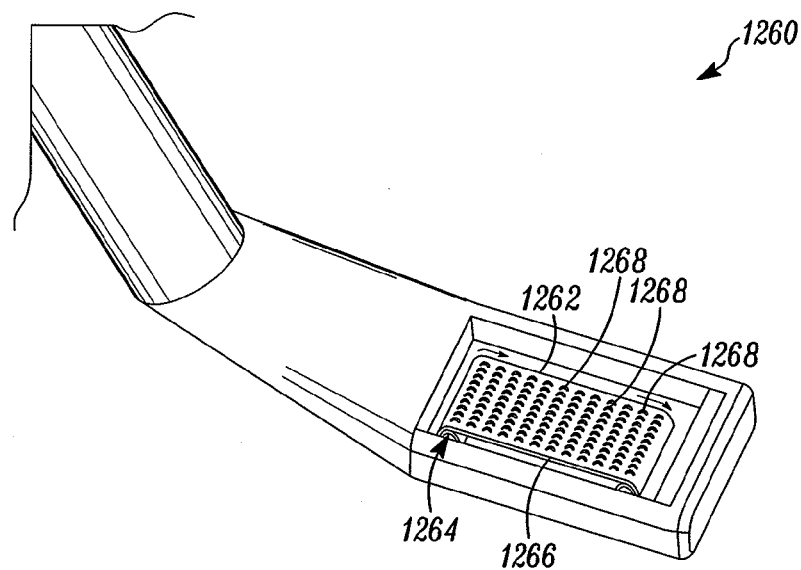

In yet another embodiment, shown in FIG. 26, a tissue modification device 1260 may include a tissue modifying member 1262 comprising a belt 1266, mounted on rotating rollers 1264 and carrying multiple raised abrasive members 1268. Rollers 1264 may be activated to rotate, thus causing belt 1266 to move, and thus causing abrasive members 1268 to abrade target tissue.

Figure 27:
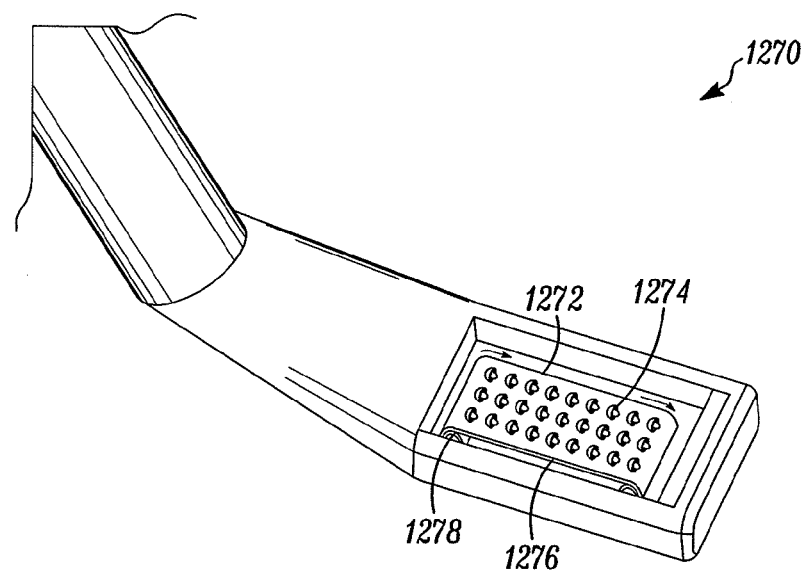

In a similar alternative embodiment, shown in FIG. 27, a tissue removal device 1270 may include a tissue modifying member 1272 comprising a belt 1276, mounted on rotating rollers 1278 and carrying multiple raised cutting members 1274. Rollers 1278 may be activated to rotate, thus causing belt 1276 to move, and thus causing cutting members 1274 to cut target tissue.

Figure 28:
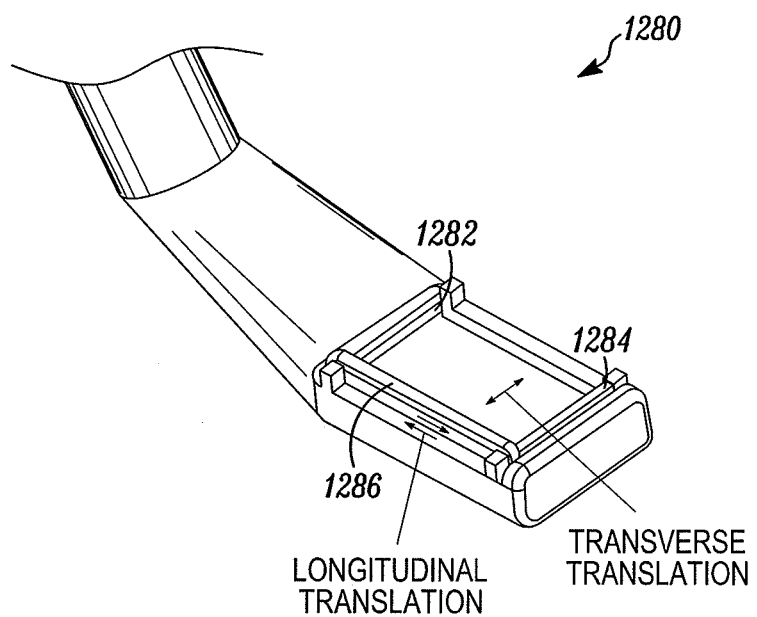

Referring to FIG. 28, in another alternative embodiment, a tissue removal device 1280 may include a tissue modifying member 1286 comprising one or more wires that move along multiple transverse guide rails 1282, 1284. In one embodiment, tissue modifying member 1286 may move laterally along guide rails 1282, 1284 and may also translate over guide rails 1282, 1284. In various embodiments, the tissue modifying member(s) 1286 (i.e., the wire(s)) may translate, rotate, reciprocate and/or oscillate. In some embodiments, the wire(s) may be coated (e.g., on the outer surface) with an abrasive material, and/or have a high friction outer texture. In some embodiments, the wires may be coupled to an energy (e.g., RF current, thermal) generator. In alternative embodiments, wires may be solely at or within the shaft distal portion or may extend from the shaft distal end to a more proximal location along shaft.

Figure 29:
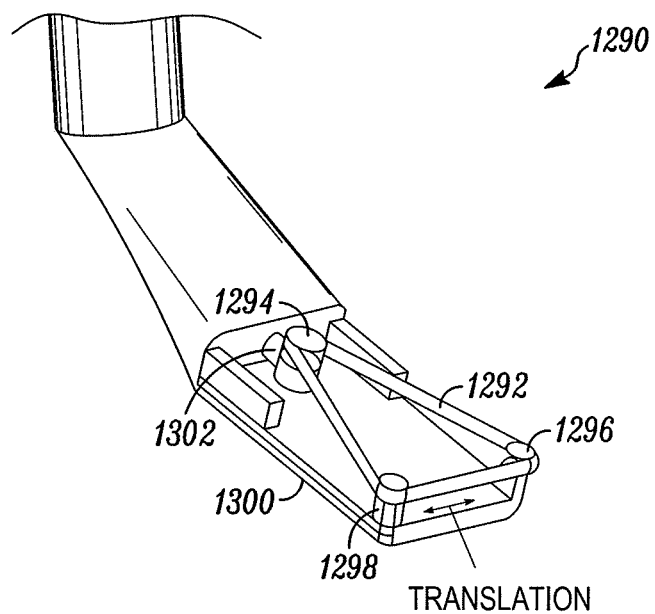

FIG. 29 illustrates another embodiment of a tissue modification device 1290, in which a tissue modifying member 1292 is coupled with rotating drive post 1294 and two free posts 1296, 1298. Drive post 1294 is coupled with a drive shaft 1302, which turns drive post 1294, thus translating tissue modifying member 1292 to modify tissue. Tissue modifying member 1292 may be elevated above a floor 1300 of the device shaft, so as to more easily contact target tissue. In various embodiments, tissue modifying member 1292 comprises a cutting wire or abrasive wire and may be translated either in one direction or in both directions. In some embodiments, drive shaft 1302 may be advanced and retracted to further move and/or change the configuration of tissue modifying member 1292.

Figure 30A:
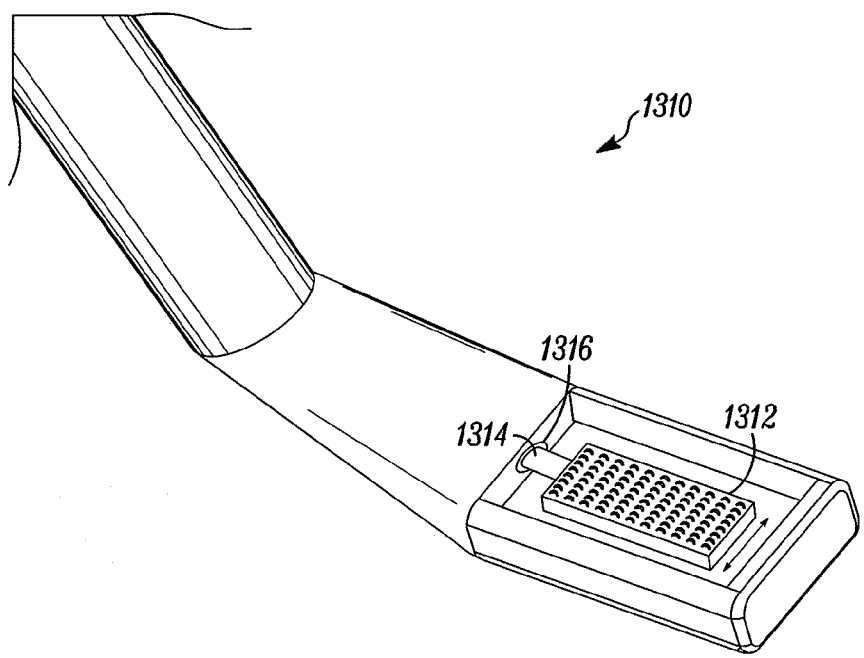
Figure 30B:
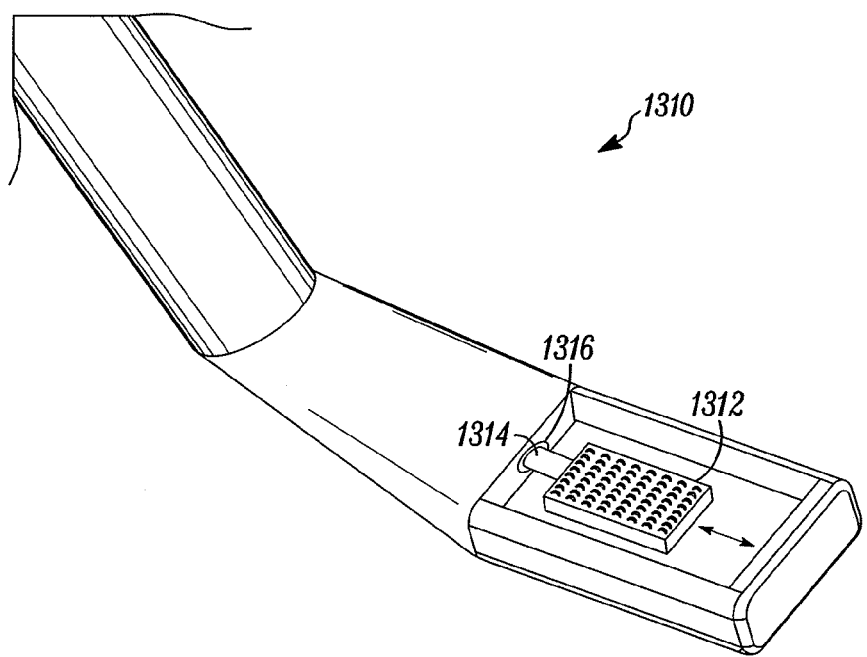
Figure 30C:
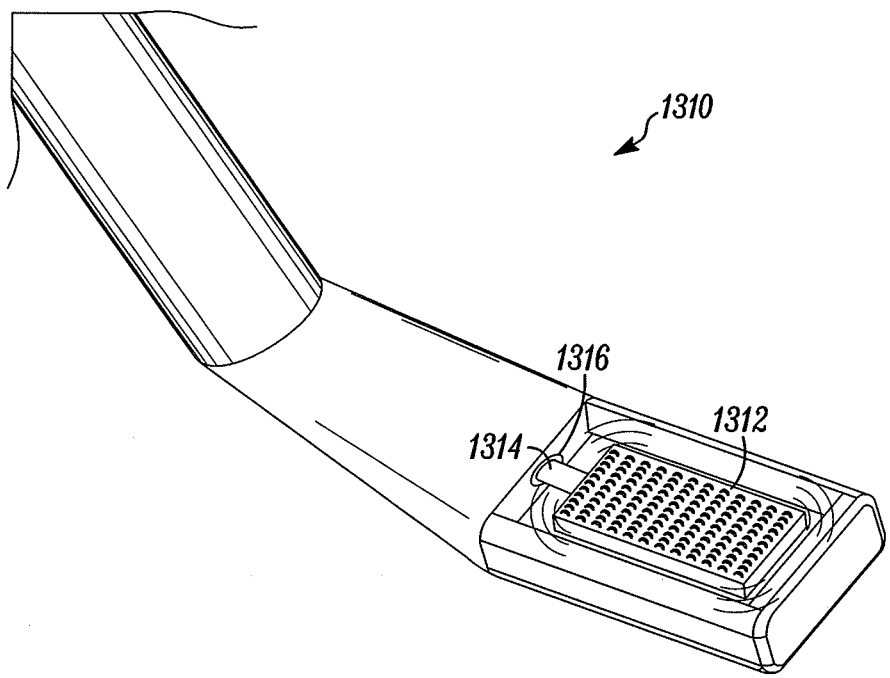
Figure 31:
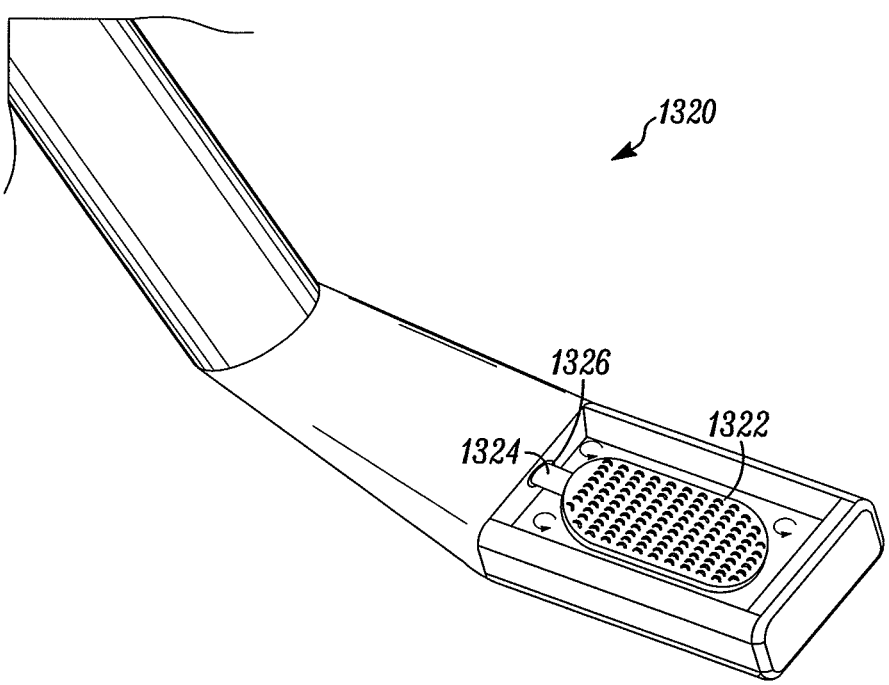

Referring now to FIGS. 30A-30C, in another embodiment, a tissue modification device 1310 may include a tissue modifying member 1312 comprising a movable platform with an abrasive surface and coupled with a drive shaft 1314 extending out of a distal opening 1316. As shown in the various figures, in some embodiments tissue modifying member 1312 may move laterally (FIG. 30A), may translate back and forth (FIG. 30B) and/or may vibrate (FIG. 30C).

In yet another embodiment, as in FIG. 3I, a tissue modification device 1320 may include a tissue modification member 1322 comprising an oval or round platform with an abrasive surface and coupled with a drive shaft 1324 extending out of a distal opening 1326. In such an embodiment, tissue modifying member 1322 may be made to rotate or move in a circular pattern, as well as translate, move laterally, oscillate and/or vibrate according to various embodiments.

Figure 32:
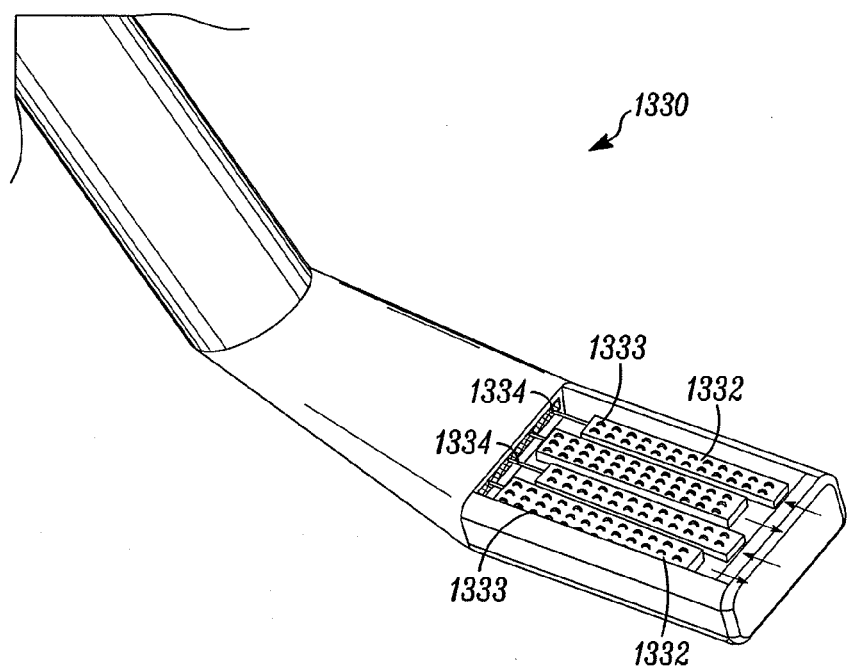

Referring to FIG. 32, in another embodiment a tissue modification device 1330 includes multiple tissue modifying members 1332, each including a movable platform 1333 with an abrasive surface attached to a drive shaft 1334. Tissue modifying members may move back and forth relative to one another and to the device shaft in any suitable pattern. Moving tissue modifying members 1332 back and forth relative to one another may help them apply tensioning forces to target tissue, thereby enhancing the ability of tissue modifying members 1332 to cut, shear, tear and/or otherwise modify target tissues.

Figure 33:
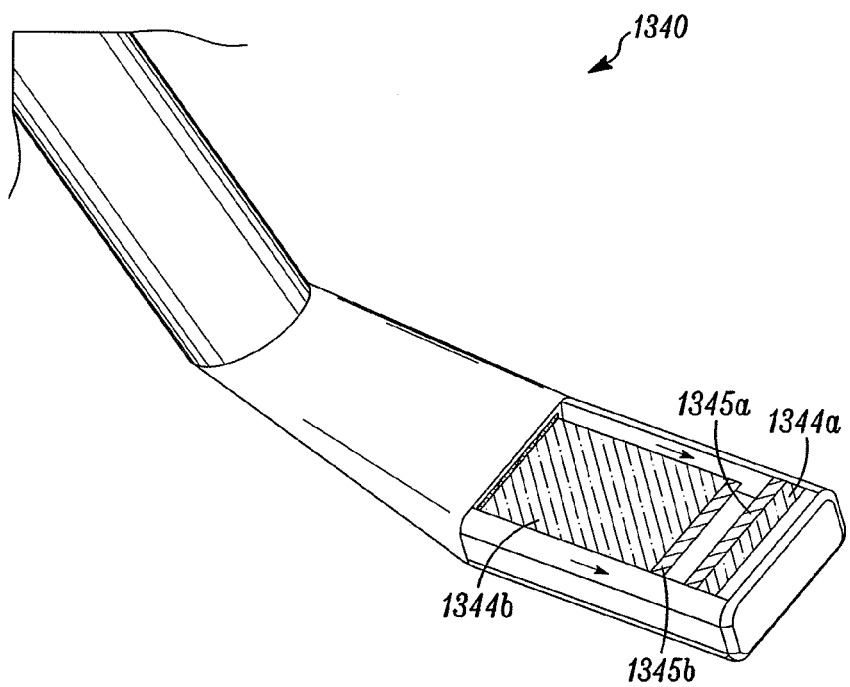

As shown in FIG. 33, in another alternative embodiment, a tissue modification device 1340 may suitably include tissue modifying members comprising one or more blades, such as a distal blade 1344*a* and a proximal blade 1344*b*, each having a cutting edge 1345*a*, 1345*b*. In the embodiment shown, proximal blade 1344*b* is movable and may translated distally toward the opposing distal blade 1344*a*. In alternative embodiments, distal blade 1344*a* may be movable or both blades 1344*a*, 1344*b* may be movable. Alternative embodiments may include one movable blade, more than two movable blades facing in one direction, more that two movable blades facing in different directions, a movable blade and a backstop against which the blade may be driven, or any other suitable combination of movable and/or immobile blades. Furthermore, any blade of any given embodiment may have any suitable shape, size and overall configuration. In some embodiments, blades may be flat, while in others they may be curved, squared off, ridged, bent, serrated or the like. Blades may be long or short, multiple blades may be aligned closely one after the other, such as in a typical multi-blade razor used for shaving a face, multiple blades may be disposed apart from one another by several millimeters or even centimeters, and/or the like. Blades may have any suitable amount of sharpness or dullness, and in some embodiment a combination of sharper and duller blades may be used. Therefore, although exemplary embodiments of blades are described in detail above and below, any other suitable blades or combinations of blades may be substituted in various embodiments, without departing from the scope of the present invention.

Blades 1344*a*, 1344*b*, or any other blades described in alternative embodiments herein, may be fabricated from metals, polymers, ceramics, any other suitable material or combination of materials. According to various embodiments, suitable metals for blades may include, but are not limited to, stainless steel (303, 304, 316, 316L), nickel-titanium alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Polymer materials include nylon, polyester, Dacron®, polyethylene, acetal, Delrin® (DuPont), polycarbonate, nylon, polyetheretherketone (PEEK), and polyetherketoneketone (PEKK). In some embodiments where polymers are used, such polymers may be glass-filled or carbon-filled to add strength and stiffness. Ceramics may include, but are not limited to, aluminas, zirconias, and carbides. Blades may be manufactured using skills known in the art, for example, metal injection molding (MIM), CNC machining, injection molding, grinding, EDM, sheet metal bending, etching, or the like. Other portions of a tissue modification device, such as a cover over one or more blades or other features, may be made of any suitable material now known or hereafter discovered. A blade cover, for example, may be fabricated in various embodiments of one or more polymeric materials, such as nylon, silicone, polyetheretherketone (PEEK), polyetherketoneketone (PEKK), polytetrafluoroethylene (PTFE), polyurethane (Tecothane,), Pebax (co, USA), polycarbonate, Delrin (co, USA), high-density polyethylene (HDPE), low-density polyethylene (LDPE), HMWPE, UHMWPE, or the like.

Figure 34A:
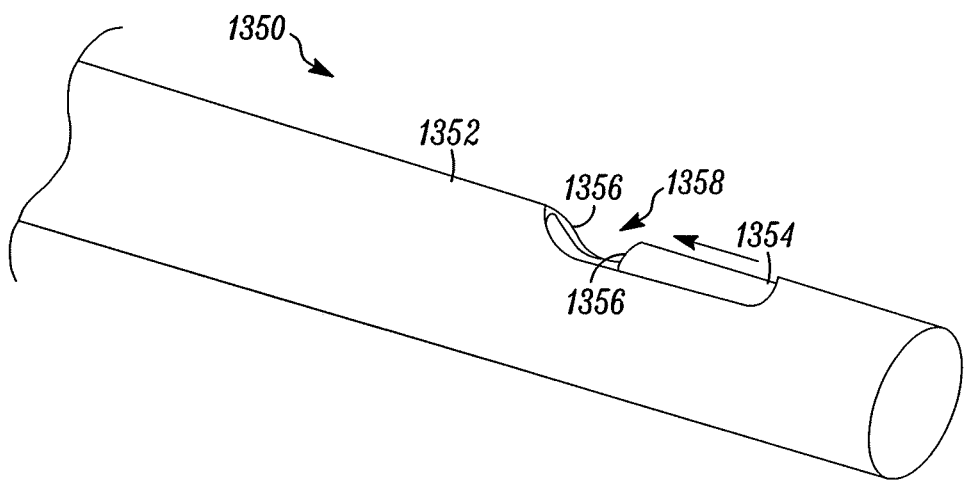
FIGS. 34A and 34B are perspective views of a distal portion of a tissue modification device according to alternative embodiments of the present invention.

Referring now to FIG. 34A, in one embodiment a tissue modification device 1350 may have a substantially cylindrical, circular, or otherwise curved shaft 1352 as well as one or more substantially cylindrical, circular, or otherwise curved blades 1354. In the embodiment shown, blade 1354 protrudes out of a window 1358 of shaft 1352. When blade 1354 is moved proximally (arrow), its cutting edge 1356 moves toward and perhaps engages with an opposing cutting edge 1356 of shaft 1352.

Figure 34B:
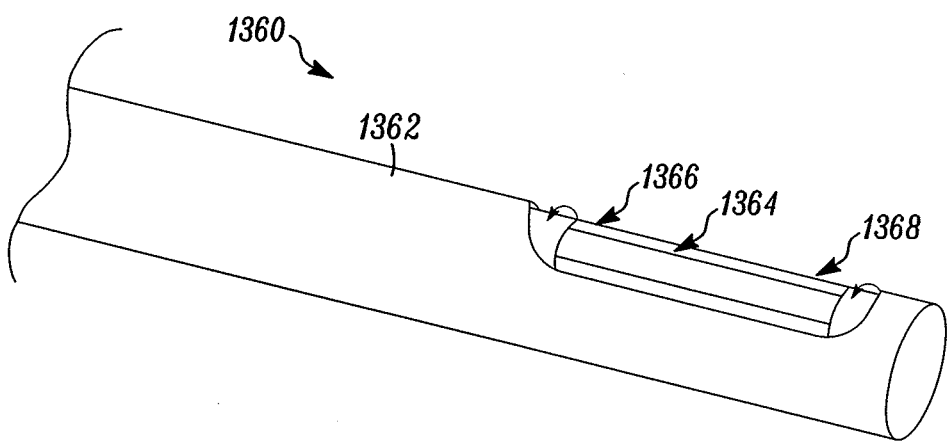

In an alternative embodiment, as in FIG. 34B, a tissue modification device 1360 may have a substantially cylindrical, circular, or otherwise curved shaft 1362 as well as one or more substantially cylindrical, circular, or otherwise curved blades 1364. In the embodiment shown, blade 1364 protrudes out of a window 1368 of shaft 1362. Blade 1364 may be rotated (arrows), to cause its cutting edges 1366 cut target tissue. In some embodiments, one or more curved blades 1364 may be translated as well as rotated. In either of the embodiments shown in FIGS. 34A and 34B, cut target tissue may optionally be removed through the inside of curved shaft 1352 or curved blade 1364.

Figure 35A:
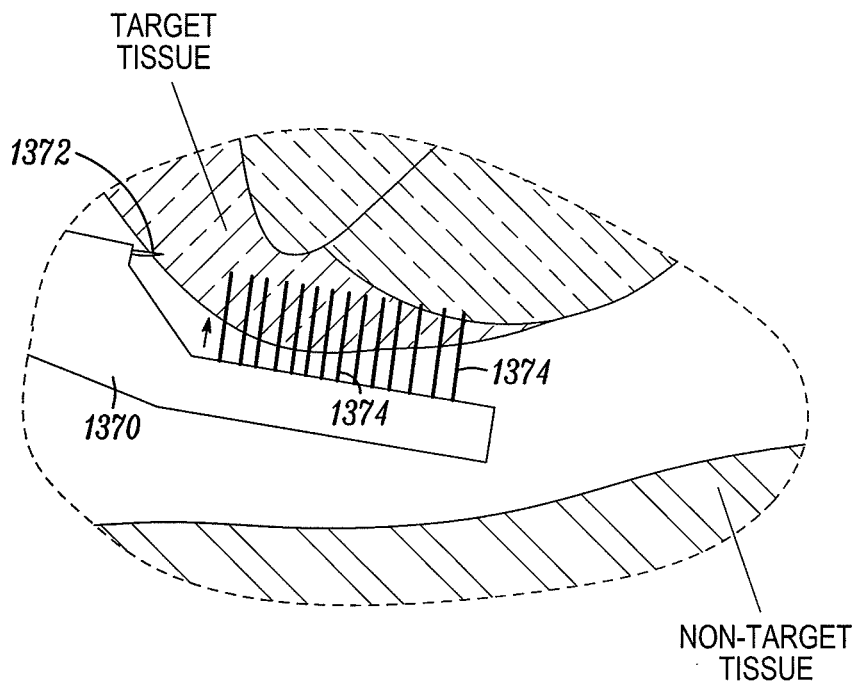
FIGS. 35A and 35B are side views of a distal portion of a tissue modification device according to one embodiment of the present invention.
Figure 35B:
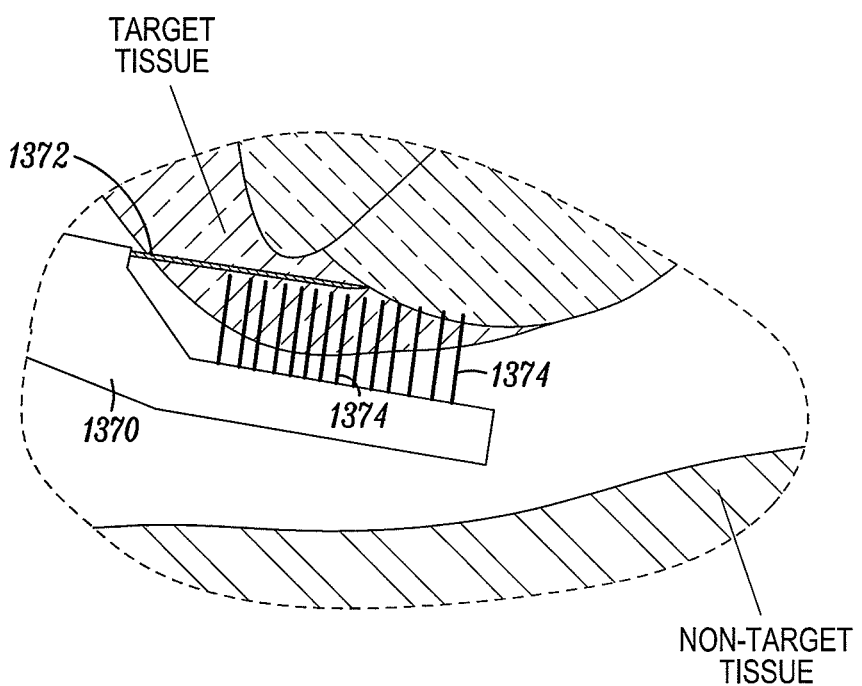

Referring now to FIGS. 35A and 35B, in some embodiments, a tissue modification device may include one or more anchoring members 1374 coupled with a distal shaft portion 1370 of the device. In various embodiments, any of a number of suitable anchoring members may be used. Some embodiments of anchoring members have been previously described above, and others will be described further below. In one embodiment, for example, anchoring members 1374 may comprise multiple needles, as shown in FIGS. 35A and 35B. Needles 1374 may act not only to anchor distal shaft portion 1370 to tissue, but may also change one or more characteristics of the tissue. For example, in some embodiments, inserting multiple needles into tissue may stiffen the tissue and thus enhance the ability of one or more tissue modifying members 1372 to cut or otherwise modify the tissue. In one embodiment, anchoring members/needles 1374 may be deployable out of distal shaft portion 1370 (arrow), such that needles 1374 are retracted during delivery of the device into the patient and then deployed into the target tissue when in a desired position. In various embodiments, anchoring members/needles 1374 may extend out of distal shaft portion 1370 in an orientation substantially perpendicular to the longitudinal axis of distal shaft portion 1370 or in any other suitable orientation relative to distal shaft portion 1370. or otherwise non-parallel to the longitudinal axis. During use, the tissue stiffening projections can extend into the target tissue. Needles 1374 will typically have a modulus of elasticity greater than the modulus of elasticity of the target tissue, and thus may stiffen (i.e., increase the effective modulus of elasticity) of the target tissue.

In the embodiment shown in FIGS. 35A and 35B, as well as in any alternative embodiments described herein, one or more members such as tissue anchoring members/needles 1374 may be used to modify tissue in any of a number of suitable ways. For example, in some embodiments, energy may be transmitted to one or more tissue anchoring members/needles 1374 to cool, heat or otherwise transmit energy to the tissue. Such cooling or heating, for example, may further change the stiffness or consistency of the tissue, thus facilitating tissue modification by one or more tissue modifying members. In one embodiment, for example, it may be advantageous to cool or even freeze tissue to increase its stiffness so that it can be more easily cut or abraded. For example, in some embodiments, a cryogenic fluid may be delivered via an irrigation lumen and/or suction/irrigation lumen to directly reduce the temperature of the anchoring members 1374 or to separately cool the target tissue. Any other suitable change may alternatively be made to tissue to enhance a tissue modification procedure according to various embodiments.

As shown in FIG. 35B, when anchoring members 1374 are in place within target tissue, tissue modifying member 1372 (a blade in the embodiment shown) may be translated out of distal shaft portion to cut or otherwise modify tissue. Tissue modifying member 1372 may advance out of distal shaft portion 1370 in a direction perpendicular or otherwise non-parallel to anchoring members 1374. In some embodiments, anchoring members/needles 1374 may retain target tissue after cutting, so that it may be removed from the patient.

Figure 36A:
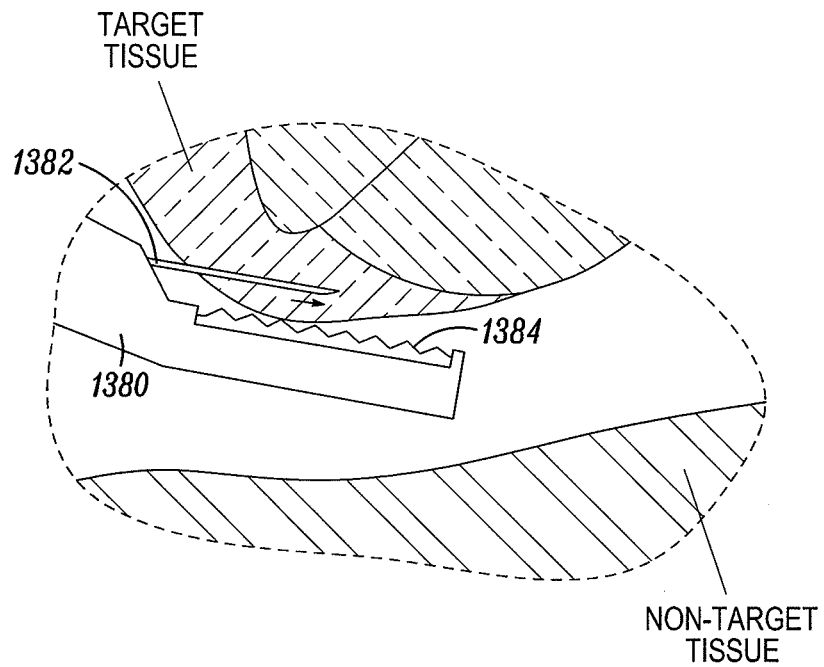
FIGS. 36A and 36B are side views of a distal portion of a tissue modification device according to an alternative embodiment of the present invention.
Figure 36B:
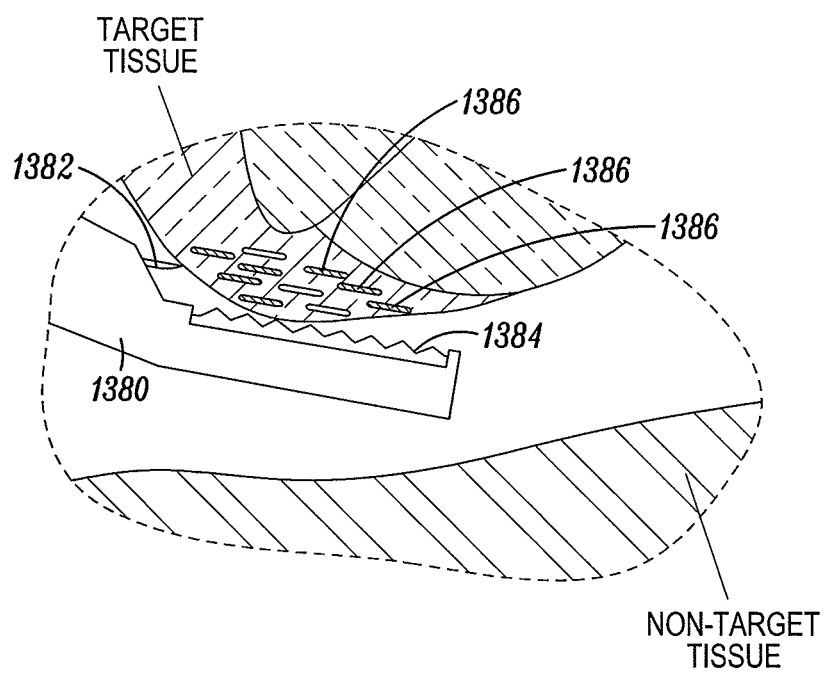

FIGS. 36A and 36B illustrate an alternative embodiment a tissue stiffening probe 1382 extends out of a distal shaft portion 1380 (FIG. 36A) and then breaks into multiple tissue stiffening inserts 1386 (FIG. 36B) to stiffen target tissue before it is modified by a tissue modifying member 1384. Alternatively, multiple tissue stiffening inserts 1386 may be delivered directly into the tissue. In some embodiments, inserts 1386 may be made from a bioresorbable material, so that if one or more inserts are left in the patient, they will harmlessly resorb in the patient's body.

Figure 37A:
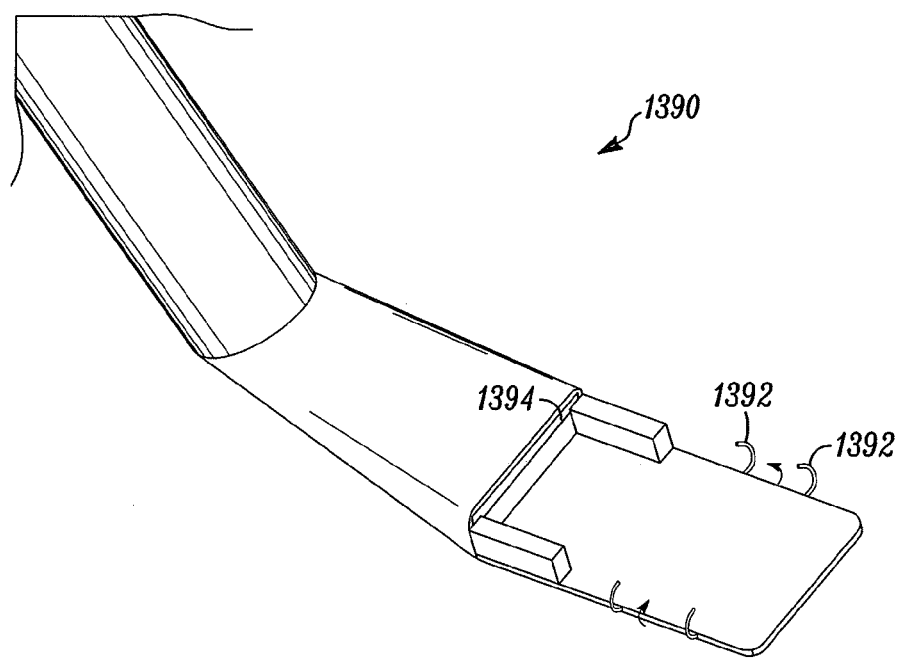
FIGS. 37A and 37B are perspective views of a distal portion of a tissue modification device according to an alternative embodiment of the present invention.
Figure 37B:
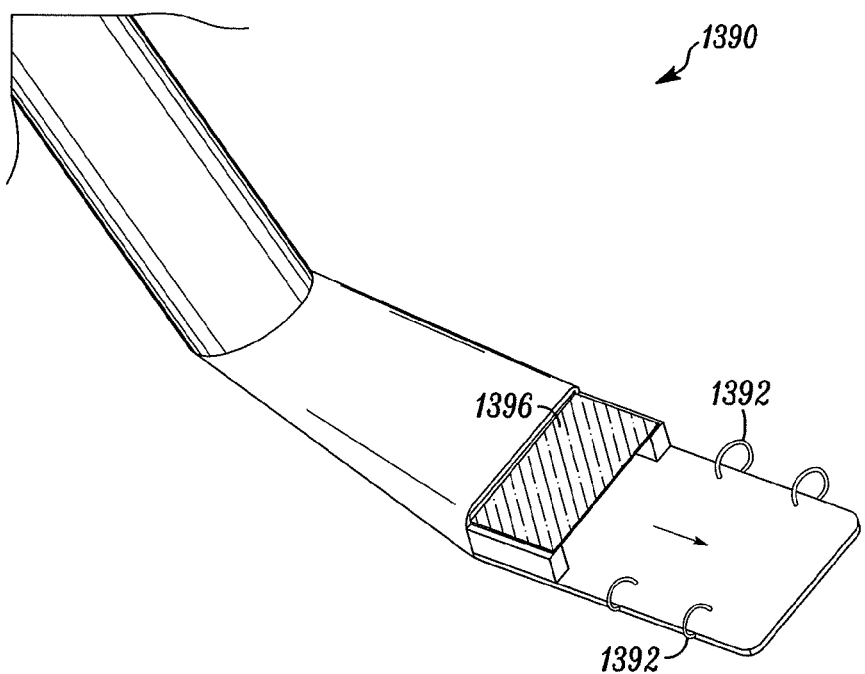

In yet another embodiment, shown in FIGS. 37A and 37B, a tissue modification device 1390 includes multiple deployable tissue anchoring members 1392 and a tissue modifying blade 1396 that translates through a blade lumen 1394. Tissue anchoring members 1392 may have a curved or circular configuration upon being deployed from tissue modification device 1390, and in some embodiments they may serve the dual function of anchoring to tissue and stiffening tissue.

Figure 38A:
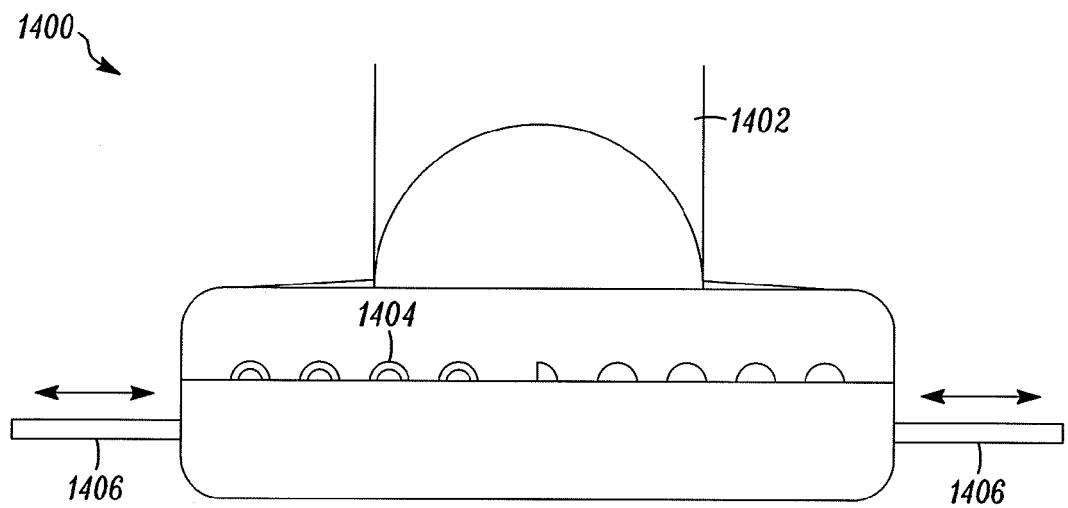
FIGS. 38A-38C are end-on views of a distal portion of a tissue modification device according to various alternative embodiments of the present invention.

With reference now to FIG. 38A, an end-on view of one embodiment of a tissue modification device 1400 shows that anchoring members 1406 may alternatively comprise one or more deployable support members, which may be extended laterally out of a distal shaft portion 1402 to anchor in tissue and support distal shaft portion 1402 and a tissue modifying member 1404. Any desired number, size, shape and configuration of lateral anchoring members 1406 may be used in various embodiments.

Figure 38B:
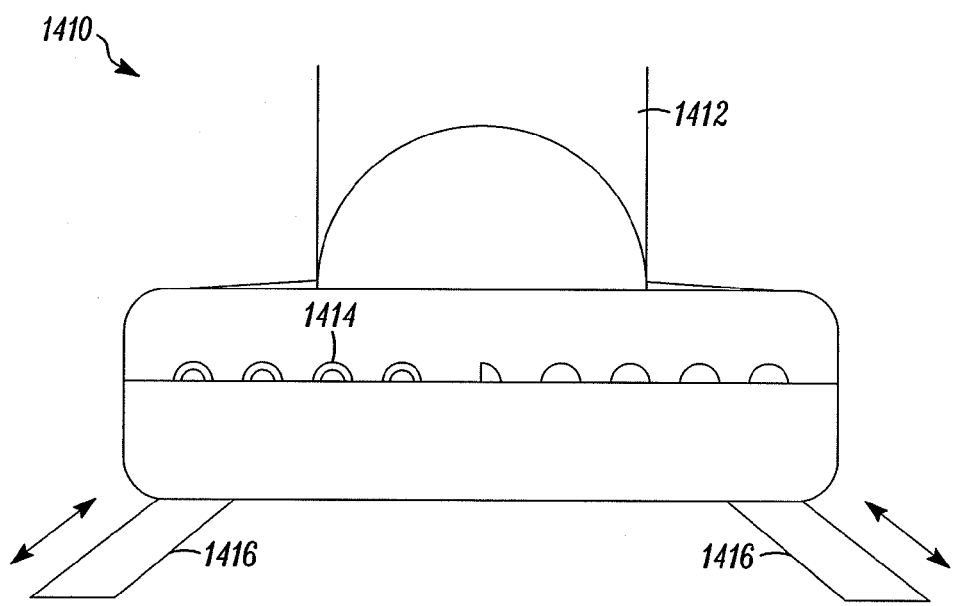

FIG. 38B shows an alternative embodiment in which a tissue modification device 1410 includes anchoring members 1416, which extend laterally and inferiorly from a distal shaft portion 1412 to support distal shaft portion 1412 and tissue modifying member 1414.

Figure 38C:
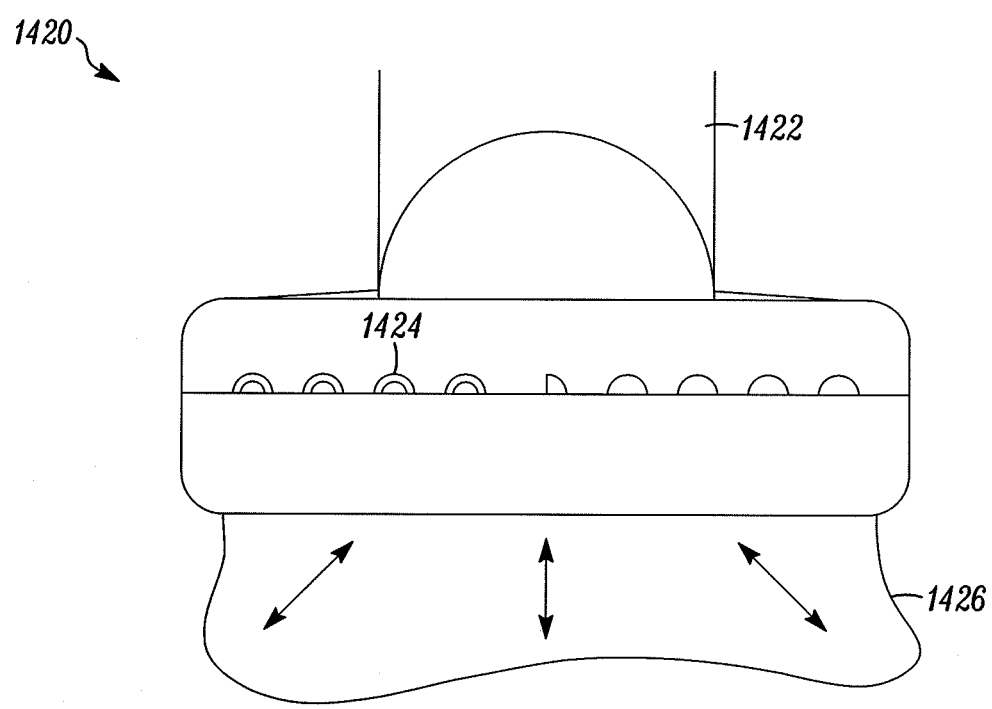

In yet another embodiment, as shown in FIG. 38C, an inflatable balloon 1426 may be included on a distal shaft portion 1422 of a tissue modification device 1420 to support distal shaft portion 1422 and tissue modifying member 1424.

Figure 39A:
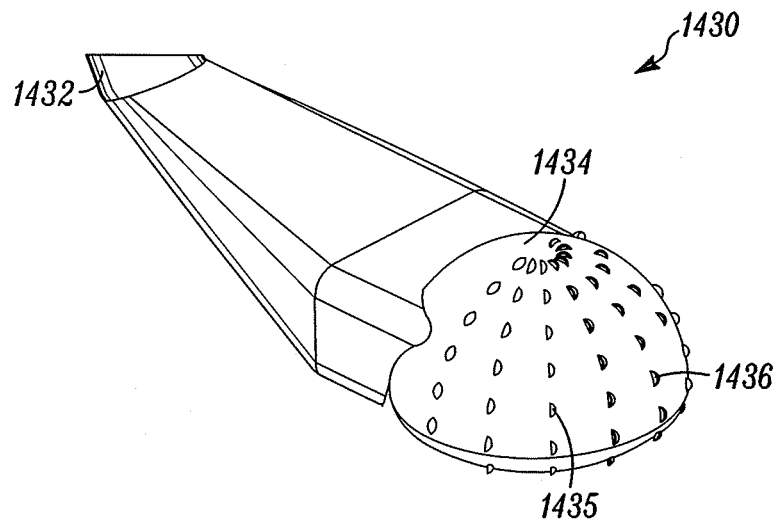
FIGS. 39A-39D are perspective (FIG. 39A), cross-sectional (FIG. 39B) and top (FIGS. 39C and 39D) views of a distal portion of a tissue modification device according to one embodiment of the present invention.
Figure 39B:
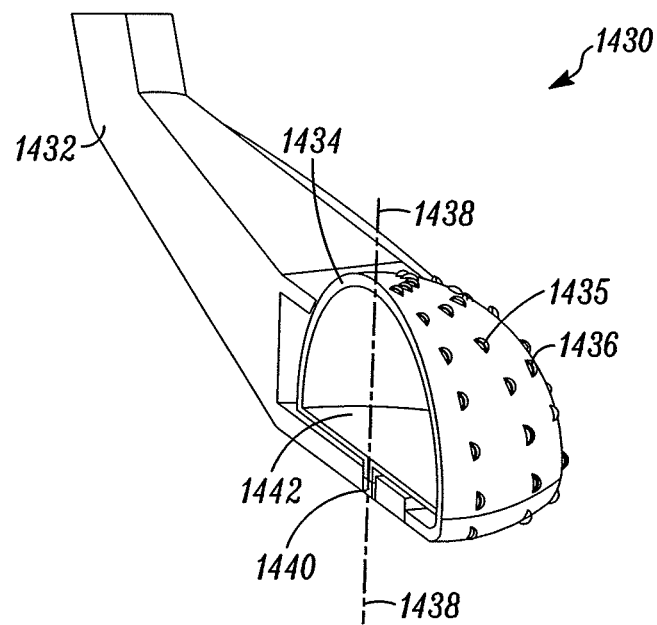
Figure 39C:
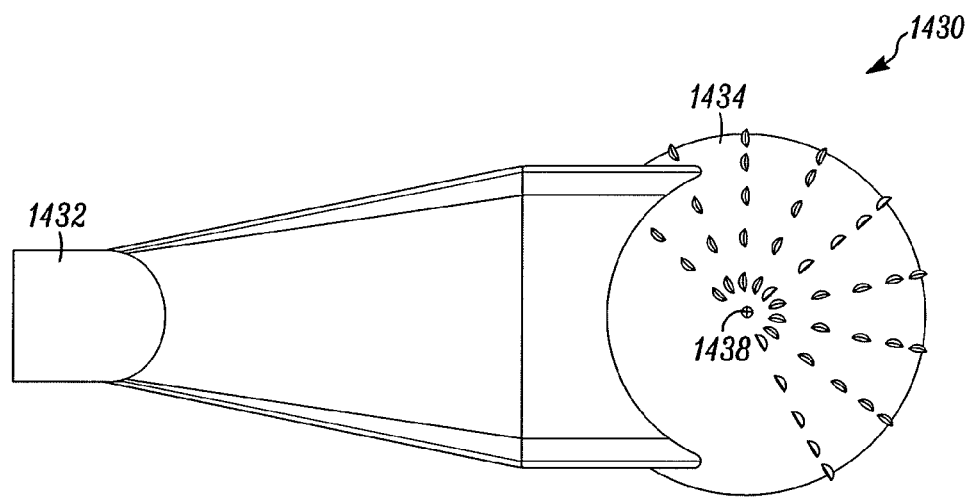
Figure 39D:
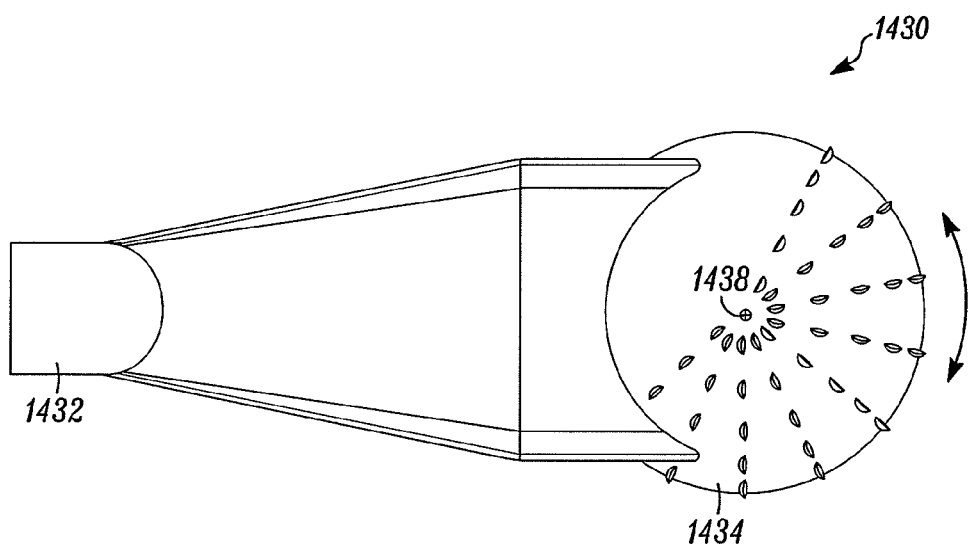

Referring now to FIGS. 39A-39D, in another alternative embodiment, a tissue modification device 1430 may suitably include a shaft 1432 and a semicircular tissue modifying member 1434. Tissue modifying member 1434 may include multiple cup-shaped blades 1435, each having a cutting edge 1436, and may rotate about a central axle 1440 that defines a central axis of rotation 1438. In some embodiments, as shown in FIG. 39B, tissue modifying member 1434 may be hollow and may include a chamber 1442 which may collect cut tissue for removal from the patient. Cups 1435 may be in fluid communication with chamber 1442 such that at least some of the tissue removed by cups 1435 enters chamber 1442. Suction may be applied to enhance the capture of tissue in chamber 1442 and/or to remove tissue from chamber 1442 proximally through shaft 1432.

Each cup 1435 may be spaced apart from adjacent cups 1435 at regular angle intervals, for example, in longitudinal and/or latitudinal direction around tissue modifying member 1434. Cups 1434 may be disposed on all or part (FIGS. 39C and 39D) of the perimeter of tissue modifying member 1434. Tissue modifying member 1434 may rotate, in various embodiments, either clockwise, counterclockwise or both. In some embodiments, tissue modifying member 1434 may have clockwise and/or counterclockwise rotational limits. For example, such rotational limits may comprise from about −180° to about 180°, or alternatively from about −90° to about 90°, or alternatively from about −45° to about 45°. In some embodiments, tissue modification device 1430 may be counterbalanced (e.g., to minimize vibrations caused by the oscillating or otherwise rotating tissue modifying member 1434 during use). For example, shaft 1432 may comprise an offset-weighted rotating balance shaft.

Figure 40A:
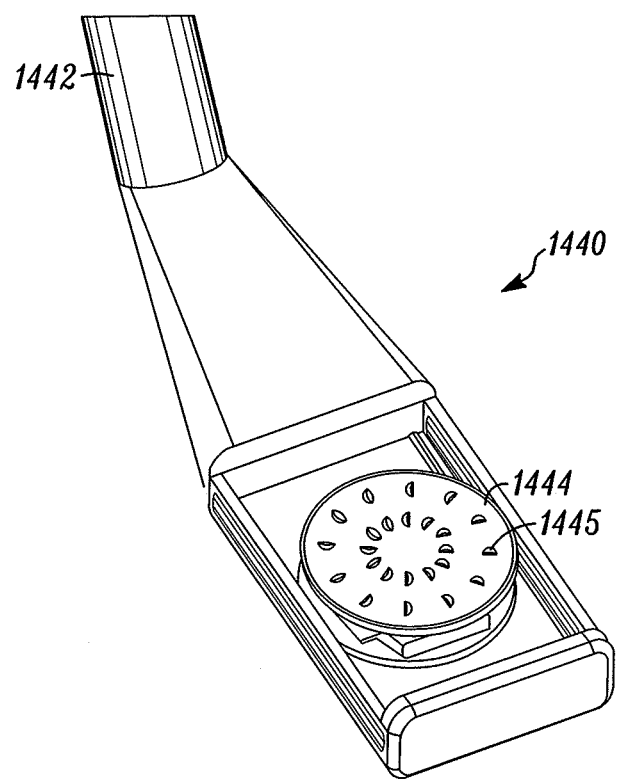
FIGS. 40A-40F are perspective (FIG. 40A), cross-sectional perspective (FIG. 40B), and cross-sectional side (FIGS. 40C-40F) views of a distal portion of a tissue modification device according to an alternative embodiment of the present invention.
Figure 40B:
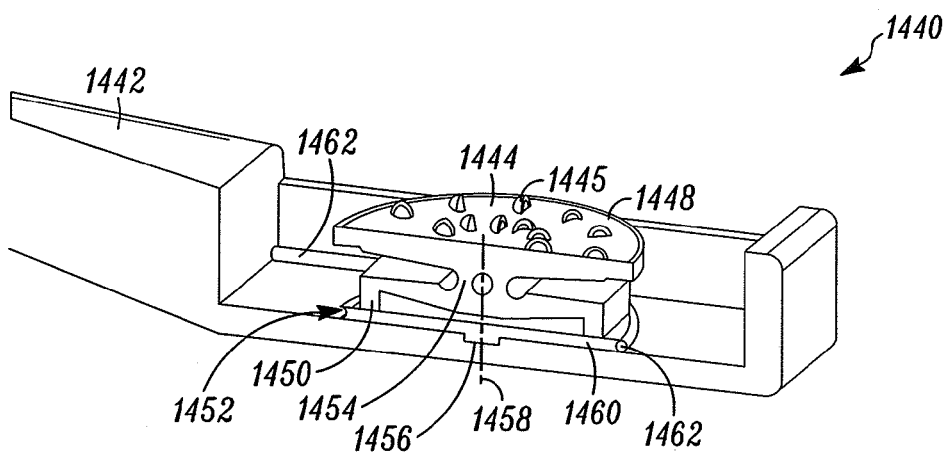
Figure 40C:
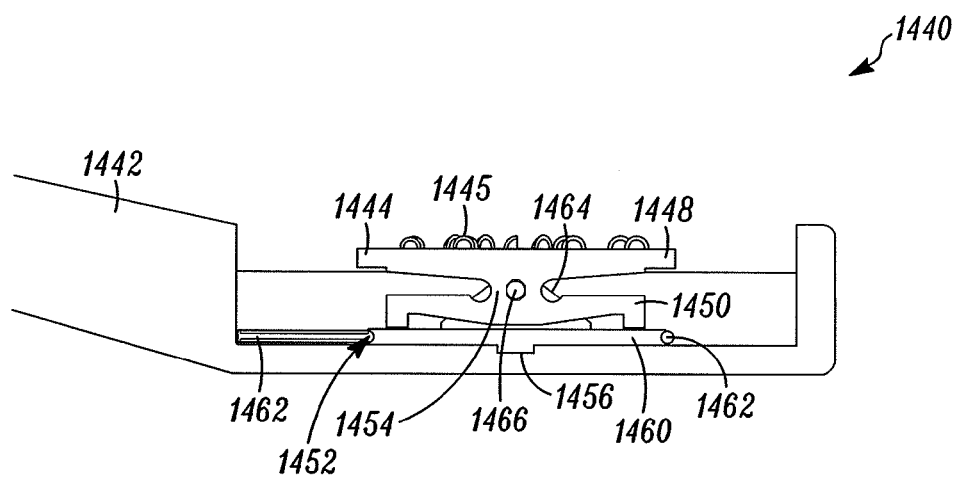

Referring now to FIGS. 40A-40F, another alternative embodiment of a tissue modification device 1440 may include a shaft 1442, and a tissue modifying member 1444 including multiple cutting members 1445. (In alternative embodiments, tissue modifying member 1444 may include an abrasive surface in place of cutting members 1445.) As shown in FIGS. 40B and 40C, tissue modifying member 1444 may include a platform 1448, multiple cutting members 1445, an axle 1456 defining an axis of rotation 1458, a bottom plate 1450, a drive groove 1452, a cross beam 1454, and a base plate 1460. Device 1440 may further include a tissue modifying drive shaft 1462. Base plate 1460 may be rigidly attached to a mount 1464 (FIG. 40C). Platform 1448 may be integrated with and/or attached to bottom plate 1450 at cross beam 1454 or, in an alternative embodiment, at a center shaft (not shown). Cross beam 1454 may include a stress relief channel 1466 (FIG. 40C). Mount 1464 may be rotatably attached to stress relief channel 1466. For example, mount 1464 may have one or more protruding beams that may extend into stress relief channel 1466. Mount 1464 may be on one or both sides of the tissue modifying member 1444. Mount 1464 may be biased with respect to stress relief channel 1466, for example, to force cross beam 1454 to a configuration (e.g., perpendicular) with respect to base plate 1460 and bottom plate 1450, as shown in FIGS. 40B and 40C.

In various embodiments, platform 1448 may be flexibly and/or rigidly integrated and/or attached to cross beam 1454. Bottom plate 1450 may be flexibly and/or rigidly integrated and/or attached to cross beam 1454. Base plate 1460 and/or bottom plate 1450 and/or cross beam 1454 may be attached and/or integrated to drive shaft 1462. For example, the tissue modifying member 1444 may include a drive groove, and the drive groove may be configured to receive drive shaft 1462.

Figure 40D:
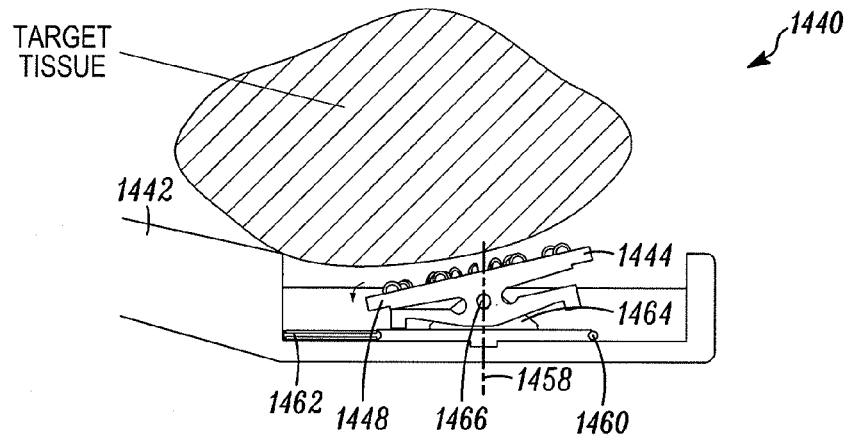
Figure 40E:
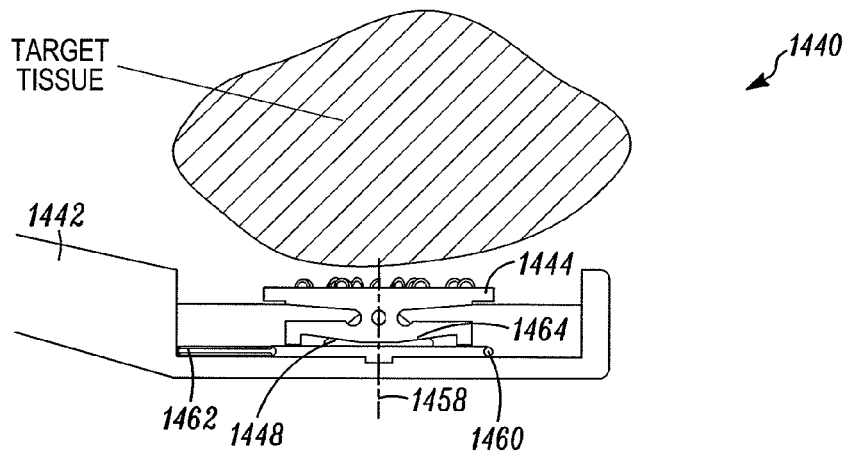
Figure 40F:
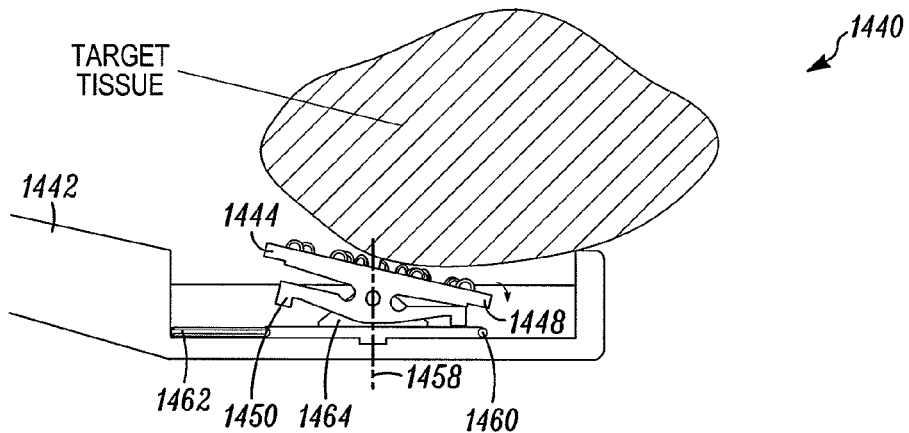

FIGS. 40D-40F demonstrate that tissue modifying member 1444 may flex to accommodate and more effectively modify target tissue from a number of orientations. FIG. 40D illustrates that the target tissue may be proximal to rotational axis 1458. Top plate 1448 may rotate with respect to bottom plate 1450. Additionally, all or part of bottom plate 1450 may rotate with respect to base plate 1460. Top plate 1448 may rotate passively (e.g., forced by pressure against the target tissue) or actively (e.g., driven by a motor or electrical current).

FIG. 40E illustrates that the target tissue can be substantially aligned with rotational axis 1458, while FIG. 40F illustrates that the target tissue can be distal to rotational axis 1458.

Figure 41A:
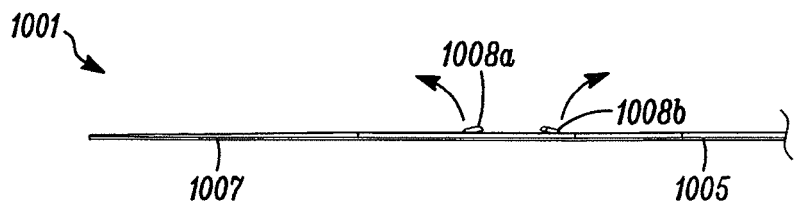
FIGS. 41A and 41B are side views of a portion of a bladed tissue modification device according to one embodiment of the present invention.
Figure 41B:
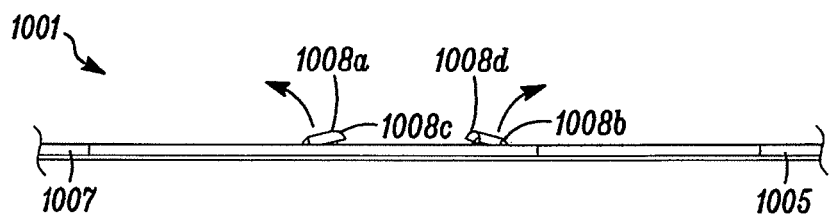

Referring now to FIGS. 41A and 41B, an alternative embodiment of a tissue modification device suitably includes an elongate body 1005 having a distal portion 1007, a distal cutting blade 1008a, and a proximal cutting blade 1008b, each blade 1008 having a cutting edge 1008c, 1008d. In this embodiment, distal cutting blade 1008a and proximal cutting blade 1008b may be rotated away from elongate body 1005 to further expose cutting edges 1008c, 1008d. The height of cutting edges 1008c, 1008d relative to the elongate body 1005 may be used, for example, to control the depth of the cut into hard and/or soft target tissue.

The embodiment shown in FIGS. 41A and 41B, as well as many of the embodiments described below, include two movable, opposing blades 1008a, 1008b, which may be moved toward one another to cut tissue. Alternative embodiments, however, may include two immobile blades, one movable blade and one immobile blade, one movable blade, one immobile blade, more than two immobile blades facing in one direction, more that two immobile blades facing in different directions, a movable blade and a backstop against which the blade may be driven, or any other suitable combination of movable and/or immobile blades. Furthermore, any blade of any given embodiment may have any suitable shape, size and overall configuration. In some embodiments, blades may be flat, while in others they may be curved, squared off, ridged, bent or the like. Blades may be long or short, multiple blades may be aligned closely one after the other, such as in a typical multi-blade razor used for shaving a face, multiple blades may be disposed apart from one another by several millimeters or even centimeters, and/or the like. Blades may have any suitable amount of sharpness or dullness, and in some embodiment a combination of sharper and duller blades may be used. Therefore, although exemplary embodiments of blades are described in detail above and below, any other suitable blades or combinations of blades may be substituted in various embodiments, without departing from the scope of the present invention.

In the embodiments described previously or in any other embodiments described herein, blades may be fabricated from metals, polymers, ceramics, composites or any other suitable material or combination of materials. According to various embodiments, suitable metals for blades may include, but are not limited to, stainless steel (303, 304, 316, 316L), nickel-titanium alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Polymer materials include nylon, polyester, Dacron®, polyethylene, acetal, Delrin® (DuPont), polycarbonate, nylon, polyetheretherketone (PEEK), and polyetherketoneketone (PEKK). In some embodiments where polymers are used, such polymers may be glass-filled or carbon-filled to add strength and stiffness. Ceramics may include, but are not limited to, aluminas, zirconias, and carbides. Blades may be manufactured using skills known in the art, for example, metal injection molding (MIM), CNC machining, injection molding, grinding, electrodischarge madhining (EDM), sheet metal bending, etching, electrodeposition, or the like. Pull wires 1011 may similarly be fabricated from any suitable material and may have any of a number of suitable shapes and dimension. In some embodiments, for example, pull wires 1011 may be made from metal or polymer and may have substantially circular, oval, rectangular or square cross sections, although this is by no means a comprehensive list. In some embodiments, pull wires 1011 may range in diameter from about 0.001 inches to about 0.10 inches, and more preferably between about 0.010 inches and 0.020 inches. Other portions of a tissue modification device, such as a cover over one or more blades or other features, may be made of any suitable material now known or hereafter discovered. A blade cover, for example, may be fabricated in various embodiments of one or more polymeric materials, such as nylon, silicone, polyetheretherketone (PEEK), polyetherketoneketone (PEKK), polytetrafluoroethylene (PTFE), polyurethane (Tecothane,), Pebax (co, USA), polycarbonate, Delrin (co, USA), high-density polyethylene (HDPE), low-density polyethylene (LDPE), HMWPE, UHMWPE, or the like. In some embodiments, one or more materials may be chosen for their compatibility with one or more imaging techniques or systems, such as magnetic resonance imaging (MRI), for example.

In various embodiments, elongate body 1005 may include one or more hollow chambers (not shown) at or near a distal portion of body 1005. Such hollow chamber(s) may serve any of a number of suitable functions. In some embodiments, for example, a chamber may be located distal and/or proximal to one or more blades 1008a, 1008b and may serve to collect removed tissue during and/or after a tissue modification procedure. In some embodiments, one or more blades 1008a, 1008b may help push removed tissue into such a chamber or chambers. In some embodiments, one or more chambers may house one or more blades 1008a, 1008b, such that blades 1008a, 1008b are housed within the chamber(s) while elongate body 1005 is passed into a patient and between target and non-target tissues. Once elongate body 1005 is in a desired position, blades 1008a, 1008b may then be deployed out of one or more windows or similar openings in the chamber(s) to remove or otherwise modify tissue. Such chambers may include, in various embodiments, a hollow distal portion or nosecone of elongate body 1005, a hollow portion of elongate body 1005 just proximal to proximal cutting blade 1008b, and/or the like.

Figure 42A:
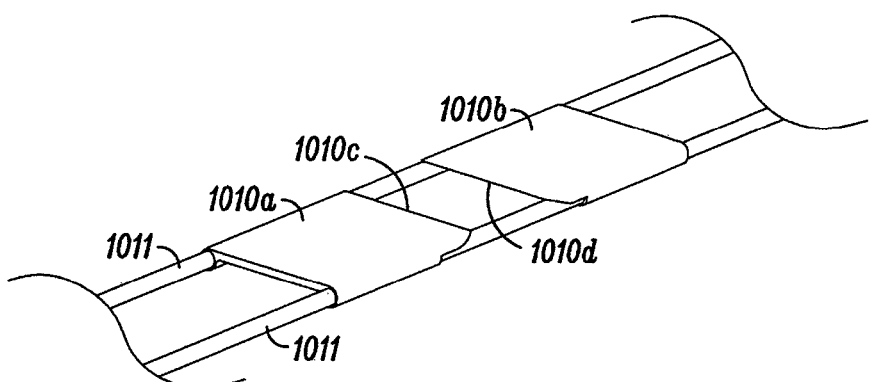
FIGS. 42A and 42B are perspective views of a portion of a bladed tissue modification device according to an alternative embodiment of the present invention.
Figure 42B:
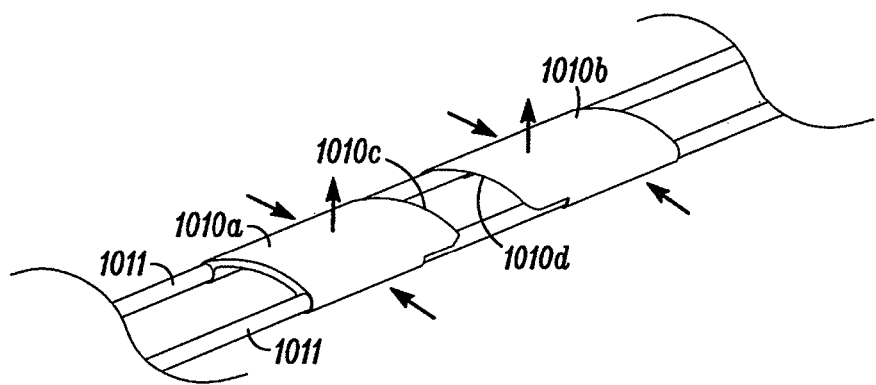

Another embodiment, as shown in FIGS. 42A and 42B, suitably includes a thin distal cutting blade 1010a and a thin proximal cutting blade 1010b, each blade 1010 having a cutting edge 1010c, 1010d and both blades 1010 being attached to two parallel pull wires 1011. In FIG. 42A, blades 1010a, 1010b are shown their flat configuration. In one embodiment, as shown in FIG. 42B, when a load is applied that is planar to pull wires 1011 and normal to the long axis of pull wires 1011, thin blades 1010a, 1010b flex or bow out of plane to increase the height of the cutting edges 1010c, 1010d.

Figure 43A:
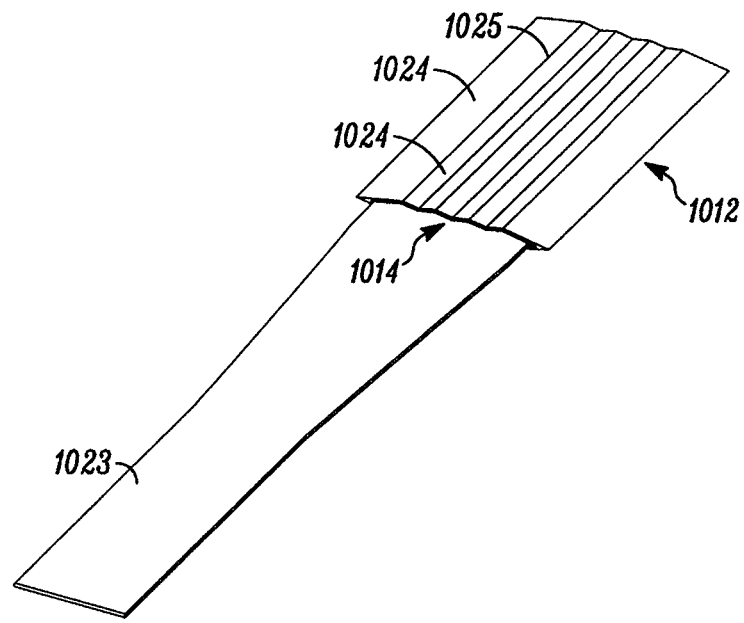
FIGS. 43A and 43B are perspective views of a portion of a bladed tissue modification device according to an alternative embodiment of the present invention.
Figure 43B:
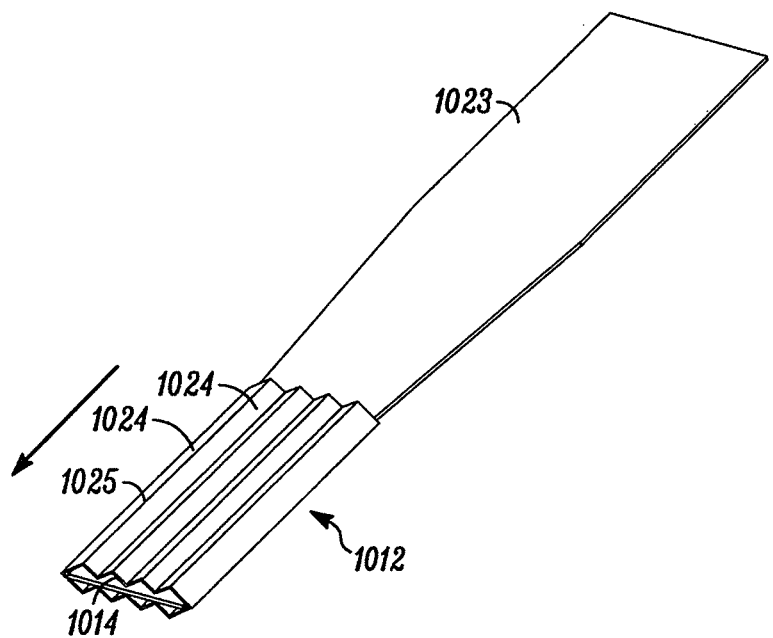

Referring now to FIGS. 43A and 43B, another alternative embodiment of a blade 1012 that changes shape as it translates along a device is shown. Blade 1012 includes multiple flat members 1024 joined at edges 1025, which may form bends, creases, folds, or hinges that allow blade 1012 to widen (FIG. 43A) and contract (FIG. 43B). Blade 1012 includes a cutting edge 1014, which may be formed using methods known in the art, for example, grinding, molding, cutting, EDM machining, etching, laser cutting, electropolishing, electrodeposition, etc. In various embodiments, blade 1012 may be made from metal, polymer, or a combination of both. In some embodiments, blade 1012 may be translated along a central member 23 that causes blade 1012 to widen and contract at various locations along central member 23. When blade 1012 is located over a wider section of central member, as in FIG. 43A, blade 1012 has a flatter, wider configuration. When blade 1012 slides or otherwise translates along central member 1023 to a narrower section, as in FIG. 43B, blade 1012 assumes a taller, narrower configuration. Such a taller configuration may facilitate cutting tissue with blade edge 1014, in some embodiments. Edges 1025 of blade 1012 allow it to change shape more readily between the wider and narrower configurations, and the bends or ridges formed in blade 1012 in the narrower configuration (FIG. 43B) may help limit the amount of material that is removed with each pass of blade 1014 along a surface of target tissue.

Figure 44A:
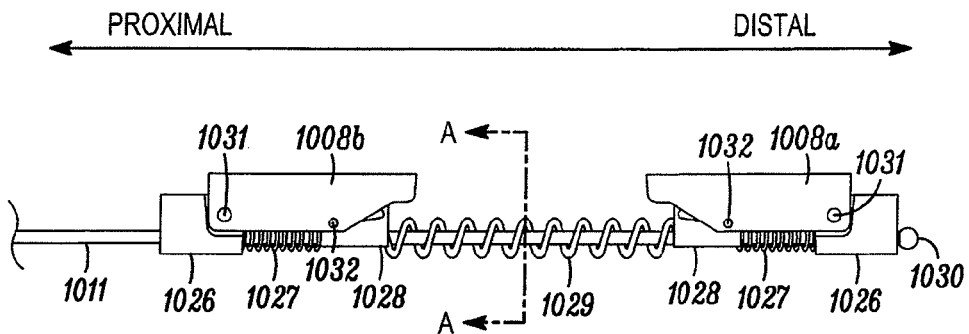
FIGS. 44A-44D are side, end-on cross-sectional, top, and lateral cross-sectional views, respectively, of a blade mechanism of a tissue modification device according to one embodiment of the present invention.

Referring now to FIGS. 44A-44D, one embodiment of a blade system for a tissue modification device is shown. FIG. 44A is a side view showing distal cutting blade 1008a and proximal cutting blade 1008b, each of which is free to pivot about an external pin 1031 that may be rigidly fixed to an external support block 1026 that is free to slide along a pull wire 1011. An internal pin 1032 may be contained within an angled slot 1033 (shown in FIG. 44D) in an internal support block 1028 that freely slides along pull wire 1011. A wire stop 1030 is securely fixed to the end of pull wire 1011 to prevent pull wire 1011 from pulling through distal external support block 1026 as axial force is applied to pull wire 1011. In various embodiments, wire stop 1030 may include but is not limited to a mechanical squeeze-type clamp, a ball formed at the end using a laser, TIG welder, or torch, a crimped hypo-tube, a sleeve with a set-screw, a loop, bend or twist in the wire, or the like. A pair of external springs 1027 may maintain blades 1008a, b in a low-profile (or "flat") configuration. An internal spring 1029 may act to separate blades 1008a, 1008b.

Figure 44B:
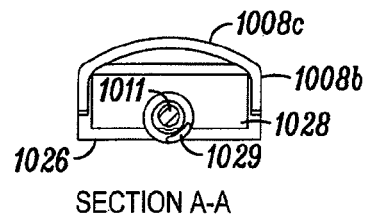

FIG. 44B provides a cross-sectional view along the line A-A in FIG. 44A. Proximal cutting blade 1008b is shown to have a curved profile, and centrally located pull wire 1011 and internal spring 1029 are also shown. Internal support block 1028 and external support block 1026 remain within the profile of proximal cutting blade 1008b. Cutting blade edge 1008c is positioned in a low profile configuration.

Figure 44C:
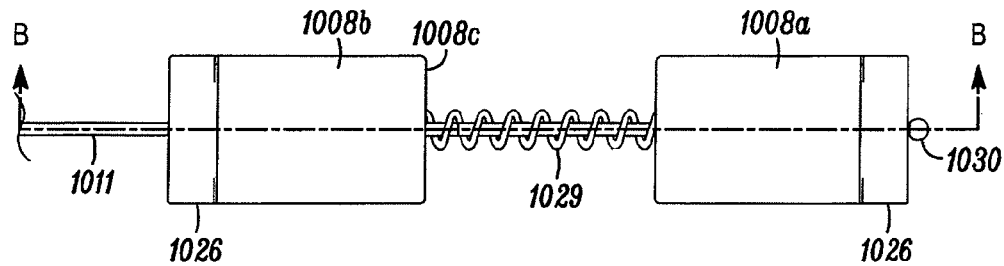

As shown in FIG. 44C, in one embodiment, the width of distal blade 1008a and proximal blade 1008b may be approximately the same as the width of external support block 1026. Pull wire 1011 may be centrally located to facilitate uniform movement of the cutting blade 1008a and therefore uniform cutting with cutting blade edge 1008c.

Figure 44D:
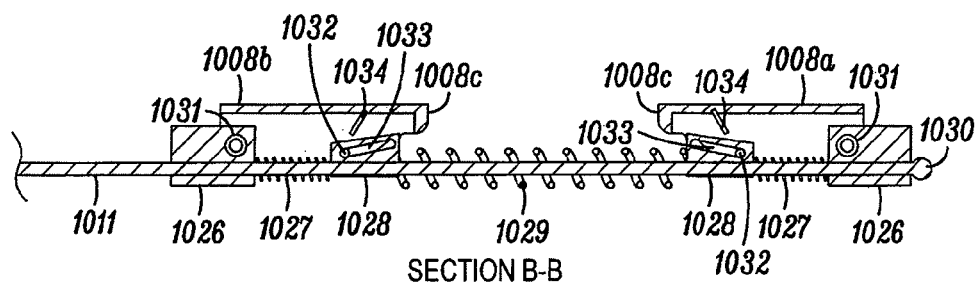

In the cross-sectional view of FIG. 44D, an angled slot 1033 is shown that constrains internal pin 1032 that controls the height of blades 1008a, 1008b at a given axial displacement of internal support block 1028 relative to external support block 1026. In some embodiments, a baffle 1034 may be used as a one-way mechanism for debris transport down the open channel of blade 1008a, 1008b.

Figure 45A:
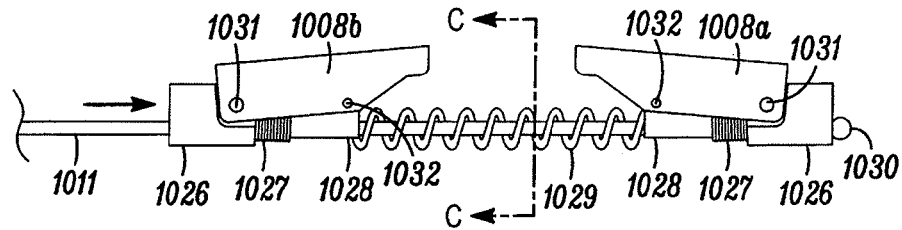
FIGS. 45A-45D are side, end-on cross-sectional, top, and lateral cross-sectional views, respectively, of the blade mechanism of FIGS. 44A-44D, shown with the blades disposed at an angle, relative to the mechanism according to one embodiment of the present invention.
Figure 45B:
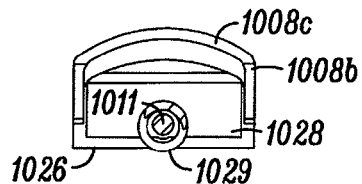
Figure 45C:
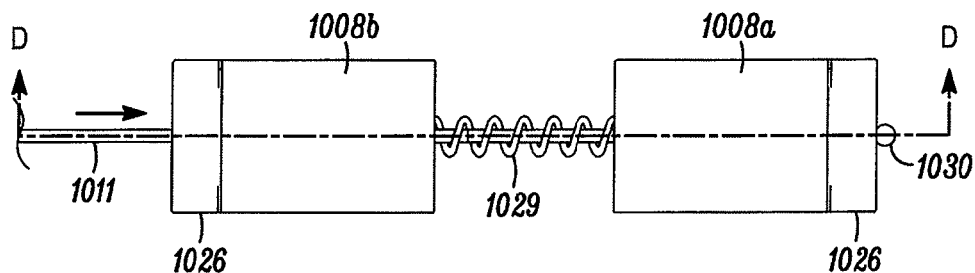
Figure 45D:
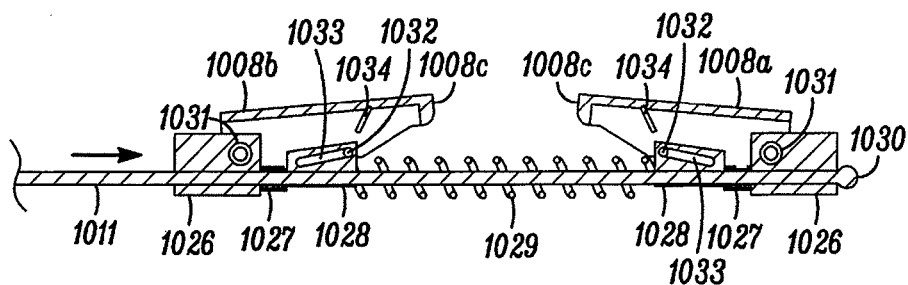

Referring now to FIGS. 45A-45D, in one embodiment, as proximal external support block 1026 is driven distally towards wire stop 1030, external springs 1027 compress to increase the height of the proximal and distal cutting blades 1008a, 1008b, as shown in side view in FIG. 45A. External springs 1027 may have a lower spring rate (lb./in.) than that of internal spring 1029, such that external springs 1027 displace more readily than internal spring 1029 during the initial loading of the mechanism in order to preferentially drive blades 1008a, 1008b upward. This increase in blade height may help control the amount of tissue material that will be removed during a cutting cycle. The blade height can be adjusted by adjusting the length, angle, and endpoint positions for angled slot 1033. To help support blades 1008a, 1008b during the cutting process, blades 1008a, 1008b may stop at the limits of the angled slot 1033 and may also be limited by the angled cut on the sides of external support blocks 1026 near external pin 1031.

Figure 46A:
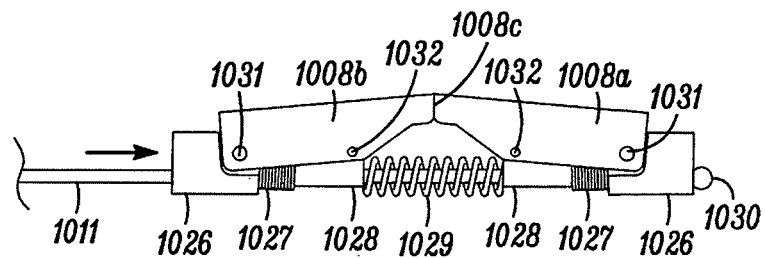
FIGS. 46A-46C are side, top, and lateral cross-sectional views, respectively, of the blade mechanism of FIGS. 45A-45D, shown with the blades disposed at an angle with their cutting edges brought together according to one embodiment of the present invention.
Figure 46B:
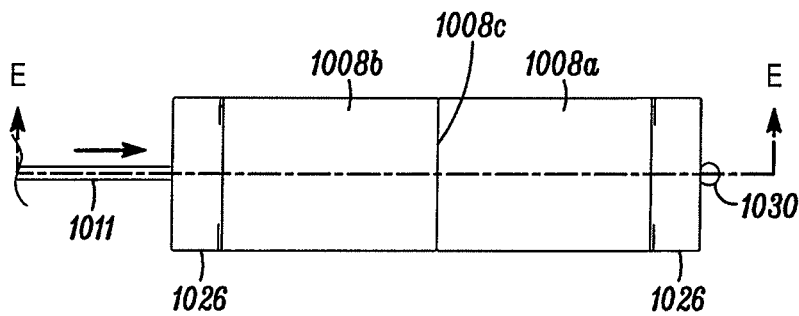
Figure 46C:
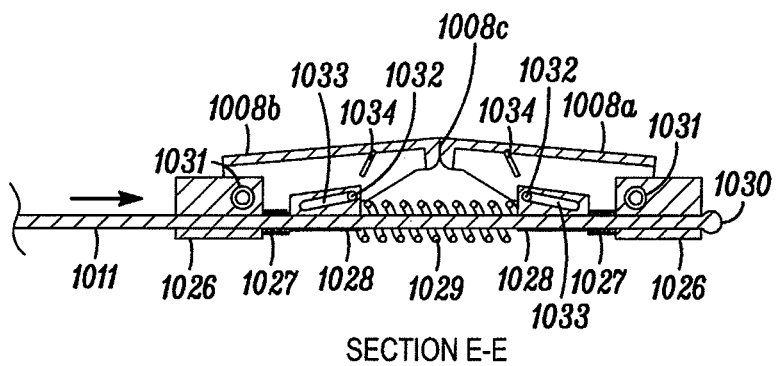

With reference now to FIGS. 46A-46C, in one embodiment blades 1008a, 1008b may be made to rotate to a desired height, such as their maximum height, and may then be driven toward one another by applying an additional load to further compress internal spring 1029, as depicted in side-view in FIG. 46A. In some embodiments, blades 1008a, 1008b are driven together until cutting blade edges 1008c contact each other to complete a cutting cycle. In some embodiments, relative spring rates for external spring 1027 and internal spring 1029 may be customized/selected to provide a desired cutting action and penetration behavior for blades 1008a, 1008b into target tissue. After a cutting cycle is complete, blades 1008a, 1008b may be driven apart and further pushed into a low profile state by internal spring 1029 and external springs 1027. Baffle 1034 may be displaced as debris is driven into the blade channel, and baffle 1034 then may return to its original position to hold the debris in place. In some embodiments, for example, baffle 1034 may include a metal tab or a polymer flap molded into blade 1008a, 1008b. An alternative debris capture mechanism is shown in the cross-sectional view of blade 1008 depicted in FIG. 47E. Multiple ramps 1034a and stops 1034b allow debris to slide away from cutting edge 1008c but prevent the debris from sliding back.

Figure 47A:
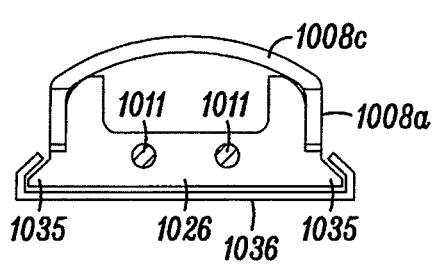
FIGS. 47A-47D are cross-sectional end-on views of various embodiments of a blade mechanism of a tissue modification device with a track having different configurations in the various embodiments.
Figure 47B:
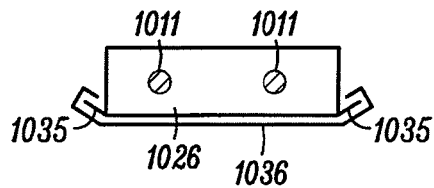
Figure 47C:
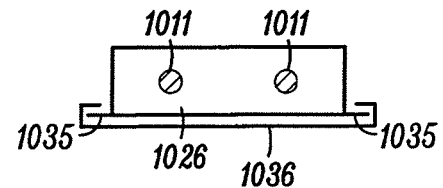
Figure 47D:
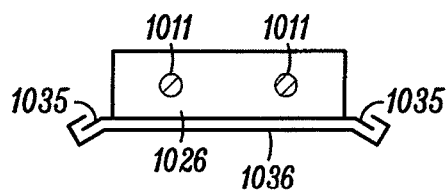
Figure 47E:
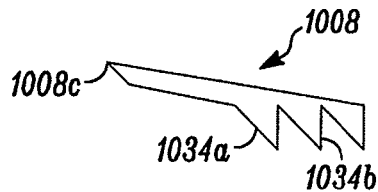
FIG. 47E is a cross-sectional view of a blade with means for directing cut tissue according to one embodiment of the present invention.

Referring to FIG. 47A, in one embodiment, to prevent a cutting blade 1008a from rotating about the axis of a single pull wire 1011 and/or to allow for more force or more distributed force along cutting edge 1008c, multiple pull wires 1011 may be used to actuate the blade mechanism. In addition, external support block 1026 may optionally include ridge features 1035 that slidably engage with a track 1036 that may serve as an anti-rotation mechanism and may also provide additional strength and stiffness along the length of the blade mechanism. In various embodiments, orientation of such ridge features 1035 may be varied. For example, ridge feature 1035 may be folded inward as in FIG. 47B, flat as in FIG. 47C or folded outward as in FIG. 47D. In various embodiments, ridge feature 1035 have any suitable shape or configuration, such as but not limited to a round, square, dove-tailed, rectangular, or triangular cross-sectional shape.

Figure 48A:
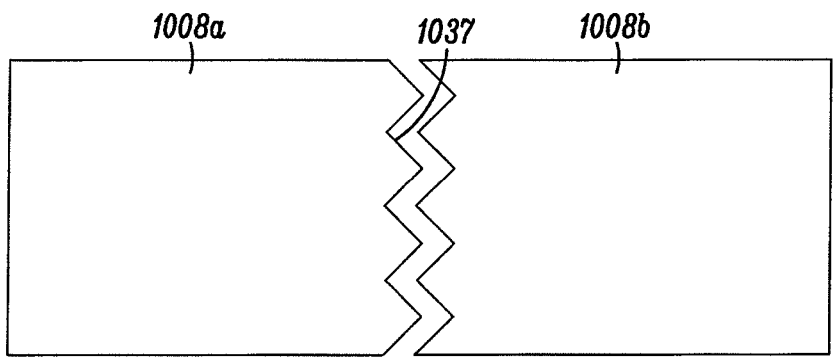
FIGS. 48A and 48B are top views of blades having alternative configurations of teeth according to alternative embodiments of the present invention.
Figure 48B:
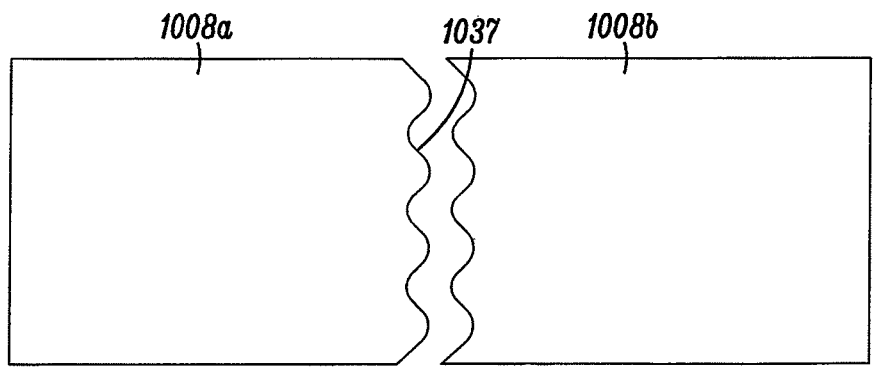

With reference now to FIGS. 48A and 48B, in various embodiments the cutting edges of blades 1008a, 1008b may have teeth 1037 that facilitate engagement with a smooth, curved, and/or hard target tissue, such as bone. One embodiment, as in FIG. 48A, may include pointed teeth 1036, while an alternative embodiment, as in FIG. 48B, may include rounded teeth 1037. Of course, any other suitable configuration may be substituted in various alternative embodiments.

Figure 48C:
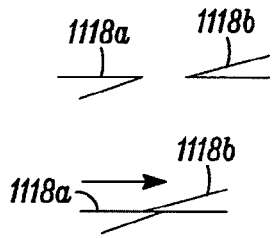
FIGS. 48C-48G are side views of various blade-blade and blade-backstop combinations according to various embodiments of the present invention.
Figure 48D:
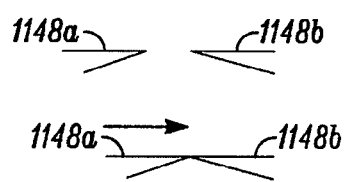
Figure 48E:
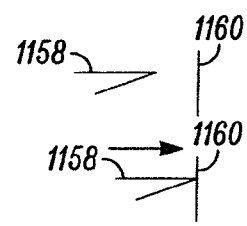
Figure 48F:
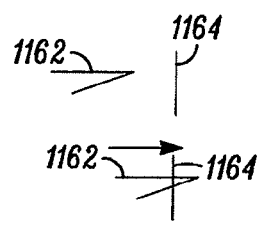
Figure 48G:
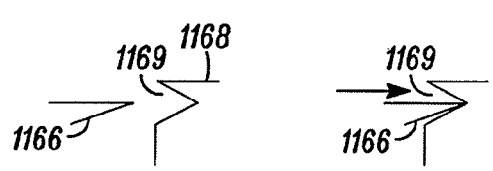

Referring now to FIGS. 48C-48G, in various embodiments, the interaction of cutting edges of two blades or one blade and a backstop may effectively modify tissue with any number of different actions. FIG. 48C depicts the cross section of two opposing blades 1118a, 1118b, which are slightly offset with their respective bevels angled opposite of each other. This may create a shearing action when blades 1118a, 1118b are brought together and pass each other as shown in the lower portion of the FIG. 48C. In FIG. 48D two blades 1148a, 1148b are in plane with similar bevels. The cutting edges of these blades 1148a, 1148b come in contact to bite tissue when blades 1148a, 1148b are brought together. In another embodiment, as in FIG. 48E, one blade 1158 may be brought into contact with a backstop 1160, which in one embodiment comprises a hard flat plane. FIG. 48F depicts a single blade 1162 brought into contact with a compliant flat plane backstop 1164. Contact of blade 1162 with such a backstop 1164 may create both a pinching and a shearing effect on tissue. In yet another embodiment, as in FIG. 48G, a single blade 1166 may be brought against a backstop 1168 having a concave pocket 1169. This may also create both a shearing and a pinching action on targeted tissue.

Figure 49A:
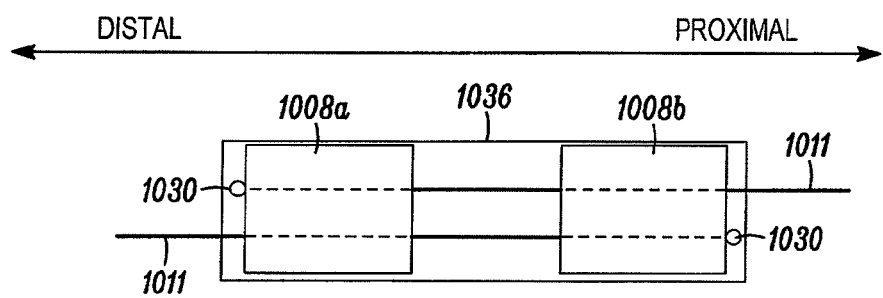
FIGS. 49A and 49B are top views of a blade and pull wire mechanism according to one embodiment of the present invention.
Figure 49B:
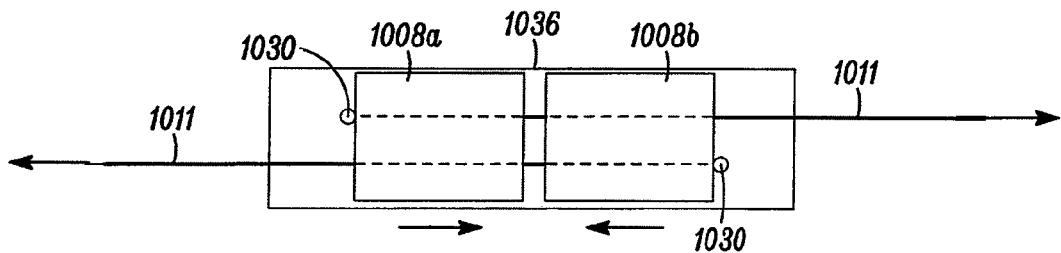

Referring to FIGS. 49A and 49B, in one embodiment, distal cutting blade 1008a and proximal cutting blade 1008b (or external support blocks 1026 that in turn are fitted with blades that pivot about the external pin 1031) may be slidably engaged in a track 1036, two pull wires 1011 may be mounted in opposite directions, and wire stops 1030 may be located on the outside of opposite blades 1008a, 1008b, as shown in top-view in FIG. 49A. By applying a force to the pull wires 1011, blades 1008a, 1008b are drawn toward the center of track 1036, as depicted in FIG. 49B.

Figure 50A:
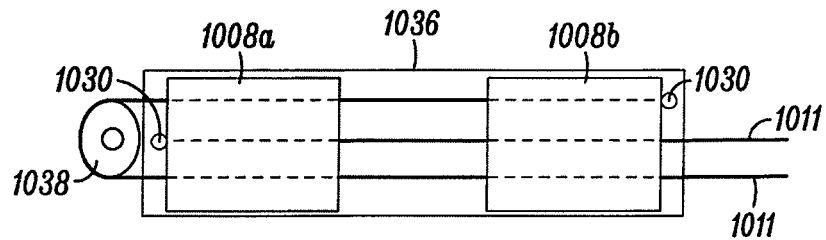
FIGS. 50A and 50B are top views of a blade and pull wire mechanism according to an alternative embodiment of the present invention.
Figure 50B:
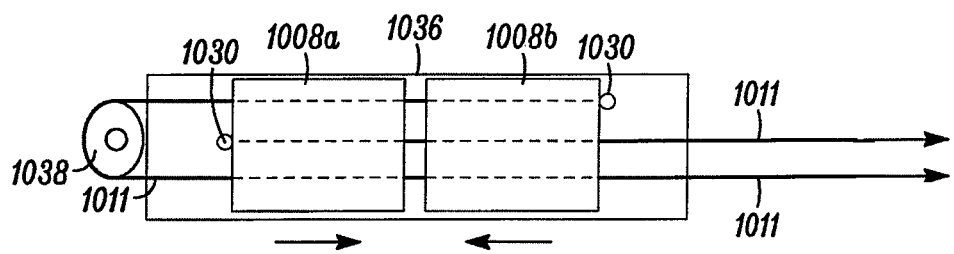

In an alternative embodiment, as in FIGS. 50A and 50B, two pull wires 1011 may be actuated from one end of a tissue modification device. In such an embodiment, a pulley 1038 (or capstan) may be used to redirect one of the wires 1011, as shown in top-view in FIG. 50A, so that the two pull wires 1011 are aligned. As depicted in FIG. 50B, actuating pull wires 1011 from the one end causes blades 1008a, 1008b to move toward the center of track 1036.

In one alternative embodiment (not pictured), similar to that in FIGS. 50A and 50B, a first pull wire may be constrained on one side of a blade by a wire stop to provide a closing motion of the blade toward a stationary blade. A second pull wire may be constrained on an opposite side of the blade by a wire stop and guided around a pulley or capstan to direct the pull wire in the same direction as the first pull wire. This second pull wire may be used to provide an opening motion of the blade away from stationary blade.

Figure 51A:
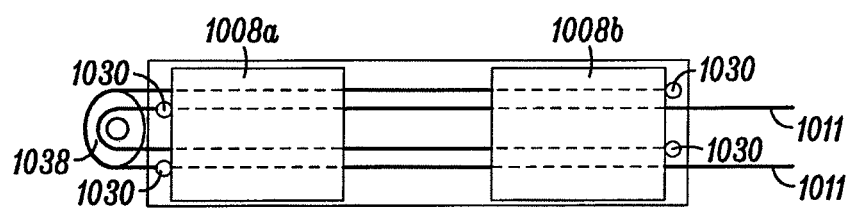
FIGS. 51A and 51B are top views of a blade and pull wire mechanism according to an alternative embodiment of the present invention.
Figure 51B:
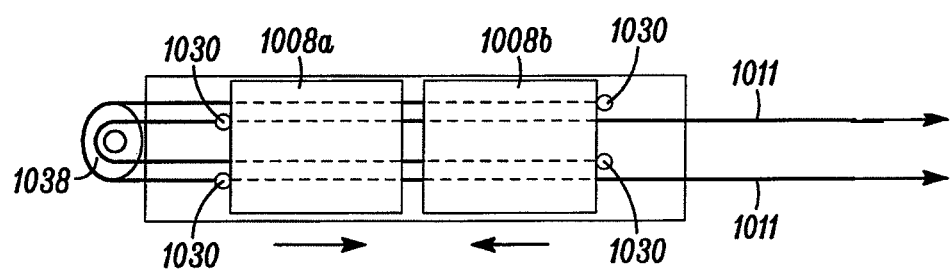

Referring now to FIGS. 51A and 51B, in another alternative embodiment, to balance or distribute the applied load on blades 1008a, 1008b more evenly (to prevent blades 1008a, 1008b from binding while sliding with or without the track) and still have pull wires 1011 actuate from one end of the device, the two pull wires 1011 may both be redirected around a double grooved pulley 1038 (or capstan), as shown in top-view in FIG. 51A. Two additional wire stops 1030 may be added to an edge of each blade 1008a, 1008b. Applying force to the pull wires 1011 causes blades 1008a, 1008b to move toward one another.

Figure 52A:
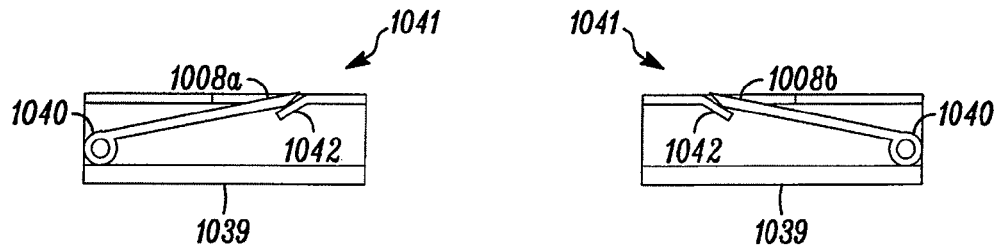
FIGS. 52A-52C are side views of a blade mechanism including a ramp and a window according to one embodiment of the present invention.
Figure 52B:
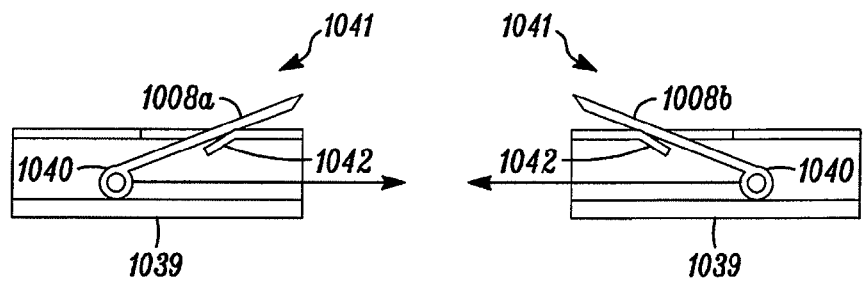
Figure 52C:
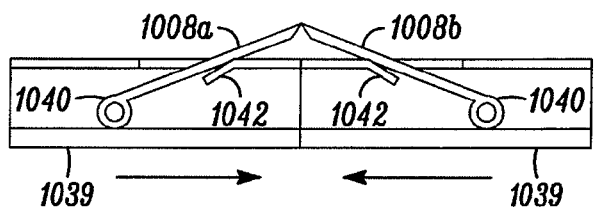

As depicted in FIGS. 52A-52C, in another embodiment, distal cutting blades 1008a and proximal cutting blades 1008b may be housed within an enclosure 1039 that has an opening 1041 and a ramp 1042 to facilitate deployment of blades 1008a, 1008b out of window. Blades 1008a, 1008b are shown in their undeployed positions in FIG. 52A. In FIG. 52B, as blades 1008a, 1008b are driven inward by an applied force via one or more wires, flexures, or mechanisms, blades 1008a, 1008b rotate about a base pivot 1040 and are driven through opening 1041 along ramp 1042 and are exposed out of enclosure 1039. FIG. 42C shows blades 1008a, 1008b in contact with one another as enclosures 1039 are driven inward to complete a cutting cycle. In some embodiments, springs (not shown) may be used to drive the mechanism apart, similar to the mechanism described in FIG. 4A, such that blades 1008a, 1008b would lay flush within enclosure 1039 once the applied force is removed.

Figures 53A, 53B:
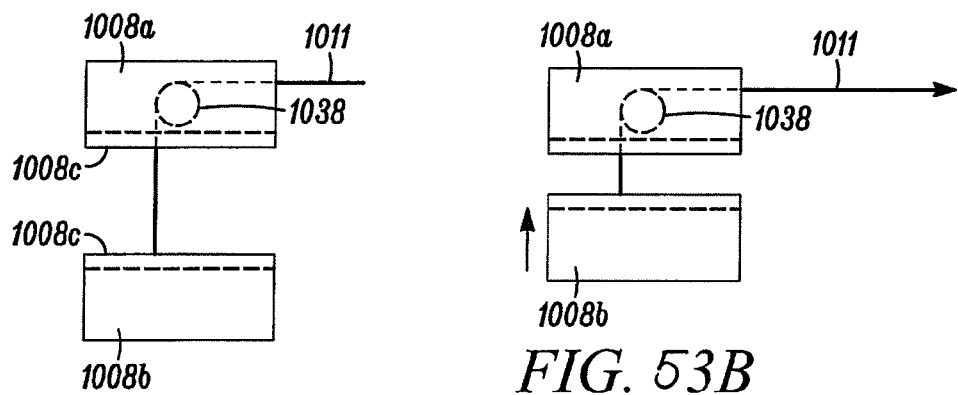
FIGS. 53A and 53B are top views of a blade and pull wire mechanism according to an alternative embodiment of the present invention.

In some embodiments, as in FIGS. 53A and 53B, blades 1008a, 1008b may also be directed to translate along an axis normal to pull wire 1011 by having pull wire 1011 change its applied direction by 90 degrees by means of a pulley 1038 (or capstan).

Figure 54A:
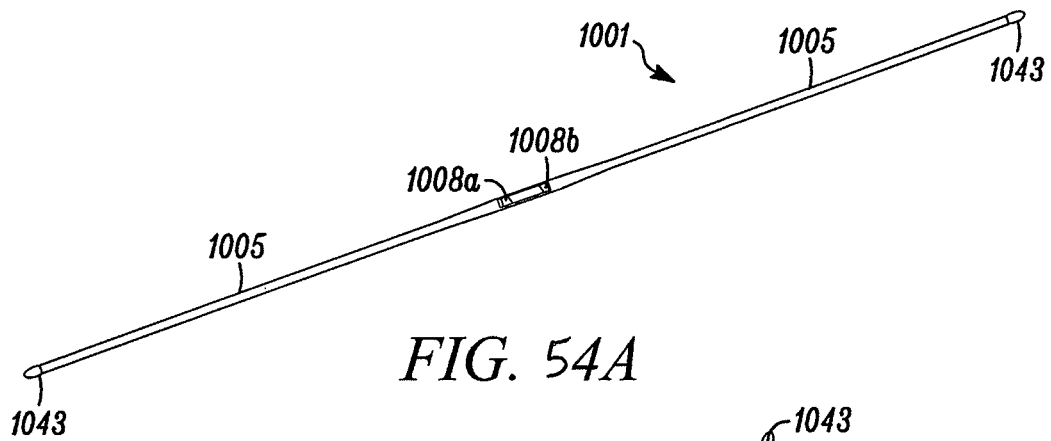
FIGS. 54A and 54B are perspective views of a tissue modification device including flexible portions and endcaps according to one embodiment of the present invention.
Figure 54B:
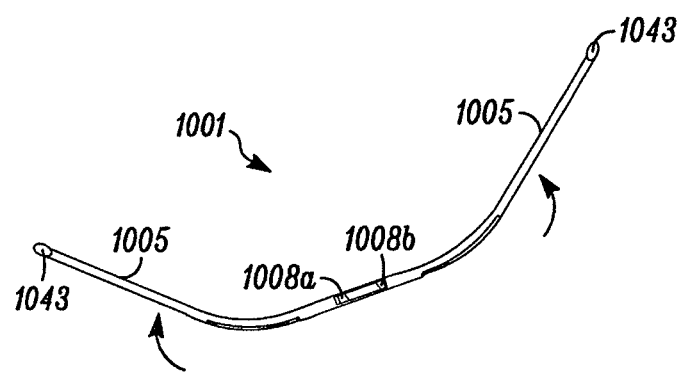

Referring to FIGS. 54A and 54B, in one embodiment, a tissue modification device 1001 may include endcaps 1043 on each end of an elongate body 1005, which endcaps 1043 are attached to pull wires 1011 in order to actuate the distal and proximal cutting blades 1008a, 1008b. In addition, as depicted in FIG. 44B, elongate body 1005, in some embodiments, may be partially flexible at various locations along its length or, in some embodiments, along its entire length. The embodiment depicted in FIG. 44B shows two flexion points where elongate body 1005 may be flexed to bend around anatomical structures. In some embodiments, encaps 1043 may be tapered to facilitate passage of device 1001 through a small incision. Encaps 1043 and elongate body 1005 may also optionally be configured to accommodate a guidewire for over-the-wire advancement to target tissue.

Figures 55A, 55B:
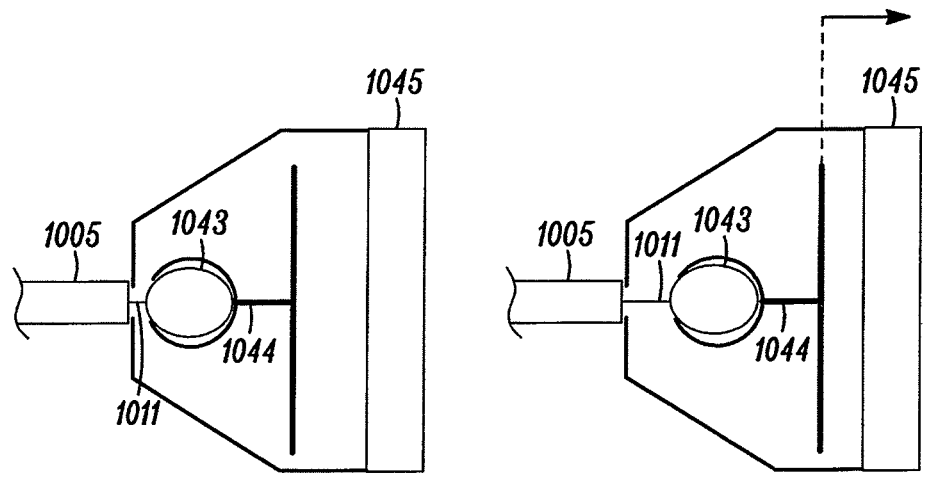
FIGS. 55A and 55B are top views of a handle mechanism of a tissue modification device according to one embodiment of the present invention.

In one embodiment, and with reference now to FIGS. 55A and 55B, endcaps 1043 may nest within a simple T-handle mechanism 1044 that is fitted within a handgrip 1045, as demonstrated in FIG. 55A. T-handle mechanism 1044 may be displaced to pull endcap 1043 that is in turn connected to pull wire 1011, as handgrip 1045 provides counter-traction to elongate body 1005. Other quickly attached and separated handle mechanisms that allow tensioning and wire actuation and/or wire constraint may alternately be used.

Referring now to FIGS. 56A and 56B, some embodiments may optionally provide for lateral movement and/or control of lateral movement of one or more cutting blades. As shown in front-view in FIG. 56A, in one embodiment a cam 1046 may be rigidly fixed to a rotatable control rod 1048 that freely rotates within a support block 1049. Support block 1049 has raised features 1047 that constrain cam 1046. Support rods 1050 prevent axial displacement of support block 1049 while allowing it to translate from side to side. A support frame 1051 may contain the mechanism and may be fitted to the body of the tissue modification device. Support block 1049 may translate to the left, for example, as depicted in FIG. 56B, as control rod 1048 is rotated counterclockwise. According to various embodiments, any of the previously disclosed cutting mechanisms may be fitted to support block 1049 to facilitate controlled lateral displacement of the cutting mechanism as actuated by control rod 1048 for cutting tissue.

FIGS. 57A and 57B show an alternative embodiment including a rotatable control rod 1048 that freely rotates within support frame 1051. Control rod 1048 is rigidly fixed to a fork or yoke 1052 that captures a positioning pin 1053. As yoke 1052 is rotated counterclockwise, for example, support block 1049 may be displaced to the right, as depicted in FIG. 57B.

Referring to top-view FIGS. 58A and 58B, in one alternative embodiment, instead of rotating a rod about the long axis of a tissue modification device, control wires 1011 may be secured to a base pulley 1054 that is rigidly fixed to a control linkage 1055. By pulling on a control wire 1011, support block 1049 may be translated to the left, as in FIG. 58B, or to the right, as in FIG. 58A.

With reference now to FIGS. 59A-59C, in some embodiments it may be advantageous to include one or more guiding or steering features on an elongate body of a tissue modification device, to facilitate guiding or steering of the body and/or one or more tissue modification members. In some embodiments, such guiding or steering features may be located adjacent or near tissue modifying members and may facilitate moving such members laterally back and forth or in any of a number of directions and/or may facilitate urging the tissue modifying members into target tissue. In other embodiments, guiding or steering members may be located along an elongate body at one or more locations distant from the tissue modifying members.

As shown in FIGS. 59A-59C, in one embodiment, a tissue modifying portion 1056, such as a blade mechanism, may be coupled with a deployable wire loop 1058 that may facilitate guiding or directing portion 1056 by bowing outward to press against tissue. A top-view depicted in FIG. 59A shows tissue modifying portion 1056 (possibly polymer or hypotube), which may contain a push wire 1057 constrained at the distal end. When a force is applied to push wire 1057, the portion of the wire contained in tissue modifying portion 1056 bows out to create a side-loop 1058, as depicted in FIG. 59B. A small feature on the end of the wire like a formed ball (or clamp) 1059 can be constrained at distal end of tissue modifying portion 1056. Alternately, as in FIG. 59C, wire 1057 may be pulled to bow out a portion of side loop 1058. In either case, side loop 1058 may push against tissue on one side to force tissue modifying portion 1056 laterally to the other side.

Referring to FIGS. 60A and 60B, in some embodiments, side-loop 1058 may be toggled from side to side by means of a distal tip 1060 to facilitate control and/or steering of tissue modifying portion 1056.

Figure 61A:
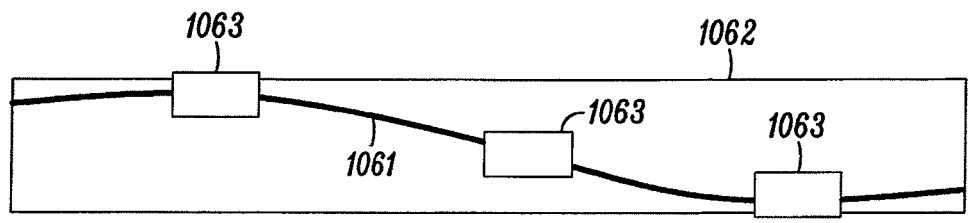
FIGS. 61A and 61B are top and cross-sectional side views, respectively, of a portion of a tissue modification device including a track along which one or more blades slide according to one embodiment of the present invention.
Figure 61B:
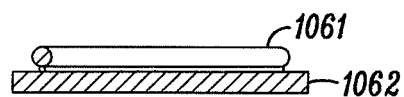

In yet another embodiment, as depicted in FIGS. 61A and 61B, a mechanism to provide lateral position control of a cutting blade mechanism 1063 may include a track (or monorail) 1061 fixed to a backing plate 1062. Cutting blade mechanism 1063 may be advanced and retraced along track 1061 to provide different lateral positions, as depicted in top view in FIG. 61A. FIG. 61B shows a cross-sectional view of track 1061 and backing plate 1062.

Figure 62:
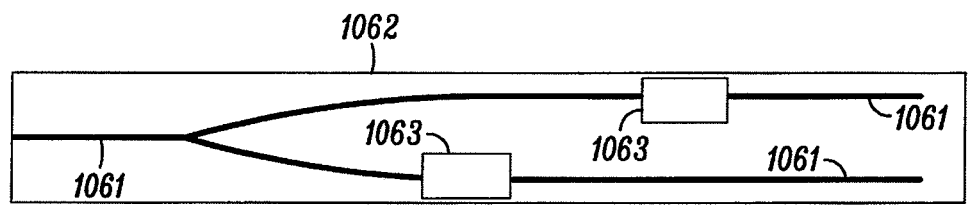
FIG. 62 is a top view of a portion of a tissue modification device including a track along which one or more blades slide according to an alternative embodiment of the present invention.

In an alternative embodiment, as shown in FIG. 62, a track 1061 may include a junction, which may facilitate directing cutting blade mechanism 1063 from one side to another of backing plate 1062.

Figure 63A:
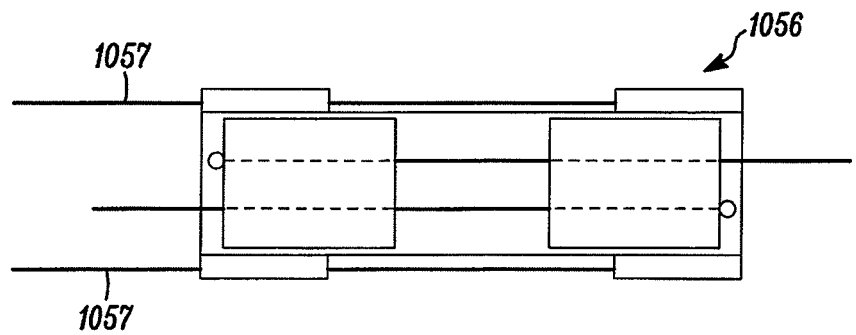
FIGS. 63A-63C are top views of a portion of a tissue modification device including side wires for facilitating guiding of the portion according to an alternative embodiment of the present invention.
Figure 63B:
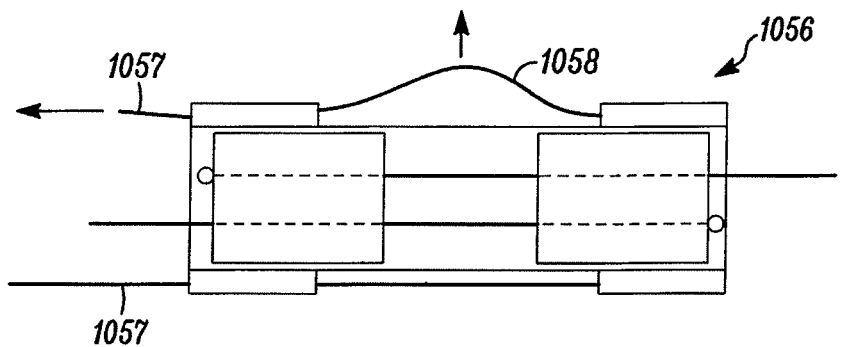
Figure 63C:
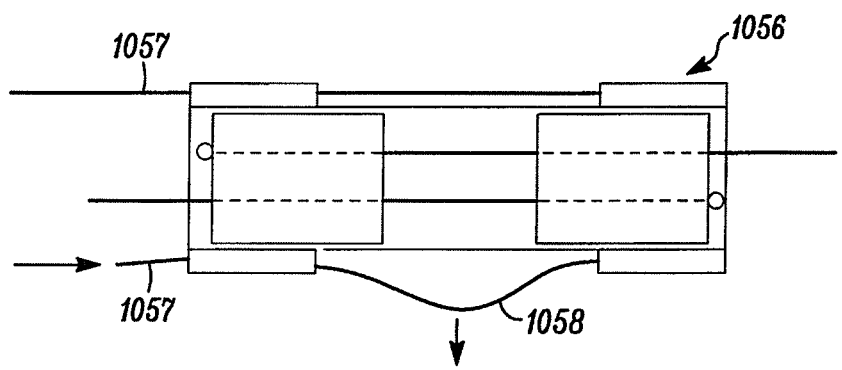

Top-view FIGS. 63A-63C further demonstrate one embodiment of a tissue modifying portion 1056 (here a cutting blade mechanism). These figures show how using push wires 1057 and side-loop wires 1058 on opposite sides of tissue modifying portion 1056, a user may move, guide or steer tissue modifying portion 1056 from side to side (FIGS. 63B and 63C).

Figure 64A:
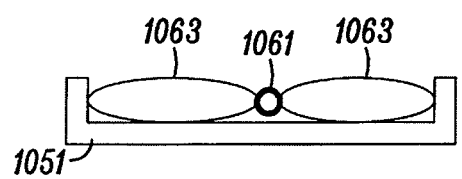

In yet another embodiment, as shown in end-on views in FIGS. 64A-64C, lateral displacement control of a tissue modification device may use one or more fellable bladders 1063, which may be filled or emptied of water, saline, air, or other fluid or gaseous medium to direct one or more components of a tissue modification device to one side or another. In one embodiment, for example, bladders 1063 may be aligned on either side of a track 1061, as depicted in FIG. 64A. As shown in FIGS. 64B and 64C, one bladder 1063 may be deflated or emptied while the other bladder 1063 is filled to move track 1061 to one side, and then the emptied bladder 1063 may be filled and the filled bladder 1063 emptied to move track 1061 to the opposite side.

In yet another embodiment, and with reference now to FIGS. 65A and 65B, a track 1061 is fixed to proximal and distal ends of a backing plate 1062, and the position of track 1061 in between the proximal and distal ends is controlled by a lateral displacer 1064, as shown in top-view in FIG. 65A. When force is applied to move lateral displacer 1064, track 1061 may be shifted relative to backing plate 1062, as shown in FIG. 65B. A cutting blade mechanism advanced or retracted along track 1061 may be controllably displaced from side to side by controlling lateral displacer 1064.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. For example, in many of the embodiments described above, one or more abrasive tissue modifying members may be substituted for one or more bladed tissue modifying members or vice versa. These an many other modifications may be made to many of the described embodiments. Therefore, the foregoing description is provided primarily for exemplary purposes and should not be interpreted to limit the scope of the invention as it is set forth in the claims.

What is claimed is:

1. A device for modifying tissue in a spine configured for insertion through a first incision on a patient, the device comprising: an elongate body extending distally and proximally;

a movable tissue modifying member comprising a substantially flat tissue engaging face including a plurality of cutting edges, the movable tissue modifying member located at or near a distal end of the elongate body;

a flexible shaft extending the length of the elongate body, the flexible shaft coupled to the movable tissue modifying member and having a drive member coupled with the movable tissue modifying member and configured to actuate the movable tissue modifying member, wherein being configured to actuate the movable tissue modifying member includes being configured to move the substantially flat tissue engaging face for causing the cutting edges thereof to at least one of move in a linear manner, move in a rotational manner, and move in an oscillatory manner;

a guidewire coupler or anchor member at the distal end of the elongate body device configured to grasp a guidewire extending through at least a portion of the elongate body from the distal end of the elongate body and outwardly through a second incision on the patient for applying a tensioning force pulling the tissue modifying member against a target tissue to be modified; and a trigger handle at a proximal end of the elongate body, the trigger handle being fixed to the elongate body and having an actuator used to activate the tissue modifying member, the actuator being a trigger in combination with a power transmission member coupled to the drive member to power the drive member, the trigger that when squeezed or pulled causes the tissue modifying member to modify the target tissue.

2. The device of claim 1, wherein the movable tissue modifying member is configured to rotate about an axis extending substantially perpendicular to the substantially flat tissue engaging face when actuated by the drive member.

3. The device of claim 1, wherein the movable tissue modifying member is configured to reciprocate along an axis extending substantially parallel to the substantially flat tissue engaging face when actuated by the drive member.

4. The device of claim 1, wherein the tissue modifying member is mounted on the drive member.

5. The device of claim 1, wherein the substantially flat tissue engaging face includes an abrasive member defining the plurality of cutting edges.

6. The device of claim 1, further comprising a motor at the proximal end of the device coupled to the drive member.

* * * * *